(12) United States Patent
Scott et al.

(10) Patent No.: US 6,593,753 B2
(45) Date of Patent: Jul. 15, 2003

(54) SYSTEM AND METHOD FOR MONITORING SUBSTANCES AND REACTIONS

(75) Inventors: Bentley N. Scott, Garland, TX (US); Samuel R. Shortes, Highland Village, TX (US)

(73) Assignee: Phase Dynamics, Inc., Richardson, TX (US)

( * ) Notice: Subject to any disclaimer, the term of this patent is extended or adjusted under 35 U.S.C. 154(b) by 0 days.

(21) Appl. No.: 09/747,169

(22) Filed: Dec. 21, 2000

(65) Prior Publication Data

US 2001/0019271 A1 Sep. 6, 2001

Related U.S. Application Data

(63) Continuation of application No. 09/416,306, filed on Oct. 12, 1999, now Pat. No. 6,166,551, which is a continuation of application No. 09/072,822, filed on May 5, 1998, now Pat. No. 5,966,017, which is a continuation of application No. 08/592,716, filed on Jan. 26, 1996, now Pat. No. 5,748,002, which is a continuation of application No. PCT/US94/08531, filed on Jul. 26, 1994.

(51) Int. Cl.$^7$ .......... G01R 27/04; G01R 27/32; G01R 23/00; G01N 27/00
(52) U.S. Cl. .......... 324/637; 324/629; 324/632; 324/633; 324/639; 324/76.5; 324/71.1
(58) Field of Search .......... 324/679, 632, 324/633, 76.51, 639, 637, 71.1; 426/234

(56) References Cited

U.S. PATENT DOCUMENTS

| | | | | |
|---|---|---|---|---|
| 4,524,079 A | * | 6/1985 | Hofmann | 426/234 |
| 5,052,222 A | * | 10/1991 | Scott et al. | 324/639 |
| 5,966,017 A | * | 10/1999 | Scott et al. | 324/639 |
| 6,348,803 B1 | * | 11/2000 | Mohr | 324/642 |
| 6,166,551 A | * | 12/2000 | Scott et al. | 324/637 |

* cited by examiner

*Primary Examiner*—N. Le
*Assistant Examiner*—Wasseem H. Hamdan

(57) ABSTRACT

Systems, methods, and probe devices for electronic monitoring and characterization using single-ended coupling of a load-pulled oscillator to a system under test.

6 Claims, 62 Drawing Sheets

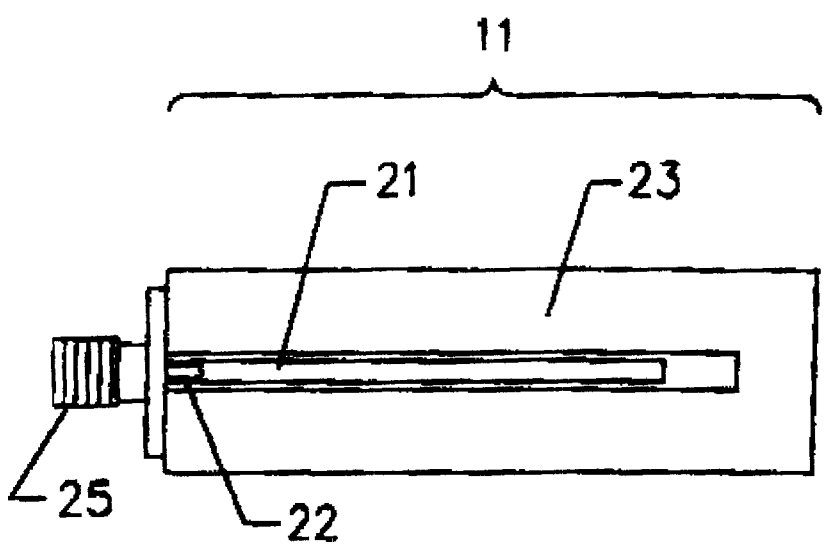
FIG. 1A1
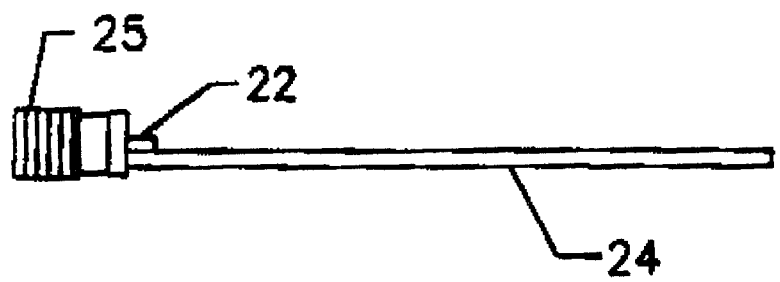
FIG. 1A2

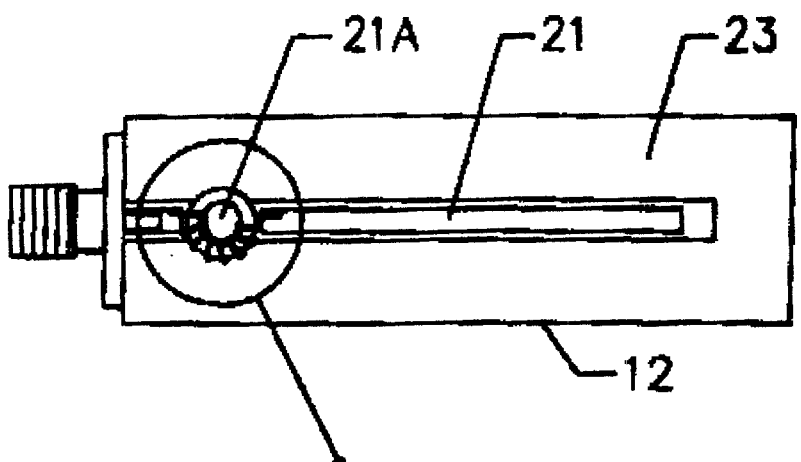
FIG.1B1
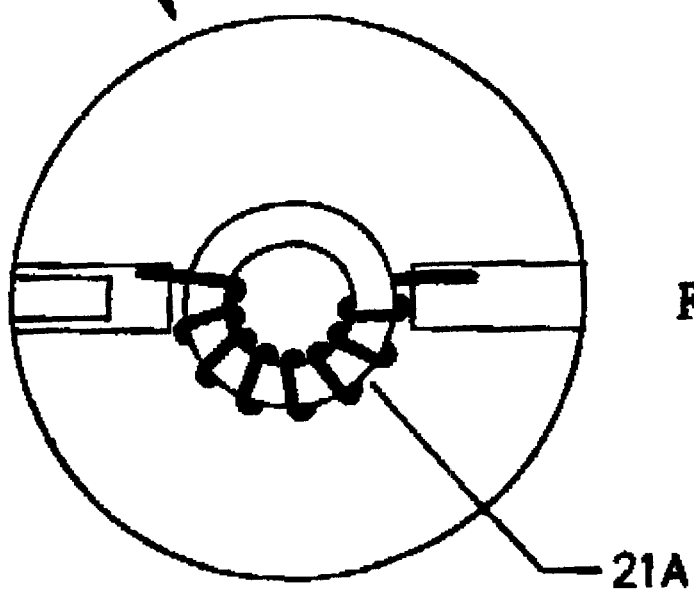
FIG.1B2

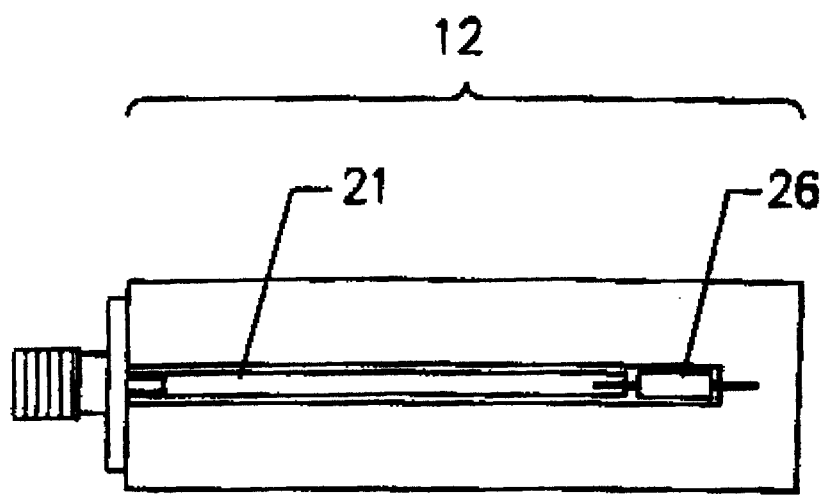
FIG.2A1
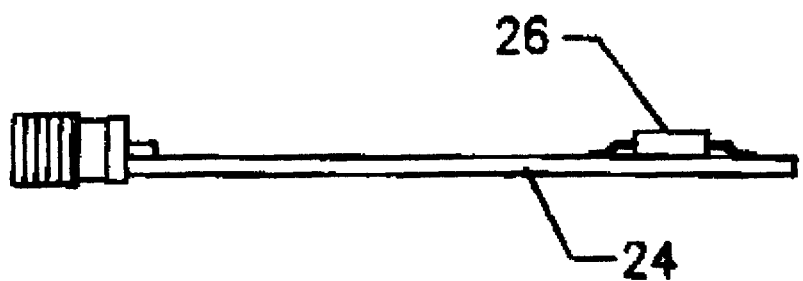
FIG.2A2

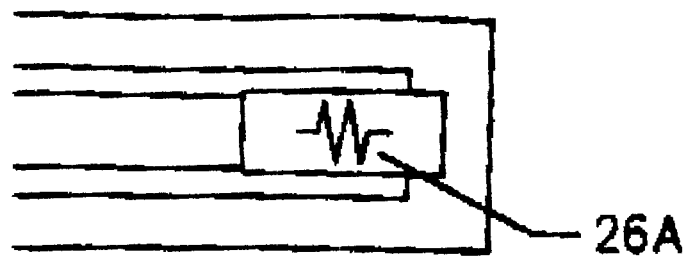
FIG.2B1
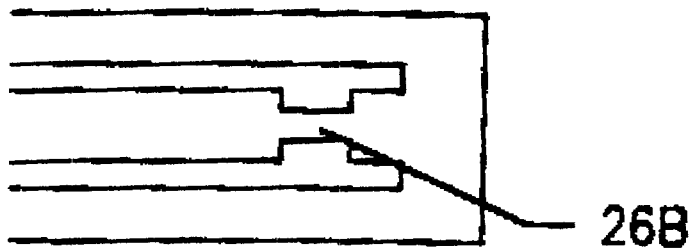
FIG.2B2
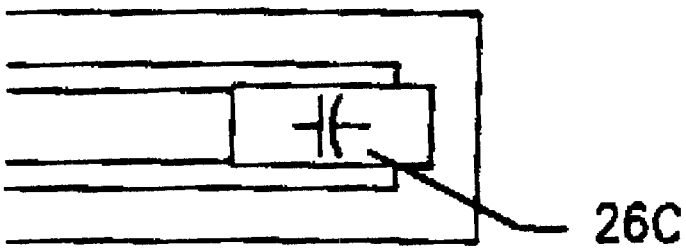
FIG.2B3
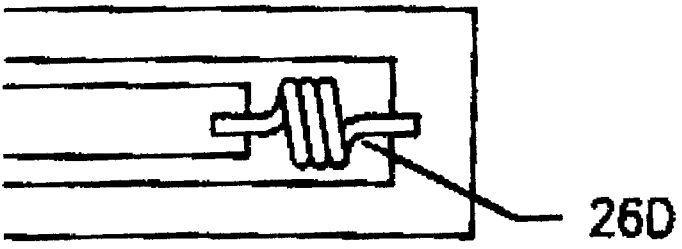
FIG.2B4
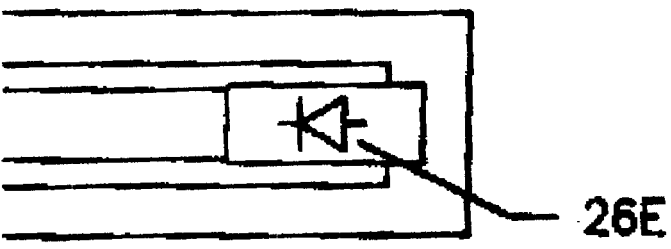
FIG.2B5

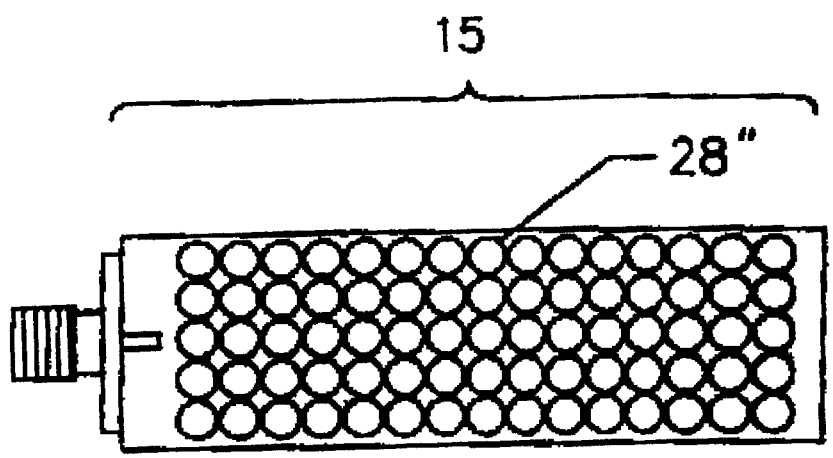
FIG.4B1
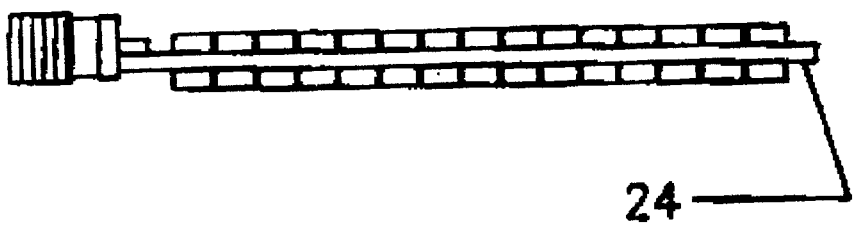
FIG.4B2

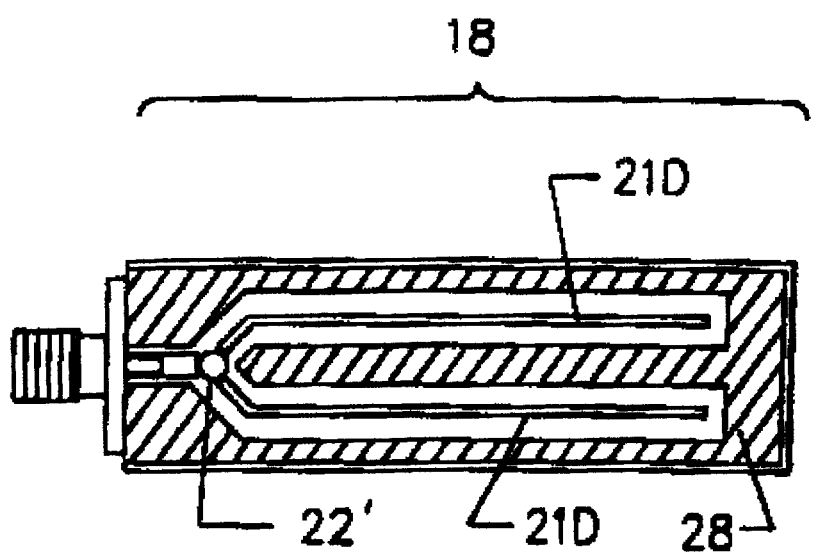
FIG.4E1
FIG.4E2

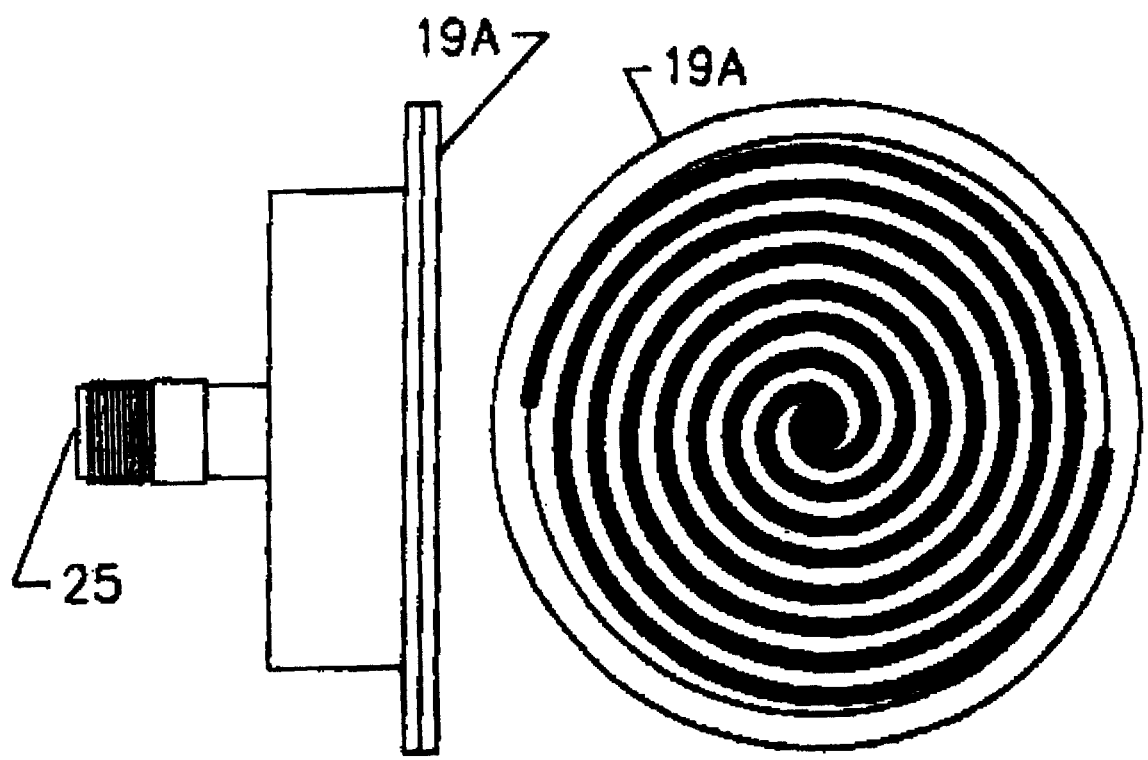
FIG.7A2　　　FIG.7A1

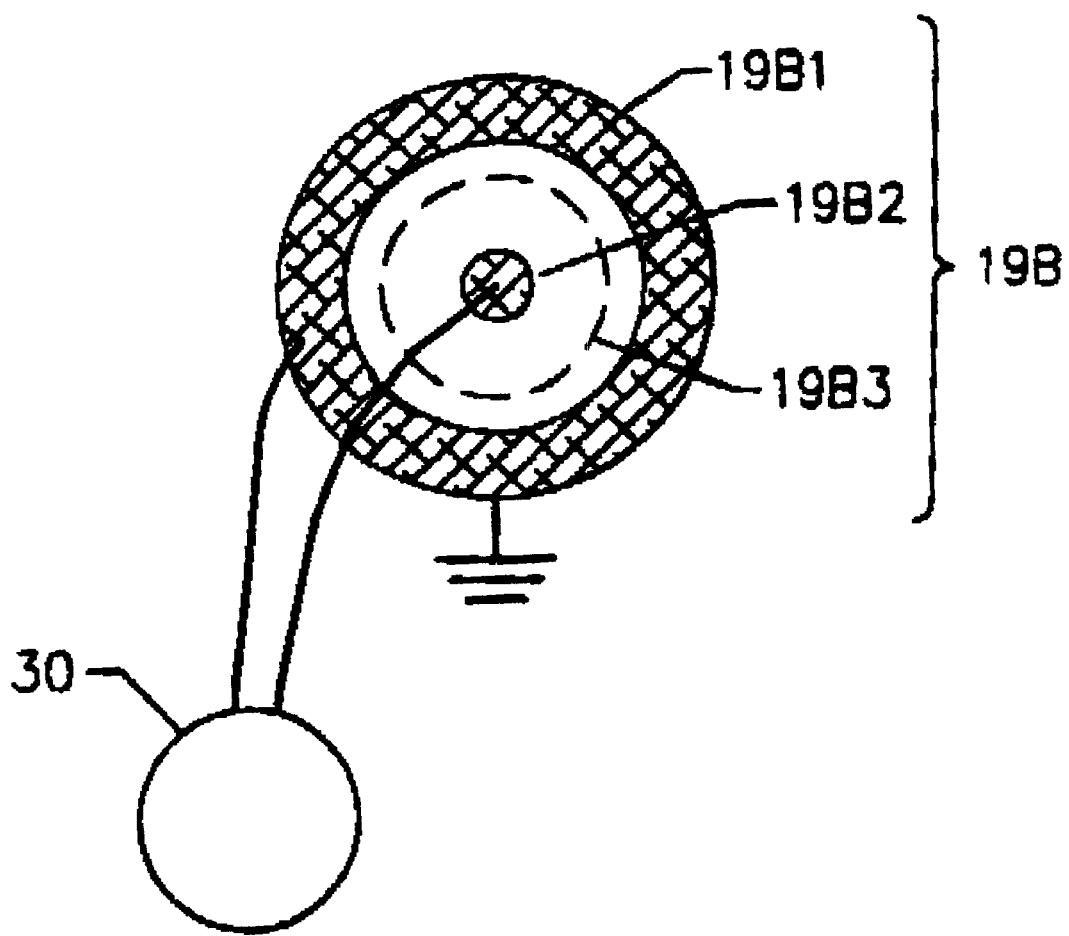
FIG.7B1

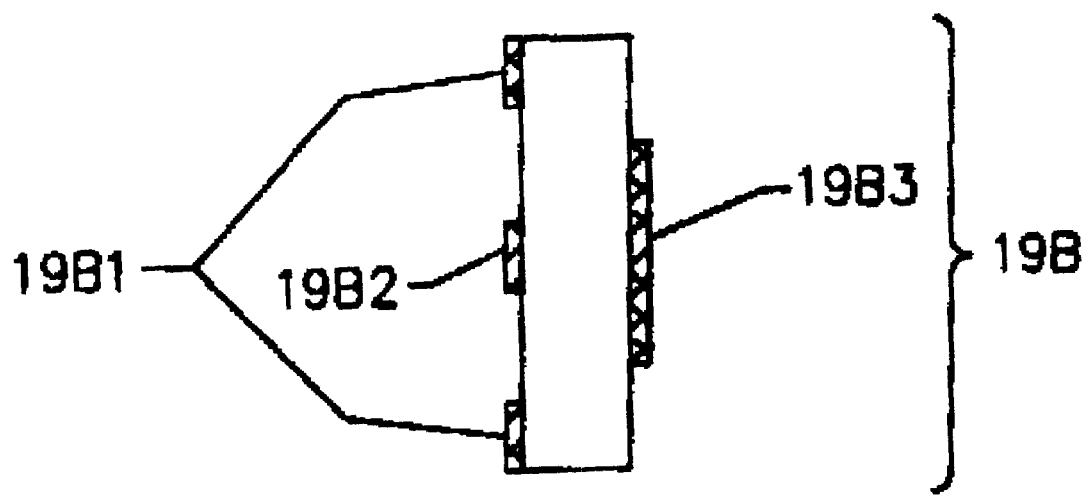
FIG.7B2

SYSTEM AND METHOD FOR MONITORING SUBSTANCES AND REACTIONS

This application is a continuation of U.S. Ser. No. 09/416,306, filed Oct. 12, 1999, and which issued as U.S. Pat. No. 6,166,551 on Dec. 26, 2000, which is itself a Continuation of U.S. Ser. No. 09/072,822, filed May 5, 1998 and which issued as U.S. Pat. No. 5,966,017 on Oct. 12, 1999, which is itself a Continuation of Ser. No. 08/592,716, filed Jan. 26, 1996, which issued as U.S. Pat. No. 5,748,002 on May 5, 1998 and which itself is a Continuation of PCT/US94/08531, filed Jul. 26, 1994, which claim priority from U.S. app'ns Ser. Nos. 08/096,940, 08/096,954, 08/096,963, 08/096,964, 08/097,406, 08/097,407, 08/097,408, 08/097,409, 08/097,410, 08/097,411, and 08/097,412, now abandoned

BACKGROUND AND SUMMARY OF THE INVENTION

The present invention relates to load-pulled electronic measurement and characterization systems.

Extensive work by the present inventors has shown that load-pulled oscillators have important new capabilities for measurement and characterization. See U.S. Pat. Nos. 4,862,060, 4,966,490, and 5,025,222, and PCT applications WO 91/00997 (published Jan. 24, 1991) and WO 91/08469 (published Jun. 13, 1991); all of which are hereby incorporated by reference. This "load-pull" technology provides an economical measurement technique which has improved sensitivities by 100× to 1000× over any prior instrumentation for measurement of microwave phase. This capability makes possible microwave measurements which were proposed in the 1950s but until now have not been available due to the lack of accurate technology. The ground work which was extensively formulated during the early years of microwave spectroscopy may now be utilized to bring about generations of products using this simple but powerful technique.

The previous work has established many of the basic principles, but has focused primarily on monitoring continuous streams of fluids (liquids or gas phase). The inventions disclosed herein provide new concepts for "sampling" the electrical characteristics of a wide variety of materials.

Background: The "Load-Pull" Effect

It is well known to electrical engineers generally (and particularly to microwave engineers) that the frequency of an RF oscillator can be "pulled" (i.e. shifted from the frequency of oscillation which would be seen if the oscillator were coupled to an ideal impedance-matched pure resistance), if the oscillator sees an impedance which is different from the ideal matched impedance. Thus, a varying load impedance may cause the oscillator frequency to shift.[1]

[1] Any electrical oscillator can be "pulled" to some extent—that is, its frequency can be shifted—by changing the net impedance seen by the oscillator. However, in many systems which use oscillators, pulling of a resonant circuit's frequency is undesirable. An oscillator which is too easily pulled may be overly susceptible to irrelevant external circumstances, such as changes in parasitic capacitance due to human proximity or temperature change. Normal techniques to avoid oscillator pulling include using isolation/buffering circuits between the oscillator and the variable load, and/or using a high-Q tuned circuit to stabilize the oscillator.

The present application sets forth various innovative methods and systems which take advantage of this effect. In one class of embodiments, an unbuffered[2] RF oscillator is loaded by an electromagnetic propagation structure which is electromagnetically coupled, by proximity, to a material for which real-time monitoring is desired. The net complex impedance[3] seen by the oscillator will vary as the characteristics of the material in the electromagnetic propagation structure varies. As this complex impedance changes, the oscillator frequency will vary. Thus, the frequency variation (which can easily be measured) can reflect changes in density (due to bonding changes, addition of additional molecular chain, etc.), ionic content, dielectric constant, or microwave loss characteristics of the medium under study. These changes will "pull" the resonant frequency of the oscillator system. Changes in the medium's magnetic permeability will also tend to cause a frequency change, since the propagation of the RF energy is an electromagnetic process which is coupled to both electric fields and magnetic fields within the transmission line.

[2] An unbuffered oscillator is a oscillator without buffer amplifiers or attenuators. Amplifiers boost the output power and provide isolation from the load impedance changes. Attenuators decrease the amplitude while providing an isolation of two times the attenuation. In the load pulled oscillator configuration the oscillator feedback path that supplies the phase shift needed for oscillation is separated from the load.

[3] A "complex" number is one which can be written as A+Bi, where A is the number's "real" part, B is the number's "imaginary" part, and $i^2=-1$. These numbers are added according to the rule $$(A+Bi)+(C+Di)=(A+C)+(B+D)i,$$

and are multiplied according to the rule $$(A+Bi)(C+Di)=(AC-BD)+(AD+BC)i.$$

Complex numbers are used in representing many electrical parameters. For example, impedance can be represented as a complex number whose real part is the resistance, and whose imaginary part is equal to the reactance (inductance or capacitance).

Similarly, permittivity can be represented as a complex number whose imaginary part represents resistive loss, and whose real part represents reactive loading, by the medium, of the propagating electromagnetic wave.

Background: Properties of a Dielectric in a Transmission Line

To help explain the use of the load-pull effect in the disclosed innovations, the electromagnetics of a dielectric-loaded transmission line will first be reviewed. If a transmission line is (electrically) loaded with a dielectric material, changes in the composition of the dielectric material may cause electrical changes in the properties of the line. In particular, the impedance of the line, and the phase velocity of wave propagation in the line, may change.

This can be most readily illustrated by first considering propagation of a plane wave in free space. The propagation of a time-harmonic plane wave (of frequency f) in a uniform material will satisfy the reduced wave equation $$(\nabla^2+k^2)E=(\nabla^2+k^2)H=0,$$

where

E is the electric field (vector),

H is the magnetic field (vector), and $\nabla^2$ represents the sum of second partial derivatives along the three spatial axes.

This equation can be solved to define the electric field vector E, at any point r and time t, as $$E(r,t)=E_0 exp[i(k \cdot r-\omega t)],$$

where k is a wave propagation vector which points in the direction of propagation and has a magnitude equal to the wave number k, and $\omega$=Angular Frequency=$2\pi f$.

In a vacuum, the wave number k has a value "$k_0$" which is $$k_0 = \omega/c$$

$$= \omega(\mu_0 \varepsilon_0)^{1/2},$$

where $\mu_0$=Magnetic Permeability of vacuum ($4\pi \times 10^{-7}$ Henrys per meter), $\varepsilon_0$=Electric Permittivity of vacuum (($1/36\pi) \times 10^{-9}$ Farads per meter), and c=Speed of light=$(\mu_0 \varepsilon_0)^{-1/2}$=$2.998 \times 10^8$ meters/second.

However, in a dielectric material, the wave number k is not equal to $k_0$; instead $$k = \omega/(c(\mu_r \varepsilon_r)^{1/2})$$

$$= \omega(\mu_0 \mu_r \varepsilon_0 \varepsilon_r)^{1/2},$$

where $\mu_r$=Relative Permeability of the material (normalized to the permeability $\mu_0$ of a vacuum), and $\varepsilon_r$=Relative Permittivity of the material (normalized to the permittivity $\varepsilon_0$ of a vacuum).

Thus, if the relative permeability $\mu_r$ and/or the relative permittivity $\varepsilon_r$ vary, the wave number k and the wave propagation vector k will also vary, and this variation will typically affect the load pulled oscillator frequency.[4]

[4]The full analysis of wave propagation in a cavity or at a boundary is much more complex, but in any case wave propagation will depend on the wave number, and the foregoing equations show how the wave number k can vary as the medium changes. See generally, e.g., R. Elliott, *Electromagnetics* (1966); J. Jackson, *Classical Electrodynamics* (2d ed. 1975); G. Tyras, *Radiation and Propagation of Electromagnetic Waves* (1969); R. Mittra & S. Lee, *Analytical Techniques in the Theory of Guided Waves* (1971); L. Lewin, *Theory of Waveguides* (1975); all of which are hereby incorporated by reference.

Frequency Hopping in a Load-Pulled Oscillator

In a typical free-running oscillator, the oscillator frequency is defined by a resonant feedback circuit (the "tank" circuit), and can also be pulled slightly by a reactive load,[5] as noted above. Thus, such an oscillator can be broadly tuned by including a varactor in the tank circuit.[6]

[5]The degree by which the reactive load can change the oscillator's frequency will depend on the coupling coefficient between the load and the tank circuit. Thus, an increased coupling coefficient means that the oscillator frequency will be more sensitive to changes in the load element. However, the coupling coefficient should not be increased to the point where spectral breakup (multiple frequency operation) occurs, since this would render the desired measurement of the oscillator signal impossible.
[6]This is one type of voltage-controlled oscillator (VCO).

As the oscillator's frequency is thus shifted, the phase difference between the energy incident on and reflected from the load element (which is preferably a shorted transmission line segment) will change. This phase difference will be equal to an exact multiple of 180· at any frequency where the electrical length of the transmission line segment is an exact multiple of $\lambda/4$.

As the oscillator frequency passes through such a frequency (i.e. one where the transmission line segment's electrical length is equal to a multiple of $\lambda/4$), the load's net impedance will change from inductive to capacitive (or vice versa). As this occurs, the frequency of the oscillator may change abruptly rather than smoothly.[7] This jump in frequency will be referred to as a frequency "hop".[8]

[7]This change in frequency, as the load goes from capacitive (−180·) to inductive (+180×) or vice versa, is instantaneous if the equivalent parallel resistive part is large (e.g. greater than approximately 500 ohms in a 50 ohm system).
[8]The amount by which the frequency shifts during the "hop" will depend on the Q of the load element (as seen by the oscillator circuit), and on the coupling coefficient between the load element and the tank circuit.

For a transmission line of length l which contains a dielectric material of relative dielectric constant $\varepsilon_r$, the frequency at which one full wavelength ($1\lambda$) exists in the transmission line is equal to c (the speed of light in vacuum, which is $2.995 \times 10^8$ meters/second) divided by the length of the line in meters and by the square root of the relative dielectric constant of the material:

$$\text{Frequency}_{1\lambda} = c/(l\varepsilon_r^{1/2}).$$

For example, for a one-foot-long line filled with a material having $\varepsilon_r=1$, l=12 inches (=0.3048 meters), and $$\text{Frequency}_{1\lambda} = (2.995 \times 10^8)/(0.3048 \times 1.0) \approx 980 \text{ MHz.}$$

However, since one wavelength actually contains two excursions from inductive to capacitive reactive impedances, only one-half wavelength is required to see one frequency hop of the load pulled oscillator. If the transmission line is terminated into a short or an open, the resulting effective length is increased to twice the actual length, since a standing wave is generated (due to the energy incident at the short or open being reflected back to the input of the transmission line). In essence, the energy travels down the line, gets reflected, and travels back to the input. With this taken into account, the first frequency with a wavelength long enough to cause a frequency "hop" of the oscillator is one fourth the length calculated above, or 245 MHz.

Multiples of this first quarter-wavelength frequency will also cause the impedance seen at the input to the transmission line to go from inductive to capacitive reactance. The longer the transmission line, the greater the number of phase transitions that will occur. Longer line length also multiplies the phase changes that are brought about by a change in the dielectric constant. For every one-quarter wavelength change in the effective (electrical) length of the line, the complex impedance seen at the oscillator changes by 180·.

For example, suppose that a given oscillator, coupled into a low loss load with an electrical length of one-quarter wavelength ($\lambda/4$), provides 50 MHz of load pulling frequency change (total excursion through all phases). If the monitored material changes enough to produce a change of only one degree of phase in the electrical length of the load, the oscillator frequency will change by 138.9 kHz. This represents an absolute resolution of $7.2 \times 10^{-6}$ degrees of phase change for each Hertz of sensitivity.[9] For every additional quarter wavelength of line length, this sensitivity to phase is multiplied by 1.5. This is due to the change in phase being an additive function of every additional quarter wave in the measurement section.

[9]Even if the resolution of frequency measurement is only ±100 Hz, this would still give an accuracy of better than one-thousandth of one degree. This is vastly better resolution than is possible with vector impedance systems (such as an HP 8510 Network Analyzer).

In a typical tuning frequency versus voltage plot for a VCO loaded into a shorted transmission line, the height of the "hop" can be measured by holding the VCO tuning voltage constant, while a transmission line terminated into a short is varied in length[10] to cause a full rotation of the impedance vector seen at the VCO's input port. The resulting data of frequency versus length of the transmission line will show a jump in frequency (a delta frequency from the bottom of the "hop" to the top of the "hop") which coincides with the delta frequency of the "hop" seen when the VCO was swept using the tuning voltage.

[10]Such variable transmission lines are commonly used in the microwave industry, and are referred to as "line stretchers."

Thus, if the VCO is swept across a frequency band and the number of frequency "hop" was counted, the number of "hops" reveals the number of wavelengths in the transmission line.[11]

[11]More precisely, it will be found that the wavelengths at which hops are observed are separated from each other by one-quarter of the effective (electrical) length of the measurement section.

This provides a means for determination of the range of dielectric constant change in a medium even when it rotates the phase vector multiple times (and therefore, the oscillator frequency returns to the same value multiple times). If the dielectric constant of the material in the transmission line is increased, then the above equations show that the frequency of the first full wavelength is decreased by the square root of the dielectric constant. Additionally, this means that the number of wavelengths at a fixed frequency increases with increasing dielectric constant. These facts imply that the VCO tuning curve will see more "hops" as the dielectric constant is increased due to the increasing fraction or whole wavelengths encountered.

Ideally, the oscillator will not cease oscillations (or break into multiple frequency oscillation or spectral breakup) into any load regardless of the load characteristics. However, this is not a strictly necessary condition for use of the disclosed method and system innovations.[12]

[12]The second harmonic of the oscillator frequency is typically enhanced (becoming greater in amplitude than the fundamental frequency) just before the shift from inductive to capacitive impedance (or vice versa), due to the extreme non-linearities at this point. This does not hinder the use of load pulling as a measurement technique, since the measurement is typically made outside of this region of the impedance shift from inductive to capacitive. Alternatively, the second harmonic may be filtered out of the measurement.

Measurement of Substances with a High Microwave Loss Factor

A measure of the dielectric loss of a material is typically given as the dielectric loss tangent (a unitless number) which is defined as the tangent of the imaginary part divided by the real part of the complex dielectric constant. Low loss materials are typically below a loss tangent equal to or less than 0.01. When the disclosed systems are used to measure materials with a high loss factor, the material's absorption begins to dominate the load versus frequency effects, but a measurement capability still exists due to the sensitivity of the load pulling method.

Additional Information from Load Pull Measurement

A load-pull system also permits other information to be derived, regarding the substance being monitored.

Difference in Operation Frequency

Additional information can be obtained by retuning the VCO, so that the frequency is forced to change, and making another measurement at a much higher frequency. Since materials change properties versus frequency, the amount of frequency change due to load pulling will vary versus the frequency of operation.

A VCO will typically be designed to cover approximately one octave above its turn on frequency. If a VCO would not give enough frequency change to see the desired range of varying parameters versus operating frequency, an additional unbuffered oscillator, which runs at any frequency required to obtain appropriate data, may be switched into the coaxial line.

When two widely spaced frequencies are measured for a medium under study with a load pulled oscillator, the difference (delta) frequency between these two measurements will be unique for a given medium. This phenomena will aid in distinguishing constituents and the progress of mixing or reaction.

Monitoring of Insertion Loss

If the incident power and the reflected power is measured in a system where the final load is a short, the difference in powers will be twice the insertion loss of the medium (since two transits occur through the medium of interest). The insertion loss measurement will aid in determination of the changing conductivity of the medium or its change in absorption of the RF energy. This information can be related to the mixing or reaction products to further distinguish unique situations where the frequency change of the load pulled oscillator is not enough information or resolution by itself.

Effect of Complex Permeability

The magnetic permeability $\mu_r$ can also be dynamically measured by the disclosed techniques. Since the velocity varies with $(\mu_r \epsilon_r)^{-\frac{1}{2}}$, changes in $\mu_r$ will change the phase shift through a given physical length of line, and thus change the frequency of the oscillator.

A sample-containing waveguide, like that of the principally preferred embodiment, will typically have locations where the electric field is strong but the magnetic field is zero; at such locations only permittivity will affect the oscillator load pull frequency. However, there will also commonly be locations in a waveguide where the magnetic fields are locally strong and electric field is zero: at these locations, only the permeability will affect the propagation characteristics of the transmission line (and therefore contribute to the oscillator frequency).

A system can be built to sample (primarily) one of theses parameters. For example, to sample the permeability, the coaxial transmission line will be terminated into a short where the medium of interest is located only in close proximity to the short. A waveguide structure supports very well defined electrical and magnetic field functions, and the sample can be suitably placed in such a structure to measure primarily the permeability.

Typical compounds and substances do not have varying magnetic permeabilities and therefore, most of the discussion will involve the changing complex permittivity. However, the effects of changing complex permeability will create similar changes in the oscillator load pulling characteristics. If a substance such as barium titanate is studied, the effect of the changing permeability must be considered along with the change in permittivity unless the system is designed specifically to measure only one of these.

Coupling the Active Device

An unusual feature of the oscillator configuration used with the present invention is the separation of the load of interest from the resonant circuit proper. The configuration used isolates the two through the active device. It is the non-linear behavior of the transistor that provides the changes in the frequency as the load is changed. The loop gain of an oscillator must be unity with an appropriate phase shift to cancel the negative impedance's imaginary part[13] around the resonant loop. The initial gain of the active device must be greater than unity before oscillations can begin in order for the oscillator to be self starting. This extra gain is reduced to unity by the saturation of the active device upon establishment of the oscillations. Saturation of a device normally also changes the phase shift through the device[14]. This requires a change in the operation frequency as the load changes due to the shift in loop gain and phase by the saturated condition change in the active device.

[13] In a simple resistor, an increase in the current passing through the resistor will produce an increase in the voltage across the resistor. By contrast, in microwave gain diodes (or in a transistor with feedback connections) which is operating at less than its saturated current, a small transient increase in the current across the device will produce a reduction in the voltage across the device. Thus, since a simple resistor has a positive impedance, such gain devices are referred to as having a negative impedance.

[14] As the gain device approaches saturation, the physics of its operation will gradually change. These changes may cause the phase shift across the gain device to vary significantly Note that, in the saturation regime, the gain device behaves as a non-linear circuit element Spectral Purity of Oscillator It has been discovered that, in a system using a free-running oscillator as described above, spectral purity of the oscillator is an important concern. Many microwave oscillators exhibit "spectral breakup," wherein the spectrum of the oscillator's output actually contains multiple frequencies. In most microwave oscillators this is not a problem, since a tuned feedback element will be used to stabilize the gain element, and/or isolation or buffering stages are used to prevent the oscillator's feedback loop from being perturbed by extraneous resonances. However, in a load-pulled system, since such buffer stages are not used, spectral purity turns out to be quite important. For example, a spurious resonance in the feedback loop (e.g. due to a low-quality RF choke, or due to two impedance mismatches) can permit the oscillator to hop to a frequency which is determined (at least partly) by a harmonic of the spurious resonance, in which case the degree to which the oscillator frequency has been pulled by the changing load will be obscured.

To avoid such problems in a load-pulled system, a small series resistor can be interposed in the RF output of the oscillator, before the measurement section connection. This resistor adds a small amount of damping, which helps to suppress oscillation at secondary frequencies).

To further improve stability, a shunt resistor can be attached to the RF output of the load-pulled oscillator. This resistor adds to stability, by fixing a maximum magnitude for the load impedance seen at the RF output line.[15]

[15] At frequencies where the length of the transmission line segment is a multiple of K/4, its impedance can become very large.

Background: Other Approaches to Electrical Characterization

Various types of apparatus have been proposed for measuring the concentration of one substance in another, particularly the concentration of a liquid or flowable substance in another liquid of flowable substance. Various devices which utilize the broad concept of determining composition of matter by measuring changes in a microwave signal are disclosed in U.S. Pat. No. 3,498,112 to Howard; U.S. Pat. No. 3,693,079 to Walker; U.S. Pat. No. 4,206,399 to Fitzky et al.; U.S. Pat. No. 4,311,957 to Hewitt et al.; U.S. Pat. No. 4,361,801 to Meyer et al.; U.S. Pat. No. 4,240,028 to Davis Jr.; U.S. Pat. No. 4,352,288 to Paap et al.; U.S. Pat. No. 4,499,418 to Helms et al.; and U.S. Pat. Nos. 4,367,440 and 4,429,273, both to Mazzagatti; all of which are hereby incorporated by reference.

Although various systems utilizing microwave transmissivity or signal alteration characteristics have been proposed in the prior art, certain considerations in utilizing microwave energy to detect the presence of the concentration of one medium in another have not been met by prior art apparatus. In particular, it is desirable in certain instances to be able to accurately measure, on a continuous basis, the concentration or change in concentration of one fluid in another and particularly where the concentration of one fluid is a very low percentage of the total fluid flow rate or fluid mixture quantity. It is also desirable that the signal change caused by the presence of one substance or medium in another be easily measured and be relatively error free, again, particularly in instances where measurements of low concentrations of one substance such as a fluid in another substance such as another fluid are being taken. Moreover, it is important to be able to transmit the microwave signal through a true cross section of the composition being sampled or measured to enhance the accuracy of the measurement.

Typical systems for capacitive based measurement have a capacitive element, used for parameter determination, as part of the resonant feedback loop around an active device. This method works well with very low loss systems, but oscillation ceases with even slightly lossy measurements. As the frequency is increased into the microwave region, it becomes difficult to configure the resonant feedback loop due to the increase in loss versus frequency and the wavelength becoming comparable to the path length. In this case the frequency is changed directly by the resonance change in the feedback loop which includes the element that consists of the sample to be measured. This frequency change is limited to the characteristics and loss of the feedback path and can only be changed over a narrow frequency range with out cessation of oscillations. This limits the measurement technique to small samples of very low loss.

At higher frequencies (above approximately 100 MHz), the capacitive measurement technique fails to work, due to line lengths and stray capacitances. At such frequencies resonant cavity techniques have been employed. (For example, a sample is placed in a resonant cavity to measure the loss and frequency shift with a external microwave frequency source that can be swept across the resonance with and without the sample in the cavity.) This method uses a highly isolated microwave frequency source which is forced by the user (rather than being pulled by the changing resonance) to change its frequency. This technique too meets substantial difficulties. For example, the use of multiple interfaces without a microwave impedance match at each interface causes extraneous reflections, which tend to hide the desired measurement data. This technique too gives errors with very lossy material, but in this case it is due to the very rounded nature of the resonance curve (which is due to the low Q of the loaded cavity). This rounded curve makes it difficult to determine both the center frequency and the 3 dB rolloff frequency closely enough to be accurate in the measurement.

Another technique which is used encompasses the use of a very sharp rise time pulse to obtain time domain data, from which frequency domain values are then derived through transformation techniques.

In U.S. Pat. No. 4,396,062 to Iskander, entitled Apparatus and Method for Time-Domain Tracking of High-speed Chemical Reactions, the technique used is time domain reflectometry (TDR). This contains a feedback system comprising a measurement of the complex permittivity by TDR means which then forces a change in frequency of the source which is heating the formation to optimize this operation. Additionally it covers the measurement of the complex permittivity by TDR methods.

U.S. Pat. No. 3,965,416 to Friedman appears to teach the use of pulse drivers to excite unstable, bi-stable, or relaxation circuits, and thereby propagate a pulsed signal down a transmission line which contains the medium of interest. The pulse delay is indicative of the dielectric constant of the medium. As in all cases, these are either square wave pulses about zero or positive or negative pulses. The circuit is a pulse delay oscillator where the frequency determining element is a shorted transmission line. The frequency generated is promoted and sustained by the return reflection of each pulse. The circuit will not sustain itself into a load that is lossy, since the re-triggering will not occur without a return signal of sufficient magnitude. In addition, the circuit requires a load which is a DC short in order to complete the DC return path that is required for re-triggering the tunnel diodes.

The frequencies of operation of any pulse system can be represented as a Fourier Series with a maximum frequency which is inversely dependent upon the rise time of the pulse. Therefore, the system covered in the Friedman patent is dependent upon the summation of the frequency response across a wide bandwidth. This causes increased distortion of the return pulse and prevents a selective identification of the dielectric constant versus frequency. This also forces a design of the transmission system to meet stringent criteria to prevent additional reflections across a large bandwidth.

The low frequency limit of the TDR technique is determined by the time window which is a function of the length of the transmission line. The upper extreme is determined by the frequency content of the applied pulse. In the case of this pulse delay line oscillator, the upper frequency is determined to a greater extent by the quality of impedance match (the lack of extra reflections) from the circuit through to the substance under study. These extra reflections would more easily upset the re-triggering at higher frequencies.

In one case (FIG. 1 of Friedman) the return reflection initiates a new pulse from the tunnel diode and therefore sets up a frequency (pulse repetition rate) as new pulses continue to be propagated. This is in essence a monostable multivibrator with the return reflection being the trigger. The problem implied, but not completely covered with this approach, is that due to the delay in pulses, the pulse train can overlap and cause multiple triggers to occur. These are caused by the re-reflections of the original parent pulse. An additional problem is with very lossy dielectrics, which will not provide enough feedback signal to initiate the next pulse. If the dielectric medium is of high enough dielectric constant to contain more than one wavelength, or if the dielectric constant of the samples vary greatly, multiple return reflections will alter the behavior of the circuit to render it useless due to the interfering train of return and parent pulses.

FIG. 3 of Friedman shows a bistable multivibrator which senses the return pulse by sampling and feeding back enough phase shifted voltage to re-set the tunnel diodes. Since this device is also dependent upon the return to trigger or re-trigger the parent pulse, it suffers problems with lossy dielectrics and high dielectric constant mediums.

To overcome these problems, the relaxation oscillator of FIG. 4 of Friedman was proposed that contains a RC (resistor/capacitor timing) network which will maintain the generation of pulse trains using resistor 76 and capacitor 78 with the dielectric filled transmission line affecting the regeneration of the pulses as the reflected parent pulse voltage is returned. Since the RC time constant is defining the basic repetition rate, some improvement is obtained in reducing second order effects. The transmission line is still an integral part of the overall relaxation oscillator and lossy dielectrics may cause irregular circuit response. The proposed inverting amplifier as the pulse generator will not function at above approximately 1 MHz in frequency due to the characteristics of such inverting amplifiers. The tunnel diode can pulse up to a 100 MHz rate.

By contrast, the innovative system embodiments disclosed in the present application and its parents differ from the known prior art in using a microwave frequency generated by a free running sine wave oscillator. The preferred oscillator has the versatile capability to work into a wide variety of transmission lines or other load impedance without generation of spurious data or cessation of oscillations. It will continue to oscillate with very lossy dielectrics. It is not a relaxation oscillator or a multivibrator. The frequency of the un-isolated oscillator is dependent upon the net complex impedance of the transmission line and will work into an open circuit as well as a short circuit. The net complex impedance at the frequency of operation of the oscillator looking at the transmission line containing the medium of interest results in stable oscillations through pulling of the unisolated oscillator. Only one frequency at any one time is involved in the disclosed system proposed (not counting harmonics which are at least 10 dB down from the fundamental). This provides for well defined information and eases the transmission design criteria. This also provides for evaluation of the dielectric constant versus frequency which can improve resolution of constituents or ionic activity.

Another important difference from prior art is the separation of the load of interest from the resonant circuit proper. The configuration used isolates the two through the transistor. It is the non-linear behavior of the transistor that provides the changes in frequency as the load is changed. The loop gain of an oscillator must by unity with 180· phase shift. The initial gain of the transistor must be greater before oscillations begin in order for the oscillator to be self starting. This extra gain is reduced to unity by the saturation of the active device upon establishment of the oscillatory frequency. Saturating a device changes the gain (and accordingly the phase since it is non-linear) to maintain oscillations as the load changes. This will continue as the load changes as long as the transistor has appropriate phase and available gain to satisfy oscillations.

Summary of the Invention—Planar Probe

The present application discloses a planar probe which can be readily inserted into a variety of materials in solid, liquid, gas or plasma phase. This probe provides a "single-ended" coupling element which permits load-pull measurements to be made on an increased variety of materials. As with the coaxial configuration, oscillator frequency can be monitored directly, or in combination with insertion loss.

A variety of probes have been suggested for industrial microwave application. See, e.g., Nyfors & Vainikainen, INDUSTRIAL MICROWAVE SENSORS (Artech 1989), which is hereby incorporated by reference, and especially pages 226–228 thereof. Many of these probes can be used for load-pull application, but none of these probes are ideally suited: for example, the stripline probe shown on page 226 (FIG. 4.15) shields signal propagation in one direction, and thus lessens coupling to a medium to be sampled, which is undesirable in most load-pull applications.

By contrast, the disclosed planar probe provides very efficient coupling to the surrounding medium, in a compact, rugged, and easily manufactured design. The disclosed planar probe, unlike many previous arrangements, provides a single-ended structure for coupling to a material under test.

Such a probe turns out to provide very high sensitivity. A short length of transmission line in a planar structure has been found to be approximately 3 to 10 times as responsive (per unit length) as a section of coaxial line structure (like that shown in the previous load-pull applications cited above). This may be due to the third dimensional variable caused by the micro strip structure having one propagation velocity and the fluid under measurement having a second propagation velocity, with the resulting phase shifts interacting down the length of the transmission line. This effect will typically give a non-linear phase dispersion versus frequency and material changes. Full modelling of this structure is difficult, because it must be treated as a three-dimensional structure rather than a two dimensional structure. Moreover, the lossiness of the immediate environment of the stripline may determine whether propagation occurs predominantly in slow-wave or fast-wave mode.[16]

[16]Such interactions are discussed, e.g., in Neikirk et al., "Optically-Controlled Coplanar Waveguide Phase Shifters," in the December 1989 issue of MICROWAVE JOURNAL at page 77, which is hereby incorporated by reference. The structure described in that article is used for different purposes, but the analysis is of some help in understanding the operation of the planar probe described in the present application.

The transmission line is preferably nonresonant over the full range of frequencies of interest, although it may (less preferably) have resonances at other frequencies.

In one embodiment, such a probe is mounted on a standard flange for easy insertion into a process stream.

The dimensions of the probe are not particularly critical. The transmission line should preferably have an electrical length of at least several half-wavelengths, but can be made longer if higher sensitivity is desired.

Note that the probe does not include a large amount of structure nor electronics. Thus, for many applications, the probes can be discarded after each use.

The simplest substrate is simply fired high-density alumina (essentially $Al_2O_3$). This is commercially available, and is commonly used for microwave circuits (due to its desirable low-loss properties). This may be used bare, or with a passivating coating. Alternatively, the probe substrate can be assembled to a solid cover, such as low-density alumina, fired alumina, other ceramic materials, or even fiberglass.

The probe can be used "bare", i.e. with the leads exposed, if sufficiently inert metallization is used, e.g. gold or a self-passivating metallization such as stainless steel. Alternatively, a thin applied passivation layer can be used, such as plasma-deposited perfluorocarbon.

However, in alternative embodiments (as discussed below), substrates with other selective absorption properties can be used instead.

A significant advantage of the planar probe over the coaxial configurations previously discussed is that a very wide bandwidth can be used, even with materials of very high permittivity. This is because of the low loss and short length of the planar structure. Coaxial operation limits the frequency range which can be used, because the reduced diameter of the coaxial measurement section (necessary for operation at high frequencies) will cause significant pressure drop, and may cause precipitation and clogging in mixtures containing large volumes of particulates.

Among the disclosed inventions is provided a method for detecting the composition and microstructure of materials, comprising the steps of: providing a tunable oscillator which is connected to be pulled by the varying susceptance seen at a load connection thereto; connecting the load connection to the material under test through a single-ended probe which includes a substantially planar metal film structure which is patterned to provide a transmission line extending from the connection; and observing changes in the frequency of the oscillator.

Among the disclosed inventions is provided an electrical characterization system in which a single-ended planar probe, containing a transmission line of at least several half-wavelengths, is placed in proximity to a material to be characterized and is electrically coupled to a load-pulled voltage-controlled oscillator. The frequency response of the oscillator is then observed as the tuning voltage is varied.

Summary of the Invention—Tapered Probe

The present application discloses a probe which can be readily inserted into a variety of materials in solid, liquid, gas or plasma phase. This probe provides a "single-ended" coupling element which permits load-pull measurements to be made on an increased variety of materials.

A basic requirement of many applications is the need for measurement of materials having a wide range of dielectric constant ($\epsilon$ from 1 to 180) using a single transmission line section. This may create problems in launching the electromagnetic energy into a different dielectric medium. Without some help in making a graceful transition from one propagation medium to another (at a very different dielectric constant), the energy will simply be reflected.

The present disclosure teaches that a single-ended probe using a graded impedance (achieved by a planar tapered line or otherwise) can be particularly advantageous for coupling a load-pulled oscillator to a material system to be monitored. In alternate embodiments, such probes can also be used for RF sensing in other electrical configurations, using standard instrumentation in the microwave industry as a part of material characterization problems. Such embodiments are less preferable, but can still confer some of the advantages of the claimed inventions.

To solve this coupling problem, the disclosed inventions provide a tapered structure which performs an extended impedance transformation across a significant distance while coupled to the material under test. This solves the problem of coupling to the dielectric material. It also helps to solve the problems of lossy materials (such as salt water), where the lossiness of the material can make it difficult to obtain any usable signal at all.

However, it should be noted that, as the dielectric constant increases, the length appears shorter due to the rapid decrease of electrical length due to lower impedance. Thus, the physical length of a tapered probe may need to be longer than that of a corresponding straight probe.

The preferred approach to this is a "tapered planar" structure, i.e. a planar probe with a taper imposed on the trace geometries. An example of this is shown in FIG. 5B. This provides a compact single-ended probe which can be used for load-pull or other characterization of widely varying material streams.

Tapered lines have been used before for impedance matching in microwave circuits—see, e.g. U.S. Pat. Nos. 5,119,048 and 4,568,889, which are hereby incorporated by reference. However, the present disclosure teaches that tapered lines have substantial advantages for "single-ended" coupling to an unknown material, or as a general-purpose tool for coupling to a variety of materials with widely varying permittivity and loss characteristics. The prior uses of tapered lines were primarily for impedance matching between structures or between fixed dielectrics, and not for launching a wave into a varying dielectric stream. Some impedance matching structures have been used in slow wave structures, but again these are fixed situation matches and are not defined for large variable differences using the same structures. Similarly, transformation structures in waveguides are not fully analogous: A waveguide is operating for each mode with the frequency ranges where that mode is possible. The "wave impedance" concept provides a good analytical tool for such structures, but leads to some difficult analysis, since the wave impedance depends on the frequency of operation, the guide dimensions, and the mode. The actual wavelength in the guide is dependent on the cutoff frequency, but a coaxial line has a cutoff frequency of infinity.

Coaxial Structure with Tapered Sheath

An alternative embodiment provides a coaxial sampling chamber which includes a tapered dielectric sheath around the central rod at the point of fluid entry. This provides for a gradual interface charge and therefore will allow enough propagation to occur in high $\epsilon_n$ materials in order to give a measure of $\epsilon_n$.

In the initial launch point into the fluids the sheath material dominates the impedance function and vice versa at the other end. For low dielectric fluids and taper section, the occlusion of the fluids at the launch mediates the resultant dielectric constant of the cross section at that point to roughly that of the taper.

The tapered coaxial structure provides a significant fraction of a wavelength for the field pattern to conform to the new velocity and configuration. The impedance function then becomes a gradient which provides a transition from a 50 ohm system impedance to whatever the resultant impedance that the dielectric material in the coaxial section defines.

According to one alternative teaching, the transition section is electrically sufficient short (at the operating frequencies used) to prevent knees from ever occurring (no matter how high the $\epsilon_n$) will give a set of curves which are monotonic with $\epsilon_n$.

Among the disclosed inventions is provided a system for detecting the composition and microstructure of materials, comprising: an RF oscillator, which includes a gain element capable of providing substantial gain at frequencies greater than 100 MHz; a feedback path, coupling the output of the gain element to the input thereof, the feedback path including a tunable resonant circuit; an electromagnetic propagation structure which is RF-coupled to load the oscillator and in which electromagnetic wave propagation is electrically loaded by a portion of the material to be characterized, the propagation structure including a distributed impedance transformation section which includes at least one tapered element and which is itself also electrically loaded by proximity to a portion of the material; and circuitry connected to monitor the frequency of the oscillator to ascertain changes in the composition and/or microstructure of the material.

Among the disclosed inventions is provided a single-ended RF probe, for providing a bidirectional RF interface to unknown materials of widely varying permittivity, comprising: an external RF connection mechanically connected to a support structure; and a patterned and substantially planar conductive structure which is electrically connected to the connection and mechanically supported by the support structure; the conductive structure being shaped to provide a distributed impedance transformation section therein.

Among the disclosed inventions if provided a method for detecting the composition and microstructure of materials, comprising the steps of: providing a tunable oscillator which is connected to be pulled by the varying susceptance seen at a load connection thereto; connecting the load connection to the material under test through a single-ended probe which itself includes a distributed impedance transformation section which is itself electrically loaded by proximity to a portion of the material under test; tuning the oscillator over a range of frequencies; and observing changes in the frequency of the oscillator in response to the tuning step.

Among the disclosed inventions is provided an electrical characterization system in which a load-pulled voltage-controlled oscillator is coupled to a material to be characterized by a probe which contains a distributed impedance transformation section which includes at least one tapered element and which is electrically loaded by proximity to a portion of the material. The frequency response of the oscillator is then observed as the tuning voltage is varied.

Summary of the Invention—Probe with Selective Absorber

The present application discloses structures and methods for enhanced RF detection using chemically selective coatings on an RF probe. The disclosed inventions provide new methods for monitoring and characterization, using microwave energy, for use in the analysis of multiple component and bio-chemical systems.

Various electrode and chemical assay systems have been used in the past for specific measurements in organic systems. These methods were typically very slow and sensitive to operator and technique. Generally, most laboratories were forced to continue to rely on expensive and elaborate HPLC (High-Pressure Liquid Chromatography) and other primary type instrumentation for these measurements. This prevented rapid turnaround for process control.

The new technology disclosed herein can measure a vast list of specific organic species using immobilized enzymes, glucose in blood chemistry, lactic acid in muscle tissue, immunological tests, cancer cytology, and observation of catalytic action.

Additional special applications include moisture sensing of grains and bulk materials using a absorbing/desorbing ceramic material. This would make these measurements possible and simple even though the bulk material's packing density has prevented such measurements in the past. Since the material arrives at a specific level of moisture with its surroundings, the bulk density is not important.

An important part of this method are the materials used to place the microwave structure on. The substrate material can be anything which will support an electromagnetic field and have specific properties for a chemical structure. Examples include zeolites, ceramics with specific absorptions, doped semiconductors which increase/decrease their conductivity/dielectric constant with absorption. The use of enzymes embedded in a porous structure which are altered by selective substances may also be possible. This change in the enzyme structure would be visible with the load pull scheme. If a substrate was embedded or coated with a material which would deteriorate with selective absorption, the monitoring of the degradation would give rise to determination of the amount of the chemical present.

For another example, zirconia has unusual properties with oxygen at high temperatures. It forms a ion exchange with oxygen molecules which is used to measure oxygen content of gas streams especially in cars and stack emission monitoring. Use of this as a substrate could possibly have unique characteristic changes when the $O_2$ is present.

In the medical, food and pharmaceutical industries, it can be advantageous to implement this idea with throwaway substrates.

A particular advantage of the absorber-coated probe is that is can be designed to be self-calibrating. By contrast, other probes may need to be calibrated with a sample which is (or approximates) the material in question.

Humidity Sensing

The simplest application of selective absorption is for humidity sensing, e.g. using an absorber of low-density $Al_2O_3$ (alumina). Alumina will equilibrate to a moisture concentration which is exactly proportional (within a certain range) to the ambient humidity. (The interaction between alumina and water is typical of many materials, systems, where the relative equilibrium concentrations of a solute S in materials A and B are linearly related by a segregation coefficient $k=[S]_A/[S]_B$.)

However, the present invention does not require as much time as would be needed for equilibration. Instead, the rate of uptake of humidity by the absorber is differentially monitored, and this provides a fast measurement which also is related to the ambient humidity.

Note that the absorbent material need not be so readily reversible. For example, there is a vast literature on customizing zeolite structures to make "molecular sieves." However, the affinity of many such structures for their complementary substance is so high that the adsorbate is very tightly bound. Thus, a zeolite absorber may need to be periodically purged, or simply discarded when saturated.

In a further alternative embodiment, where an active matrix material such as a zeolite is to be used for moisture measurement in grains and food solids, a "zip open" sealed bag can be useful for field use.

Among the disclosed inventions is provided a system for detecting the composition and microstructure of materials, comprising: an oscillator, which includes a gain element capable of providing substantial gain at frequencies greater than 100 MHz, and a feedback path, coupling an output of the gain element to an input thereof, the feedback path including a tunable resonant circuit; and an electromagnetic propagation structure which is RF-coupled to load the oscillator and in which electromagnetic wave propagation is electrically loaded by a portion of the material to be characterized, the propagation structure being mechanically connected to a selective absorption material, which is selective to preferentially absorb a predetermined target species, and electrically configured to provide efficient capacitive coupling to the propagation structure; and circuitry connected to monitor the frequency of the oscillator to ascertain changes in the composition or microstructure of the material.

Among the disclosed inventions is provided a single-ended RF probe, for providing a bidirectional RF interface over a range including at least one predetermined operating frequency, to detect the presence of at least one target species in a quantity of material, comprising: an external RF connection mechanically connected to a support structure; and a conductive structure which is electrically connected to the external connection and mechanically supported by the support structure, and which provides a transmission line extending from the external connection; and a selective absorption material, which is selective to preferentially absorb a predetermined target species, and which is mechanically connected to the support structure in a relation which provides efficient capacitive coupling to the selective transmission line.

Among the disclosed inventions is provided a method for detecting the composition and microstructure of materials, comprising the steps of: providing a tunable oscillator which is connected to be pulled by the varying susceptance seen at a load connection thereto; connecting the load connection to the material under test through a single-ended probe which includes a substantially planar metal film structure which is patterned to provide a transmission line extending from the external connection, and which also includes a selective absorption material, which is selective to preferentially absorb a predetermined target species, and which is mechanically affixed to the probe to provide efficient capacitive coupling to the transmission line; and observing changes in the frequency of the oscillator.

Among the disclosed inventions is provided an electrical characterization system in which a single-ended planar probe, containing a transmission line of at least several half-wavelengths and a selective absorption material to which a species of interest will segregate, is placed in contact with a material to be characterized, and is also electrically coupled to a load-pulled oscillator.

Summary of the Invention—Probe with Integrated Heater

A further embodiment provides an RF probe which not only includes a selective-absorbing material (such as alumina), but also includes a heater for causing desorption of the absorbed material. This permits the heater to be "cycled" efficiently.

This could be embedded in the ground plane or placed on the backside of the substrate. This heater would be activated at either a set value of frequency change or at time intervals. During the on cycle the change in the material can be simultaneously monitored by the same load pulled oscillator to determine when the regeneration point has been reached or to indicate to an operator that the time to replace the probe and material has arrived.

This embodiment also permits some aggressive absorbing materials (such as high-affinity zeolites) to be used for selective absorption.

This embodiment is particularly attractive for field measurement of humidity, but can also be used for measurement of other substances.

In some applications, this heater can also be used to provide temperature regulation of the probe's immediate environment, if the material under test would not provide a heavy thermal load. For example, this may be useful where the sample is gaseous and of variable temperature.

In the presently preferred embodiment, separate leads are provided to power a resistive heater in a planar structure. However, in an alternative embodiment a resistive heater can be driven by a DC component on the coaxial line (if the power detection diode is not used). In this embodiment, an isolating inductance can be used with the heater to avoid resonances.

During each absorption cycle, the rate of uptake can be measured using time-differentiated measurements. An integral is accumulated to provide an index of the total loading of the absorber. The relation between this integral and the rate of uptake provides an index of the ambient concentration. When the integral exceeds a certain threshold, this indicates that the absorber is becoming fully loaded. The heater is then activated to refresh the absorber and start the cycle again.

Among the disclosed inventions is provided a system for detecting the composition and microstructure of materials, comprising: an oscillator, which includes a gain element capable of providing substantial gain at frequencies greater than 100 MHz, and a feedback path, coupling an output of the gain element to an input thereof, the feedback path including a tunable resonant circuit; and an electromagnetic propagation structure which is RF-coupled to load the oscillator and in which electromagnetic wave propagation is electrically loaded by a portion of the material to be characterized, the propagation structure being mechanically connected to a selective absorption material, which is selective to preferentially absorb a predetermined target species, and electrically configured to provide efficient capacitive coupling to the propagation structure, and also a heater integrated with the propagation structure in a common package; and circuitry connected to monitor the frequency of the oscillator to ascertain changes in the composition or microstructure of the material, and to activate the heater relatively which the absorption material has become loaded.

Among the disclosed inventions is provided a single-ended RF probe, for providing a bidirectional RF interface over a range including at least one predetermined operating frequency, to detect the presence of at least one target species in a quantity of material, comprising: an external RF connection mechanically connected to a support structure; a conductive structure which is electrically connected to the external connection and mechanically supported by the support structure, and which provides a transmission line attending from the external connection; and a resistive heater which is mechanically supported by the support structure, and connected to receive a drive current; and a selective absorption material, which is relative to preferentially absorb a predetermined target species, and which is mechanically connected to the support structure in a relation which provides efficient capacitive to the transmission line.

Among the disclosed inventions is provided a method for detecting the composition of materials, comprising the steps of: providing a tunable oscillator which is connected to be pulled by the varying susceptance seen at a load connection thereon; the load connection to the material under test through a single-ended probe which includes connecting the load concoction to the material under test through a single-ended probe which includes a conductive structure which is patterned to provide a transmission line extending from the external connection, and which also includes a relative absorption material, which is selective to preferentially absorb a predetermined target species and which a mechanically affixed to the probe to provide efficient capacitive coupling to the transmission line, and a resistive heater which is integrated with the probe; and observing time-dependent changes in the frequency of the oscillator to detect the rate of uptake of the target species and the cumulative loading of the absorber, and activating the heater, whenever the absorber becomes excessively loaded, to cause description of the target species.

Among the disclosed inventions is provided a single-ended RF probe which contains: a transmission line of at least several half-wavelengths; a selective absorption material to which a species of intact sill segregate; and a resistive heater, all integrated into a common mechanical structure. The heater can be used to "unload" absorption material, by driving off the target species from it. This is particularly useful for humidity measurement.

Summary of the Invention—Monitoring Fermentation

The present discloses processes for monitoring bulk fermentation, and for partially characterizing the composition of a batch fermentation, by observing the frequency of a load-pull oscillator which is RF-coupled to the material under test (preferably by a simple single-ended RF probe).

Most pharmaceutical fermentations ate done in a small batch mode where there is no flow. The planar probe structure is very conducive to the application. The plane structure also lends itself to throw away replacements to maintain sensitivities and prevent bacteriological growth in these sensitive vats. Of course, sterile load-lock procedures are preferably used for insertion of a sterile RF probe into a culture vat.

It should be noted that the disclosed methods are not only useful for pharmaceutical applications, but may also be useful in brewing, winemaking, and in food industry processes using biologically active agents.

The disclosed methods also permit the biomass of a fluid strain to be measured. Thus metering of a starter culture can be optimized without waste.

The disclosed methods also provide a direct test for yeast viability in solution. Thus the presence of yeast activity can be checked during the early stages of fermentation, before the yeast mass has multiplied sufficiently to be unmistakably active.

Among the disclosed inventions is provided a method for monitoring the status of a fermentation process, comprising the steps of: introducing selected active microorganisms into an aqueous solution containing nutrient substance, and isolating the solution in a substantially sterile vat; electromagnetically coupling a RF probe to the solution in the vat, and connecting the probe to load an oscillator operating at more than 100 MHz, with no RF buffer stage being interposed between the oscillator and the probe; and observing time-dependent changes in the frequency behavior of the oscillator, to indicate change in the composition of the solution.

Among the disclosed inventions is provided a method for initiating a fermentation process, comprising the steps of: introducing related active microorganisms from a starter culture into a nutrient solution, while also monitoring the flow rate of the introducing step and monitoring the frequency of an RF oscillator which is connected to the starter culture through a RF probe which is electromagnetically coupled by proximity to be loaded by the starter culture, with no RF buffer stage being interposed between the oscillator and the probe; and terminating the flow to provide a desired total biomass transferred from the starter culture into the nutrient solution.

Among the disclosed inventions is provided a method for monitoring bulk fermentation, and for partially characterizing the composition of a batch fermentation, by observing the frequency of a load-pull oscillator which is RF-coupled to the material under test (preferably by a simple single-ended RF probe).

Summary of the Invention—Monitoring Curing/Crystallization

The present application discloses process for monitoring the state of curing (or microcrystalline change) of solid materials, by observing the frequency of a load-pull oscillator which is RF-coupled to the material under test (preferably by a simple single-ended RF probe).

One area where this technique is of particular interest is in monitoring the curing of shaped aerodynamic composite materials.

Another area of particular interest is in monitoring the curing of concrete and cement compositions. Cement curing in a complex process which requires a fairly extended period.

In curing Portland cement (and related compounds), it is generally desirable not to cure too rapidly. Dendritic crystallite growth occurs during the normal curing process, and the interpenetration and interlocking of the resulting crystallites gives the final material its strength. If curing is performed too rapidly, this interpenetration will not occur, and the material will be weaker.

Where it is required merely to detect the endpoint of a curing process, a useful alternative is to use rate-of-change measurements instead of (or in combination with) absolute measurement.

Background: Laid-Up Composite Materials

High performance fiber-reinforced plastic composites are assembled from single-ply unidirectional tape, e.g. of E-glass-epoxy S-glass-epoxy, Kevlar 49-epoxy, high strength carbon-epoxy, high modules carbon-epoxy, or boron-epoxy. These have highly anisotropic strength, so that multiple layers of such tape are normally combined to achieve a finished structure with adequate strength for its specification.

To manufacture assembled pieces, sheets of prepreg tape (i.e. tape impregnated with bonding agent) are stacked in a specified orientation and then cured under pressure to fabricate a component. The prepreg, tape may be cut and laid up by hand or by automated tape laying machines. The layup is covered with release fabric over which breather plies are placed to provide a path for removal of entrapped air. A vacuum bag is placed over the breather plies and the edges are sealed. The entire assembly is placed in an autoclave.

Polybutadiene, vinyl ester polymers, and polyimide are thermosetting matrix materials are all used in fibs reinforced plastics; but the most popular choice of matrix material for high performance composites containing carboy fibers has been epoxy. (Any molecule that contains the oxirane group in called an epoxy; the backbone of a particular epoxy resin may be built on aromatic and/or aliphatic groups.) Amine or anhydride agents are used to cure epoxy resins. Curing can be achieved at lower temperatures with the amine agents; anhydride curing agents offer increased thermal stability and moisture resistance. Accelerators such as baron trifluoride or benzyldimethylamine (BDMA) are often used to speed up the cure of epoxies.

Nondestructive inspection is normally necessary. Composite components must be inspected to ensure the absence of defects. Microcracks, delaminations, and voids are the most common typo of flaws, and ultrasonic inspection is the moat popular method for their detection. One method is ultrasonic C-scan. Other conventional nondestructive inspection methods include visual, sonic, radiography, microwave, infrared, holography, and eddy current.

Among the disclosed inventions is provided a method for monitoring the state of curing (or microcrystalline change) of solid materials, comprising the steps of combining precursor components to provide a body having a desired physical shape; electromagnetically coupling a single-ended RF probe to the body, and connecting the probe to load an oscillator operating at more than 100 MHz, with no RF buffer stage being interposed between the oscillator and the probe; and observing time-dependent change in the frequency behavior of the oscillator, to detect changer in the composition and/or microcrystalline structure of the body.

Among the disclosed inventions is provided a method for controlling a process of curing a predetermined solid materiel, comprising the steps of combining precursor components to provide a body of the materiel; electromagnetically coupling a single-ended RF probe to the body, and connecting the probe to load am oscillator operating at more than 100 MHz, with no RF buffer stage being interposed between the oscillator end the probe; and observing time-dependent changes in the frequency behavior of the oscillator, to detect changes in the composition and/or microcrystalline structure of the body.

Among the disclosed inventions is provided a method far monitoring the state of curing (or microcrystalline change) of solid materials, by observing the frequency of a load-pull oscillator which is RF-coupled to the material under test (preferably by a simple single-ended RF probe).

Summary of the Invention—Monitoring Food Composition and Process Stage of Food Materials The present application discloses processes for monitoring the state of processing of, and for partially characterizing the composition of, food and feed produce, by observing the frequency of a load-pull oscillator which in RF-coupled to the material under test (preferably by a simple single-ended RF probe).

Conventional process control in the food industries is almost entirely off-line (using laboratories to test samples). On-line controls are ordinarily limited to temperature, flow meters, viscosity, and mass (weighing systems). Processes are usually "recipes" of weights, times, and temperatures. This is because foodstuffs are chemically very complex, so that conventional high-tech methods (such as chromatographs and near IR spectroscopy) are not usually an adaptable to on line process control as in the "regular chemical" industry. The materials are molecularly too complex.

Therefore, laboratory analysis must be used to measure (or infer) a process condition. Items as carbohydrate, fats, protein fiber content, ash content, mineral content are done by conventional "wet" analysis. These lab methods are usually 1. Refractometry
2. Photoelectric Colorimetry
3. Some spectrophotometry
4. Some polarimetry
5. Melting/softening points
6. Viscometry
7. Conductivity
8. Some Chromatography
9. Titrations
10. Mass/Loss gravimetric methods
11. Solvent extractions techniques Sometimes these are indirect measurements. For example, viscosity may be used to infer water content or gelatinization of starch (cooking). Water content of various components is a major item of interest/control. This in usually measured by heating a sample and measuring the weight loss. Color is used to determine proper corking times for caramelization of starch/flour products.

By contrast, the disclosed methods permit direct real-time measurement of the molecular changes.

In one aspect of this, melting and softening can be measured directly, and correction with temperature will then give an indirect measurements of process states.

Given a generally known process flow, the present invention provides new methods for monitoring the composition of the flow. For example, the disclosed inventions permit real-time non-contaminating measurement of water content, or for contort, or both in a stream of ingredients or in a stream of processed food products.

Given a generally known process flow, the present invention also provides new methods for monitoring the degree of cooking of the flow. As the following results show, the molecular changes in starches which are caused by cooking can be directly detected, and the molecular changes in meats which are caused by cooking can also be directly detected. This provides efficient endpoint detection for food processing.

The simplest way to use this monitoring technique analytically in to look at the time derivative of the measured RF frequencies: a certain percentage decrease in the rate of change can be used for an endpoint signal, to terminate a batch stages (Of course, this percentage decrease would be customized for a particular process, and would allow for continued cooking as the temperature of the food materials is ramped down.)

Among the disclosed inventions is provided a method far processing food and analogous materials, comprising the steps of: providing multiple flows of ingredient materials; electromagnetically coupling a single-ended RF probe to at least one the flow of ingredient materials, the probe being electrically connected to load a free-running RF oscillator, with no RF buffer stages being interposed between the oscillator and the probe; and observing the frequency behavior of the oscillator, to detect variation in the composition of the respective flow of ingredient materials; dynamically controlling the flows of the materials in accordance with results of the observing step; and combining and processing the flows of ingredient material to provide a food product.

Among the disclosed inventions is provided a method for drying organic materials, comprising the steps of: providing a flow of a material which varies in water content; electromagnetically coupling a RF probe to the flow, the probe being electrically connected to load a free-running RF oscillator, with no RF buffer stages being interposed between the oscillator and the probe; observing the frequency behavior of the oscillator, to detect the moisture content of the flow; and adding water w the flow whenever the observing step indicates that the moisture content of the flow is below a target level; and drying the flow is a dryer stages whereby the moisture content of the flow is dynamically controlled to be high enough to prevent clogging of the dryer, but no higher than necessary for reliable operation.

Among the disclosed inventions is provided a method for cooking food and analogous materials, comprising the steps of: introducing a mixture of predetermined ingredients into a cooking vessel; applying heat to the vessel in a controlled temperature-versus-time relationship, to cook the mixture: electromagnetically coupling a RF probe to the mixture in the vessel, and connecting the probe to load as oscillator operating at more than 100 MHz with no RF buffer stage being interposed between the oscillator and the probe; observing the frequency behavior of the oscillator to detect changes in the molecular composition and/or conformation of the mixture; and unloading the vat at a time which is at least partially determined by the results of the observing step.

Among the disclosed inventions is provided a methods for monitoring the state of processing of, and for partially characterizing the composition of, food and feed products, by observing the frequency of a load-pull oscillator which is RF-coupled to the material under test (preferably by a simple single-ended RF probe).

Summary of the Invention—Patch Probe

In many applications the avoidance of direct contact with the materials under test is overwhelmingly desirable, to prevent contamination.

The present application discloses a noninvasive RF probe which can be readily coupled, through a dielectric window, to a material under test. This probe provides a "single-ended" isolated-coupling element which permits load-pull measurements to be made on an increased variety of materials. The electrical configuration of this probe in like that of a patch antenna,[17] and hence this probe mass be referred to a "patch probe". The patch probe is inherently less sensitive than a probe which is directly immersed is a inserted into the material under test, but mass be sufficiently sensitive for many applications.

[17]Microwave antennas of such configuration are believed to have been used for heating but apparently not for characterization.

A planar probe an also be used for coupling through a window. In this case the planar probe would be placed flat against the window. However, the patch probe is preferred for such applications.

Among the disclosed inventions is provided a system for detecting the composition and microstructure of materials, comprising: an oscillator which includes a gain element capable of providing substantial gain a frequencies greater than 100 MHz, and a feedback path, coupling no output of the gain element to an input thereof, the feedback path including a tunable resonant circuit and a patch antenna which in RF-coupled to load the oscillator and which is placed in proximity to a portion of the material to be characterized so that electromagnetic wave propagation in the antenna is electrically loaded thereby; and circuitry connected to monitor the frequency of the oscillator to ascertain changes in the composition or microstructure of the material Among the disclosed inventions is provided a method for detecting the composition and microstructure of materials, comprising the steps of providing a free-running oscillator which is connected to be pulled by the varying susceptance seen at a load connection thereto; connecting the load connection to the material under test through a path antenna which is RF-coupled to load the oscillator and which is placed in proximity to a portion of the material to be characterized so that electromagnetic wave propagation in the antenna is electrically loaded thereby; and observing changes in the frequency of the oscillator.

Among the disclosed inventions is provided an electrical characterization system in which a patch antenna, used as a single-ended RF probe, is placed sufficiently close to a material under test to achieve near-field coupling thereto, and is also electrically coupled to a load-pulled oscillator.

Summary of the Invention—Load-Pull Analysis Method

The present application discloses a method for rapidly analyzing the state of a given process. A load-pulled oscillator is coupled to the material under test, and is swept across a range of frequencies. The oscillator frequency is swept, for example, by sweeping a tuning voltage, applied to a varactor in the oscillator circuits, across a predetermined range. The oscillator is coupled to the material undo test by a probe which is electrically long (preferably at least several half-wavelengths when fully loaded by the material under test). The specific conditions (probe type, physical conditions of coupling, and range of tuning voltages or frequencies) will all have been previously defined, using the various considerations set forth in detail below. The oscillator frequency is monitored while the tuning voltage is swept in a predetermined direction (up rather than down, for example.

For this defined set of conditions, each sweep of the tuning voltage $V_{tun}$ will produce a corresponding range of oscillator frequency value $f_{OSC}$. By integrating $f_{OSC}$ the predetermined range of $V_{tun}$, a single derived index number results. This turns out to be very useful in characterizing a given process under a given set of conditions.

Part of the reason for this is that shifts in material composition which product even very small shifts in permitivity will have the effect of shifting the "knees" in the frequency curve. These knees, which are readily visible is plots of oscillator frequency as a function of tuning voltage, correspond to points where the oscillator phase goes though a 180° transition. When this occurs, the oscillator will return to its original operating frequency, and this frequency is likely to shift.

In a typical application the oscillator's basic frequency can be forced to change by the inclusion of a varactor (a voltage variable capacitor) in the primary resonant loop of the circuit. By applying a DC voltage on this varactor, many oscillators can be tuned over an octave band. In the description above, the oscillator and load pull performance was assuming a fixed frequency (no varactor) circuit. If the load was a fixed length of lossless transmission line and the oscillator frequency was forced by the applied voltage on the varactor as opposed to the load pull phenomena, the "knees" would be seen as the phase seen at the oscillator was swept through 180° because of the effect of decreased wavelengths at higher frequencies. The number of knees appearing in the voltage vs frequency plot is dependent upon the dielectric constant of the medium in the transmission line, the length of the line and the frequency.

Thus, simple data reduction can be performed to derive a single index number for a given set of condition. This is particularly useful where a gives system is being tracked over time, since the time-domain behavior of the index number can easily be tracked. Thus, for instance, for end-point detection in monitoring a batch process, the endpoint can be identified when the index value has shifted by a certain percentage from its initial value and the rate of change has declined to a certain percentage of its maximum value during the process run.

Among the disclosed inventions is provided a method for controlling a process, comprising the steps of providing a voltage-controlled oscillator which a connected to be pulled by the varying susceptance seen as a load connection thereto, and which is connected to be tuned by a tuning voltage applied thereto; connecting the load connection to an RF interface which is electrically loaded by proximity to material undergoing the process; sweeping the tuning voltage across a predetermined range of voltages; integrating the oscillation frequency of the oscillator, as a function of tuning voltage, across the range of voltages, to provide a process index value; comparing the process index value with a known range of values for comparable process conditions; and taking action conditionally, within the process, in dependence on the result of the comparing step.

Among the disclosed invention is provided a process control method, wherein a load-pulled voltage-controlled oscillator is coupled through an RF probe, without isolation, to a material in the process. The frequency response of the oscillator is then integrated over voltage, as the tuning voltage is varied across a predetermined range. This integral gives a single "process index" value which is then used as a basis for conditional action on the process.

Summary of the Invention—Switchable Probe

A further disclosed innovation is a single-ended probe which includes multiple transmission line segments, and which also includes an RF switching element connected to permit switching between the two segments.

If an RF switch (pin diodes) was used on the substrate to switch between two lines, one could be an uncovered metal trace and the other could be a covered metal section with the covering being relative to a particular chemical. This combination would provide a measurement of a specific substance using the covered side of the probe, and once this component of the material under study is known as additional component could be derived from the response from the bare side of the probe. For example if the covered side was of the material to discern glucose in a dextrose/glucose/water mixture, the bare side's additional information would provide far a solution to how much water was in the mixture.

This can also be used to provide spatially-resolved differential measurement for detection of spatially-varying characteristics (e.g. material zone boundaries in a distillation or chromatographic column).

Among the disclosed inventions is provided a system for detecting the composition and microstructure of materials, comprising: an oscillator, which includes a gain element capable of providing substantial gain at frequencies greater then 100 MHz, and a feedback path, coupling an output of the gain element to an input thereof the feedback pads including a tunable resonant circuit; and an electromagnetic propagation structure which is RF-coupled to load the oscillator and which includes an RF switch and first and second transmission line structures, the switch being connected and configured to connect the first transmission line structure to the external connection relatively undo remote command; at least one of the transmission line structures being positioned so that electromagnetic wave propagation thereon can be electrically loaded by proximity to a portion of the material to be characterized; and circuitry connected to monitor the frequency of the oscillate to ascertain changes in the composition or microstructure of the material.

Among the disclosed inventions is provided a single-ended RF probe, for providing a bidirectional RF interface to materials to be characterized, comprising: an external RF connection mechanically connected to a dielectric support structure; and an RF switch mounted on the support structure and electrically connected to the external connection; and first and second transmission line structure, each connected to the switch and mounted on the support structure; wherein the switch a connected and configured to connect the first transmission line structure to the external connection selectively, in accordance with a bias signal received at the external connection.

Among the disclosed inventions is provided a method for detecting the composition and microstructure of materials, comprising the steps of: providing a tunable oscillator which is connected to be pulled by the varying susceptance seen at a load connection thereto; connecting the load connecting to the material under test through a single-ended probe which include an RF switch and first and second transmission line structures, the switch being connected and configured to connect the first transmission line structure to the external connection relatively undo remote command; positioning the probe so that at last one of the transmission line structure is electrically loaded by proximity to a portion of the material to be characterized; and observing changes in the frequency of the oscillator, while switching the RF switch to activate the first and second transmission line alternately.

Among the disclosed invention is provided a single-ended RF probe which contains an RF switch, and TWO transmission lines, all integrated into a common mechanical structure The two transmission lines can both be capacitively loaded by inserting the mechanical structure into a material under test, but the two lines have different coupling characteristics. (For example, one line may be coated with a relative absorption material; or the two lines may merely be spatially separate.) Remote sensing electronics, such as a load-pulled oscillator, thus have an electrical interface through which to detest changes corresponding to the properties of the material under test. The RF switch permits additional information to be gained by switching between the two transmission lines.

BRIEF DESCRIPTION OF THE DRAWING

The present invention will be described with reference to the accompanying drawings, which show important sample embodiments of the invention and which are incorporated in the specification hereof by reference, wherein:

FIGS. 1A1 and 1A2 show a planar probe for use with a load-pulled oscillator system. FIGS. 1B1 and 1B2 show a modification of the planar probe of FIG. 1, wherein an impedance transformer is included.

FIGS. 2A1 and 2A2 show a planar probe with a terminating element FIG. 2B1 shows a detail view of the attachment of a resistor terminating element in the probe of FIG. 2A. FIG. 2B2 shows a detail view of the attachment of a short-circuit terminating element in the probe of FIG. 2A. FIGS. 2B3 shows a detail view of the attachment of a capacitor terminating element in the probe of FIG. 2A. FIG. 2B4 shows a detail view of the attachment of an inductor terminating element in the probe of FIG. 2A. FIG. 2B5 shows a detail view of the attachment of a diode terminating element in the probe of FIG. 2A.

FIGS. 4B1 and 4B2 show a planar probe with beads affixed thereto, for chemically relative signal enhancement.

FIGS. 4E1 and 4E2 show a planer probe with TWO transmission lines (only one of them overlain by an added relative absorption layer), and an RF switch to select which of the two transmission lira will be active.

FIG. 7A1 and 7A2 show two views of a first sample embodiment of a patch antenna, for coupling through a dielectric wall (or window) to electrically monitor the contents of a vessel or process flow. FIGS. 7B1 and 7B2 show two views of a second patch antenna embodiment, which also cm be used for monitoring materials through a dielectric wall.

DESCRIPTION OF THE PREFERRED EMBODIMENTS

The numerous innovative teachings of the present application will be described with particular reference to the presently preferred embodiment. However, it should be understood that this class of embodiments provides only a few examples of the many advantageous uses of the innovative teachings herein. In general, statements made in the specification of the present application do not necessarily delimit any of the various claimed inventions. Moreover, some statements may apply to some inventive features but not to others.

Measurement System

Figure 10:
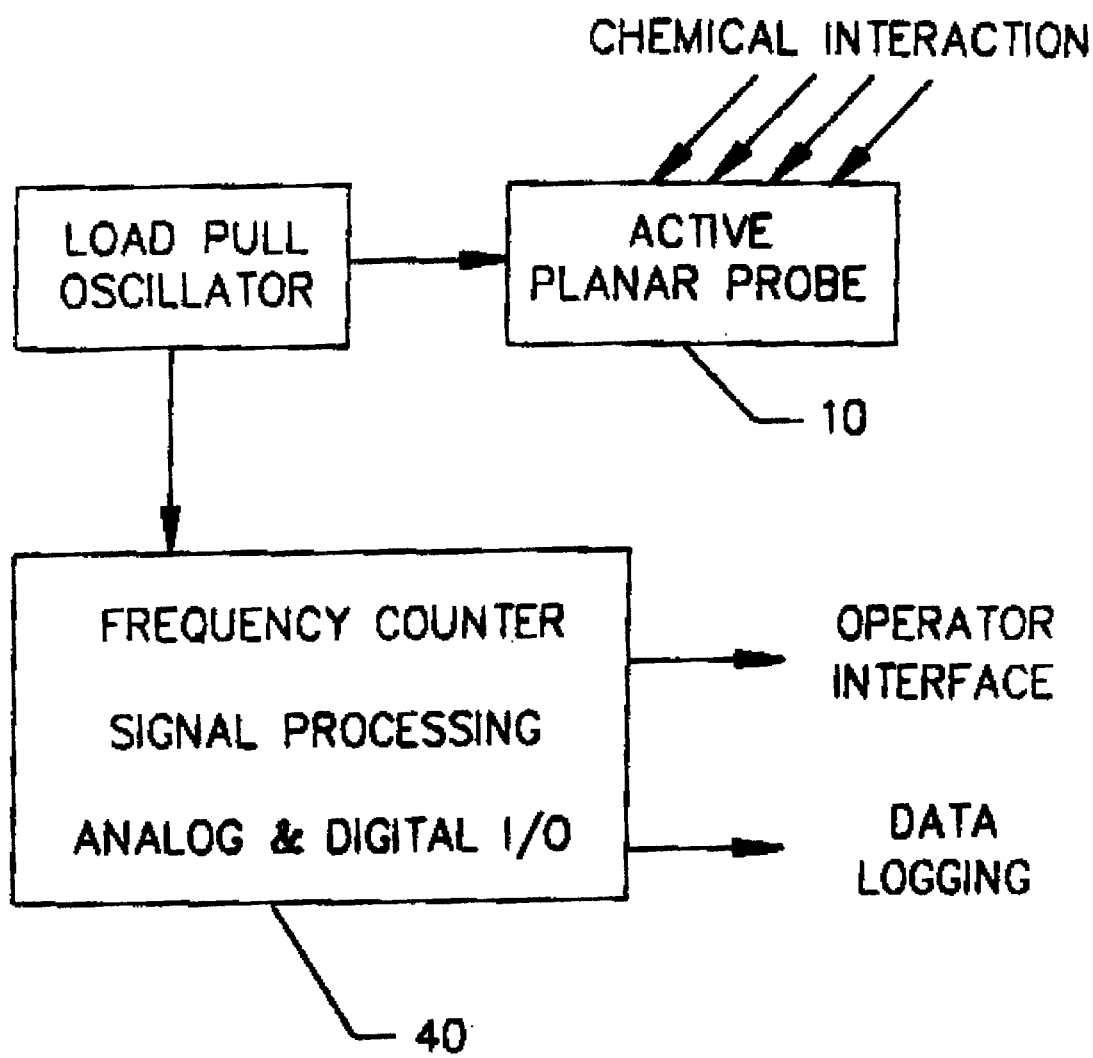
FIG. 10 schematically shows the configure of a complete system for implementing the disclosed invention

FIG. 10 schematically shows the configuration of a complete system for implementing the disclosed inventions. The chemical system under measurement interacts with the active planar probe 10 and produces a shift in the frequency of operation of the load pull oscillator 30. The frequency counter portion of the support electronics 40 accepts the oscillator's output, counts the number of zero crossings during a fixed time interval, and provides the information to the signal processing section. The frequency of the oscillator 30 is computed by the processing section. This frequency is then used is a polynomial equation subtracted from a fixed numerical value, to obtain a process value. The analog and digital I/O sections of electronics 40 can receive commands from the processing cation and output analog or digital signals based on this process value. The operator interface provides the operator with the means to change the polynomial or fixed numerical valve, to set alarms and relay closing values and to range the output. Data logging can be obtained through a digital interface for connection to a PC.

Electrical Configuration

Figure 9:
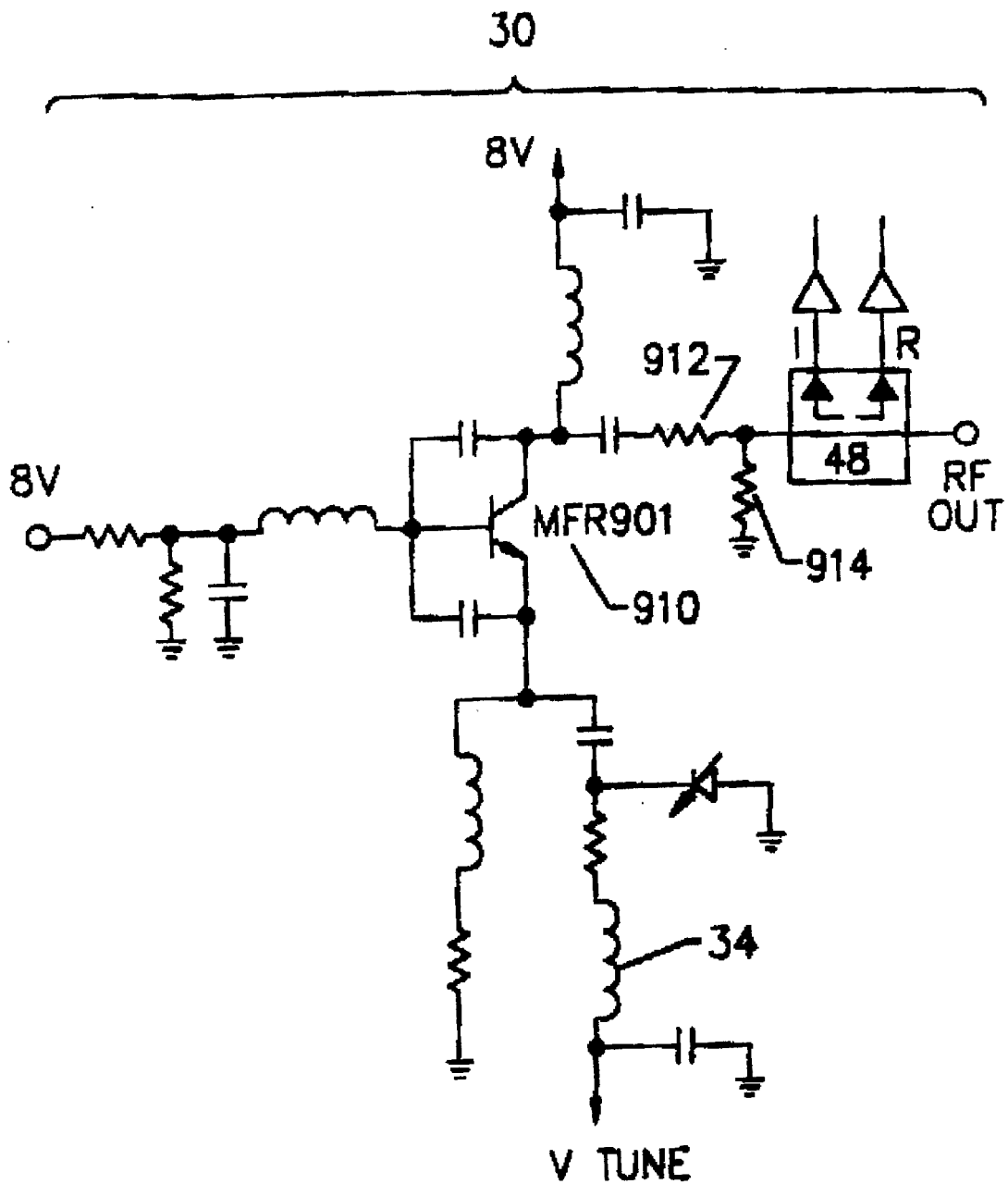
FIG. 9 schematically shows the electrical configuration used is the presently preferred embodiment of the inventions.

FIG. 9 schematically shows the electrical configuration used to implement the oscillator in the presently preferred embodiments of the inventions. The load seen at line RFOUT (presented by the measurement section 800) is connected to the collector of driver transistor 910, while the tank circuit 34 is connected into the emitter-base coupling of driver transistor 910. The directional coupler 48 is a dual directional coupler which is connected directly on the line RFOUT.

Note that a small series resistor 912 is used in the RFOUT line. (In the presently preferred embodiment, the value of this component is 9 Ω) This resistor helps to prevent spectral breakup (by suppressing oscillation at secondary frequencies).

A shunt resistor 914 is alto attached to the RFOUT line This resistor also adds to stability, by fixing a maximum magnitude for the impedance seen at line RFOUT. (In the presently preferred embodiment, the value of this component is 562 Ω)

These two resistors will reduce the magnitude of the frequency hops seen, as discussed above.

The directional couple preferably diverts only 1% of the reflected power, so that the load is still coupled closely enough to be able to pull the oscillate, the corresponding output from coupler 48 is connected to a frequency counter and control logic, as described above. Also, the two outputs from the directional coupler are used to measure inserted power and reflected power.

Planar Probes

The present application discloses a planar probe which can be readily inserted into a variety of materials in solid, liquid, gas or plasma phase. This prove provides a "single-ended" coupling element which permits load pull measurements to be made on an increased variety of materials. As with the coaxial configuration, oscillator frequency can be monitored directly, or in combination with insertion loss.

FIG. 1A1 and 1A2 shows a planar probe for the with a load pulled oscillator system. This probe contains a simple stripline structure, with a central strip 21 coupled to the central wire 22 of the coaxial input, and a surrounding place coupled to the shielding of the coaxial input. This provides a simple constant-impedance transmission line structure.

Figure 6:
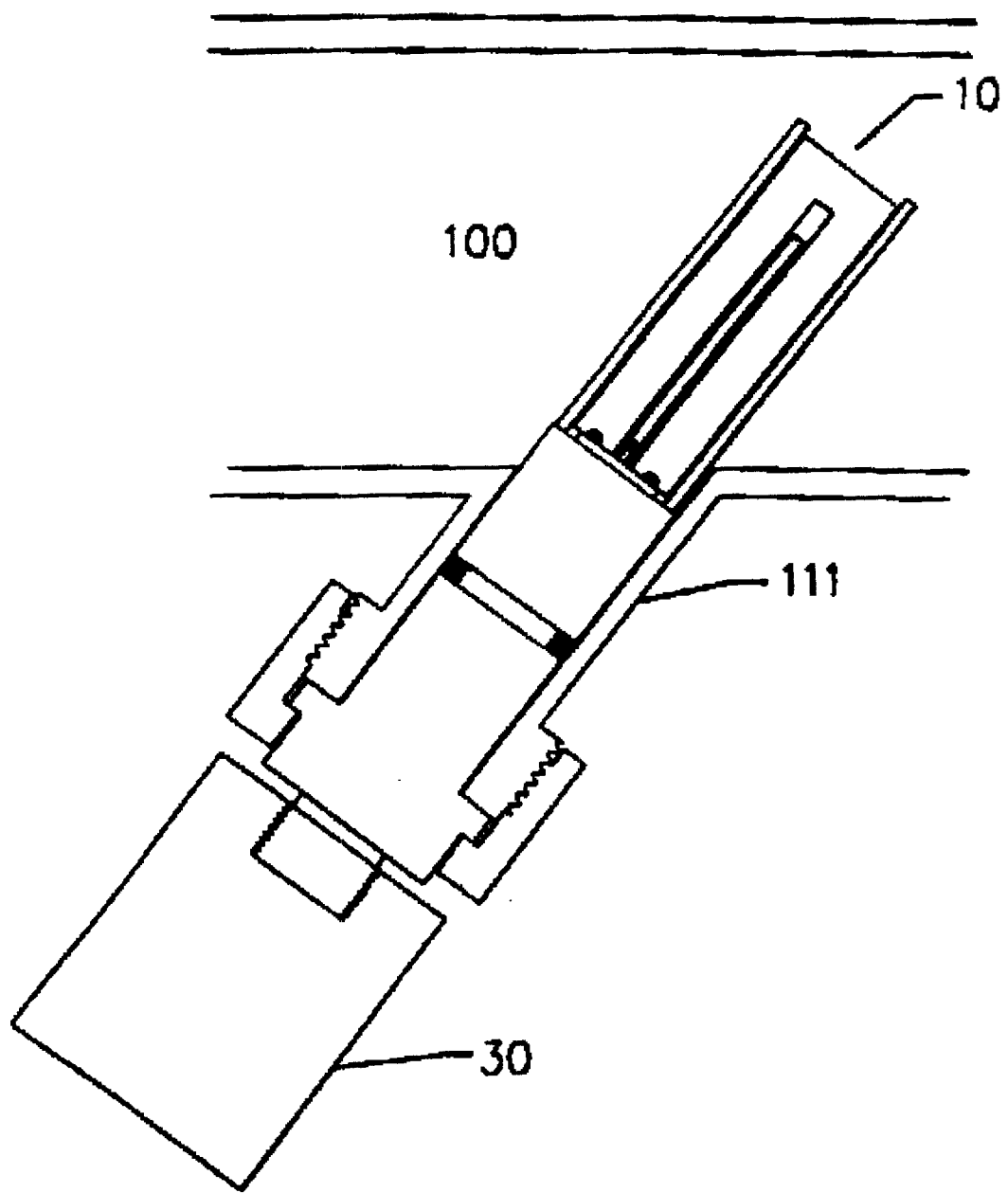
FIG. 6 shows an example of mounting a planar probe to monitor the electrical characteristic of a fluid stream or a vessel.

In a sample embodiment, the central strip 21 is 0.08" wide, and it is separated from the adjacent plane 23 on either edge by a 0.03" gap. The overall dimensions of the substrate 24 are 0.75" by 2.375", and the strip 21 is about 2" long. However, of course these numbers are merely illustrative, and can be readily varied. As will be recognized by microwave engineers, the dimensions should be related to maintain an impedance match to the incoming line (which is a standard 50 Ωcoax, in the presently preferred embodiment). This small structure permits ready insertion into fluid streams; FIG. 6 shows an example of mounting a planar probe 10 (like probe 11 of FIG. 1, or modified as described below) on a standard flange for easy insertion into a process stream 100. In some applications it may be advantageous to position the probe 10 so that its ground place occupies the portion of the sensor which might be exposed to interferences to measurement, such as particles or gas bubbles.

Figure 2C:
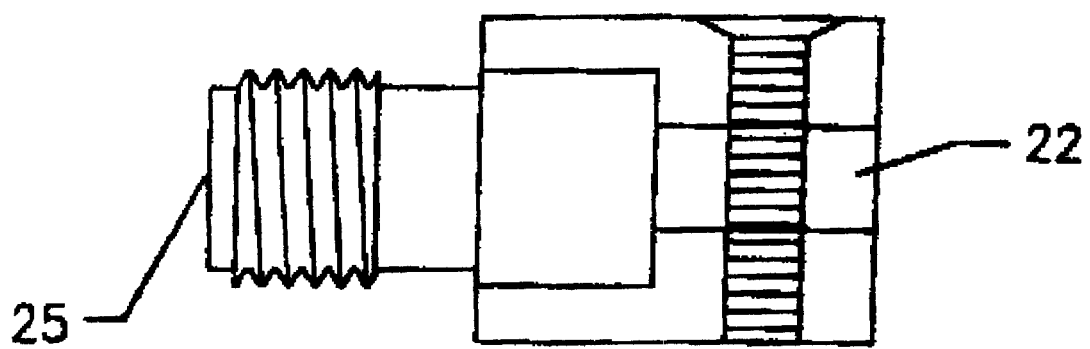
FIG. 2C shown a detail view of the attachment of the probe of FIG. 2A to a coaxial connector.

A standard coaxial connector 25 is used, in the presently preferred embodiment, but of course other connectors can be used (or a coaxial line as be soldered directly to the probe). FIG. 2C shows a detail view of the attachment of the probe of FIG. 2A to a coaxial connector, is a sample preferred embodiment.

The transmission line does not necessarily have to end in an open, as in the embodiment of FIG. 1A. Termination of this transmission line can be accomplished in several ways. FIG. 2A shows a planar probe 12 with a terminating element 26. The chip termination 26 can be a resistor, capacitor, inductor, short, or diode. FIG. 2B1 shows a detail view of the attachment of a resistor terminating element 26A is the probe of FIG. 2A FIG. 2B2 shows a detail view of a short-circuit termination 26B in the probe of FIG. 2A FIG. 2B3 shows a detail view of the attachment of a capacitor terminating element 26C in the probe of FIG. 2A. FIG. 2B4 shows a detail view of the attachment of an inductor terminating element 26D in the probe of FIG. 2A. FIG. 2B5 shows a detail view of the attachment of a diode terminating element 26E in the probe of FIG. 2A.

Selection of one of these terminations can be made in accordance with the needs for measurement of particular materials. The resistive termination could encompass from a short to an open depending upon the material under study and its reflections. If a magnetic material is under study, it may be advantageous to have a short at the end of possibly as inductive structure 26D. A pure dielectric would most likely be optimum with an open or capacitive load to achieve a voltage maximum at the end of the probe. Other materials may be absorptive and respond better with a different impedance load than as open or short. A diode load 26E could provide alternating capacitive/resistive loads each ½cycle in addition to providing a DC value relative to the power seen at the load (the transmitted power as opposed to the reflected power). This DC value could be measured back at the oscillator end of the probe using appropriate DC blocks and RF chokes to direct the DC voltage to a voltmeter.

Choice of Probe Substrate and Cover

The simplest substrate 24 is simply fired high-density alumina (essentially $Al_2O_3$) This is commercially available, and is commonly used for microwave circuits (due to its desirable low-loss properties).

Where environmental passivation is needed, and a slight degree of decoupling from the material under test is acceptable, a cover of fired high-density alumina can simply be epoxied onto the substrate and conductor.

Such high-density alumina is impermeable acid inert. However, for humidity-sensing applications, it may be preferable to use low-density material instead. Low-density alumina is somewhat porous, and has an affinity for moisture, but still has reasonable mechanical properties. Thus a substrate and/or cover of low-density material can provide an enhanced signal for detection of ambient humidity changes.

Figure 3A:
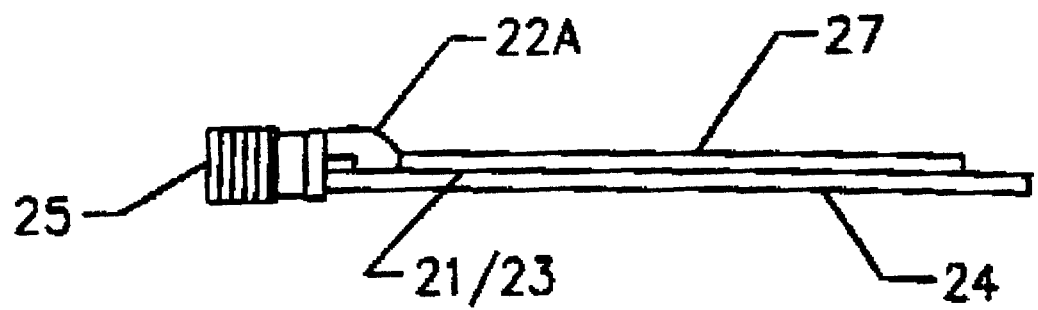
FIG. 3A shows a planar probe wherein the conductive traces are overlaid with a cover of a material which is different from the substrate.

Thus, one alternative is isostatic pressing a powdered composite material atop the substrate 24 and probe traces 21/23, and then baking it to form a cover. The powdered composite material can optionally be admixed with zeolites or other selective-absorbing material. FIG. 3A shows a planar probe wherein the conductive traces 21/23 are overlaid with a cover 27 of a material which is different from the substrate. Note also that an epoxy fill 22A is used to protect the connection of central wire 22 to strip 21.

In a variation of this, the initial substrate 24 can also be made of isostatic pressed low density material, so that, after baking, the traces are embedded in a solid body of absorbing material.

Alternatively, the cover 27 can be made of other materials such a, low-density alumina, fired alumina, other ceramic materials, or even fiberglass.

The probe 10 can be used "bare", i.e. with the leads exposed, if sufficiently inert metallization is used, e.g. gold or a self-passivating metallization such as stainless steel. Alternatively, a thin applied passivation layer can be used, such as plasma-deposited perfluorocarbon, The metallization 21/23, in the presently preferred embodiment, is merely copper (since this can be processed easily with standard printed-wiring-board processes). However, of course, numerous other metallization materials and techniques can be used instead.

For materials having high ionic conductivity (and hence high RF absorption), the conductors can be covered by a separate thin substrate. This would provide a propagation similar to a strip line made where the upper and lower ground planes are in effect the conductive liquid under measurement.

However, in alternative embodiments (as discussed below), substrates with other selective absorption properties can be used instead.

Adaptations of Probe Structure

Dielectric properties of particular fluids being measured can be allowed for by alterations to the structures on the planar probe. This will provide for better field patterns entering the fluids and therefore, increase the sensitivity to the variable under study.

One embodiment is the use of an aluminum oxide ceramic cover 27 over the conducting metallization for obtaining a berrer match into solutions containing ionic salts. The thickness of this ceramic substrate covering will impact the field patterns. Thinner covers would aid in heavy salt solutions. The metallization can also be altered to achieve greater field strengths into the ceramic covers, and therefore into the fluids. These changes would be in the separation between the center conductor and the ground planes.

Other dielectric sandwiches can provide coupling to the medium under study. The top side cover 27 can be of a high dielectric material while the substrate 24 on the lower side is made of a low dielectric. This would help in measurements where the medium has vast changes in dielectric constant.

Figure 1C:
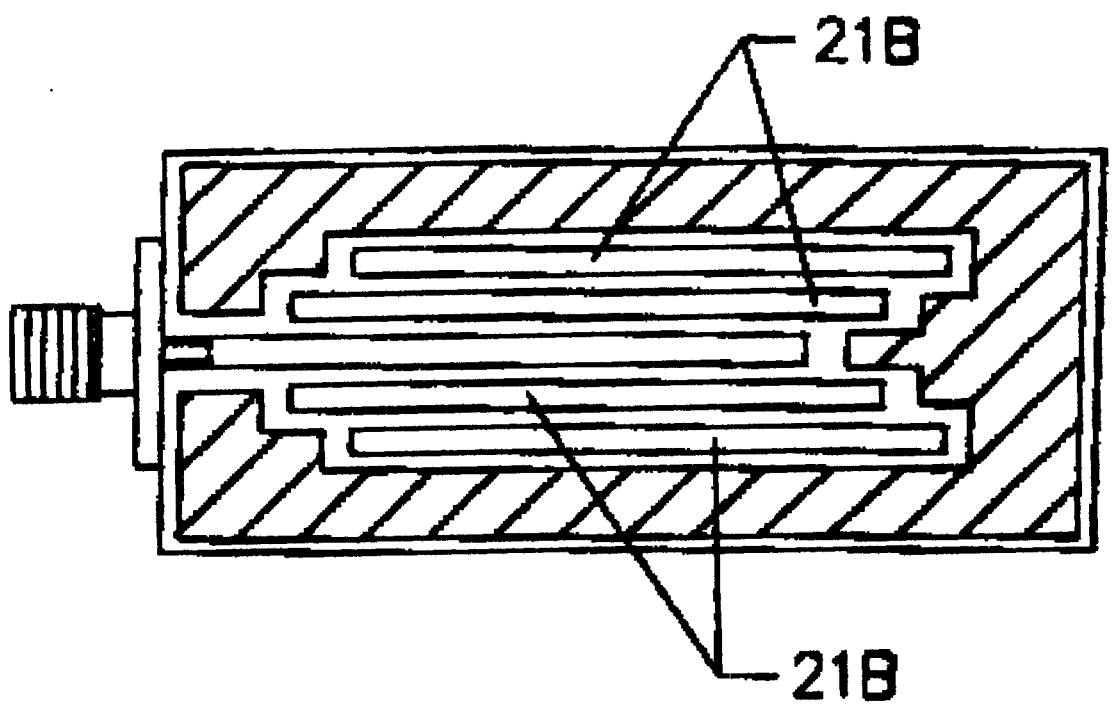
FIG. 1C shows a further modification of the planar probe of FIG. 1, wherein a coupled line structure is used.

FIGS. 1B1 ad 1B2 show a modification of the planer probe of FIG. 1, wherein an impedance transformer is included. While this is not part of the presently preferred embodiment, it may be useful in matching to some materials FIG. 1C shows a further modification of the planar probe of FIG. 1, wherein a coupled line structure is used. The additional lines 21B provide increased apparent line length, as well as some impedance transformation. (Of course, proper selection of the cover and/or substrate material can also be used for adaptations to load density and permitivity, as discussed above.)

The metallization may also be configured to achieve a spiral inductive pattern which would create specific magnetic field patterns to achieve a permeability measurement emphasis. This can optionally be combined with coverings with magnetic characteristics to direct or concentrate the magnetic field.

The prefaced embodiment user various stripline configurations, but alternatively a slotline or other configuration can be used instead.

Probe with Extended Impedance Transformed

The present application discloses a probe which can be readily inserted into a variety of materials in solid, liquid, gas or plasma phase. This probe provide a "single-ended" coupling element which permits load-pull measurements to be made on an increased variety of materials.

A basic requirement of many application is the need for measurement of materials having a wide range of dielectric constant ($\epsilon$ from 1 to 180) using a single transmission line section. This may create problems in launching the electromagnetic energy into a different dielectric medium. Without some help in making a graceful transition from one propagation medium to another (at a very different dielectric constant), the energy will simply be reflected.

The present disclosure teaches that a single-ended probe using a graded impedance (achieved by a planar tapered line or otherwise) can be particularly advantageous for coupling a load-puller oscillator to a material system to be monitored. In alternative embodiments, such probes can also be used for RF sensing in other electrical configuration, using standard instrumentation in the microwave industry as a part of material characterization problems, Such embodiments are less preferable, but can still confer some of the advantages of the claimed inventions.

It should also be noted that it may be advantageous to make the physical length of tapered probe longer than that of a corresponding straight probe.

The preferred approach to this is a "tapered planar" structure, i.e. a planar probe with a taper imposed on the trace geometric. An example of this is shown in FIG. 5B. This provides a compact single-ended probe which can be used for load-pull or other characterization of widely varying material streams. The tapered central structure performs an extended impedance transformation across a significant distance while electromagnetically coupled to the material under test. This solves the problem of coupling to the dielectric material. It also helps to solve the problems of lossy materials such as salt water), where the lossiness of the material can make it difficult to obtain any usable signal at all.

Figure 5A:
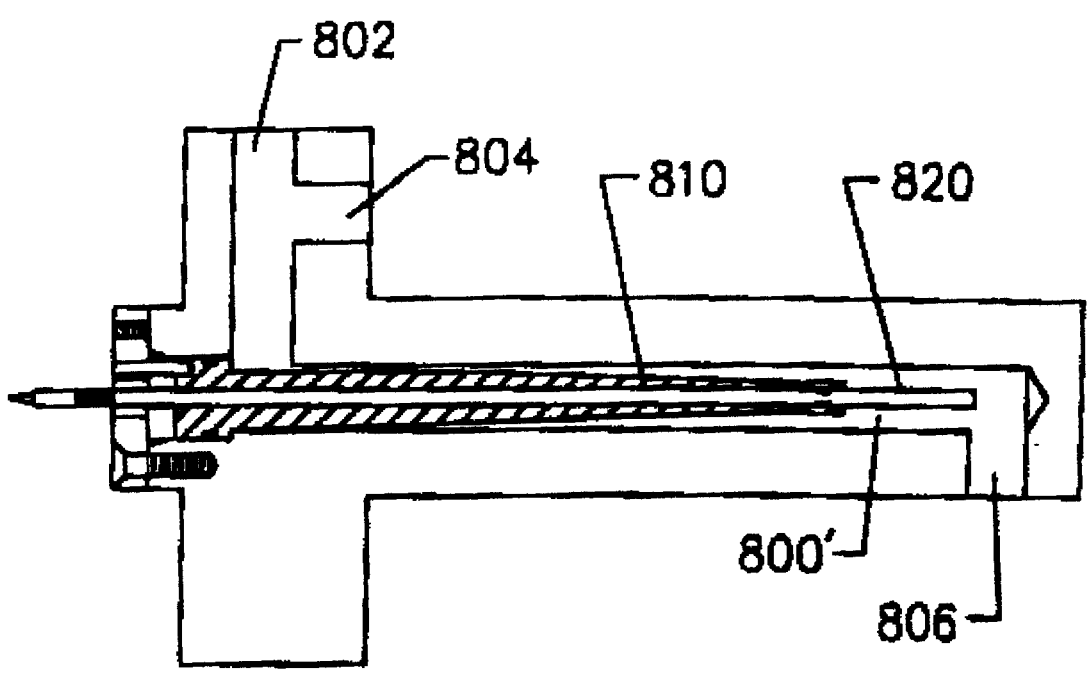
FIG. 5A shows a coaxial load-pull measurement chamber with a tapered dielectric sheath on the central conductor.
Figure 5B:
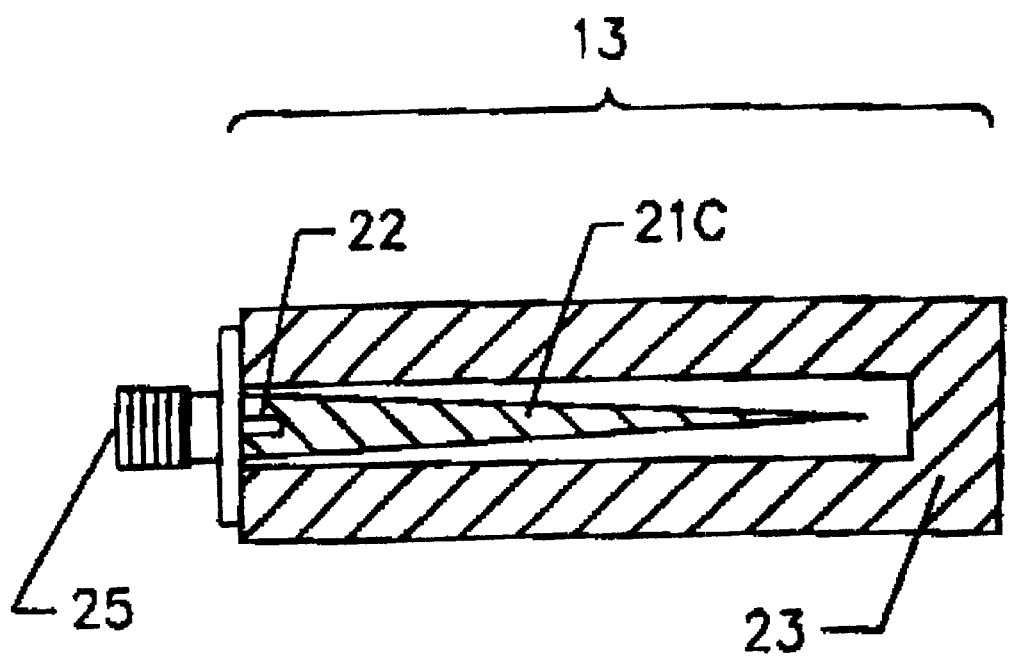
FIG. 5B shows a planar tapered probe.

FIG. 5A shows as alternative single-ended probe embodiment, for use with flow-through piping designs like those described in U.S. Pat. No. 5,025,222, and PCT application WO 91/08469, both cited above. FIG. 5A shows a load-pull measurement chamber 800' with a tapered dielectric sheath 810 on the central conductor 820. The extension of the base center rod 820 through the tapered sheath 810 provides for the electrical length to increase with small $\epsilon_n$ since the lower $g_n$ will still be of sufficient impedance to allow the continual propagation of the electromagnetic wave. In the configuration shown, the top port 802 is used for introduction of a temperature Probe, and the process fluid flows from port 804 through to output port 806. It may be seen that clearances are tight, in the configuration shown. The sheath 810 is preferably machined with a flat (not shown) on its top side, for reduced flow resistance.

For lossy materials, the taper will also give a gradual entry into the highly ionic fluid which should give rise to a graceful loss/length relationship. For less lossy, low $\epsilon_n$ material the bare rod should aid in the determination of the loss since it will more readily show low loss.

If fluids with well known $\epsilon$'s are placed in this test section and frequency and incident and reflected plowers noted, a calibration curve should be generated which can be related to various VCO/pipe configurations. The pipe section used way a version of the 0.5"5" long unit with ⅛" rod. The taper was across approximately 3" with the center rod protruding ~6" past the end of the taper.

Probe with Selective Absorption Material

The present application discloses structures and methods for enhanced RF detection using chemically selective materials on an RF probe. The chemically selective material may be a coating, or may be part of the substrate, or may be a separate cover. At least part of the selective material is placed in proximity to the RF propagation structure, so that absorption of a target species by the selective material will change the dielectric loading seen by the RF propagation structure.

Figure 4A:
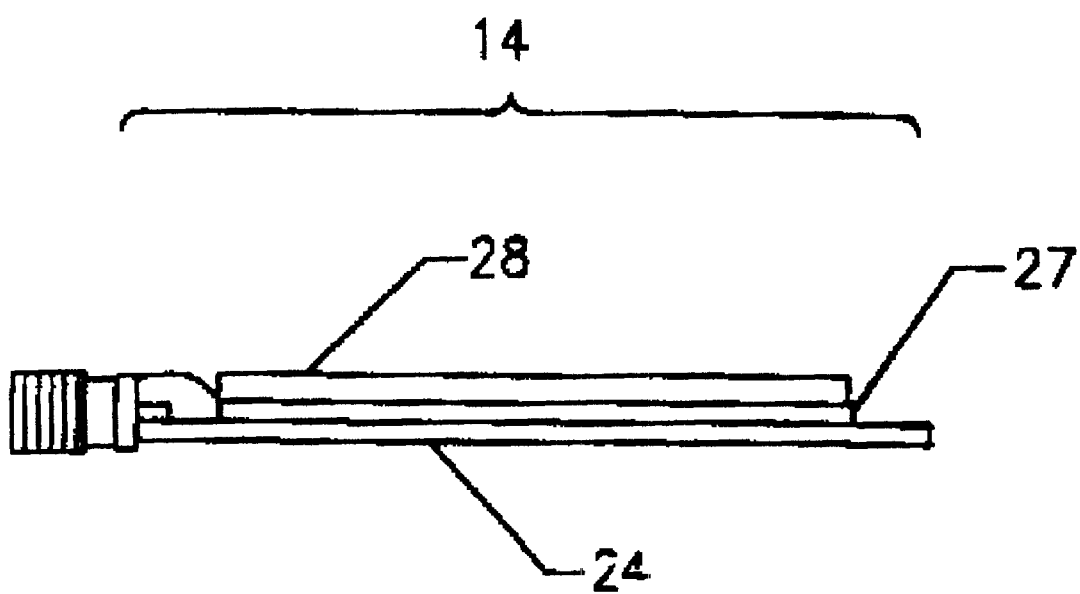
FIG. 4A shows a planar probe with an added relative absorption layer, for chemically selective signal enhancement

The selective material can be attached in various ways. FIG. 4A shows a planar probe 14 with an added selective absorption layer 28, for chemically relative signal enhancement. Note that, in the configuration of this Figure, the absorber ("active material") 28 overlies the cover 27, as opposed to the more common configuration where the active material 28 substitutes for the cover 27.

FIG. 4B shows a planar probe 15 with beads 28" affixed thereto, for chemically selective signal enhancement.

Figure 3B:
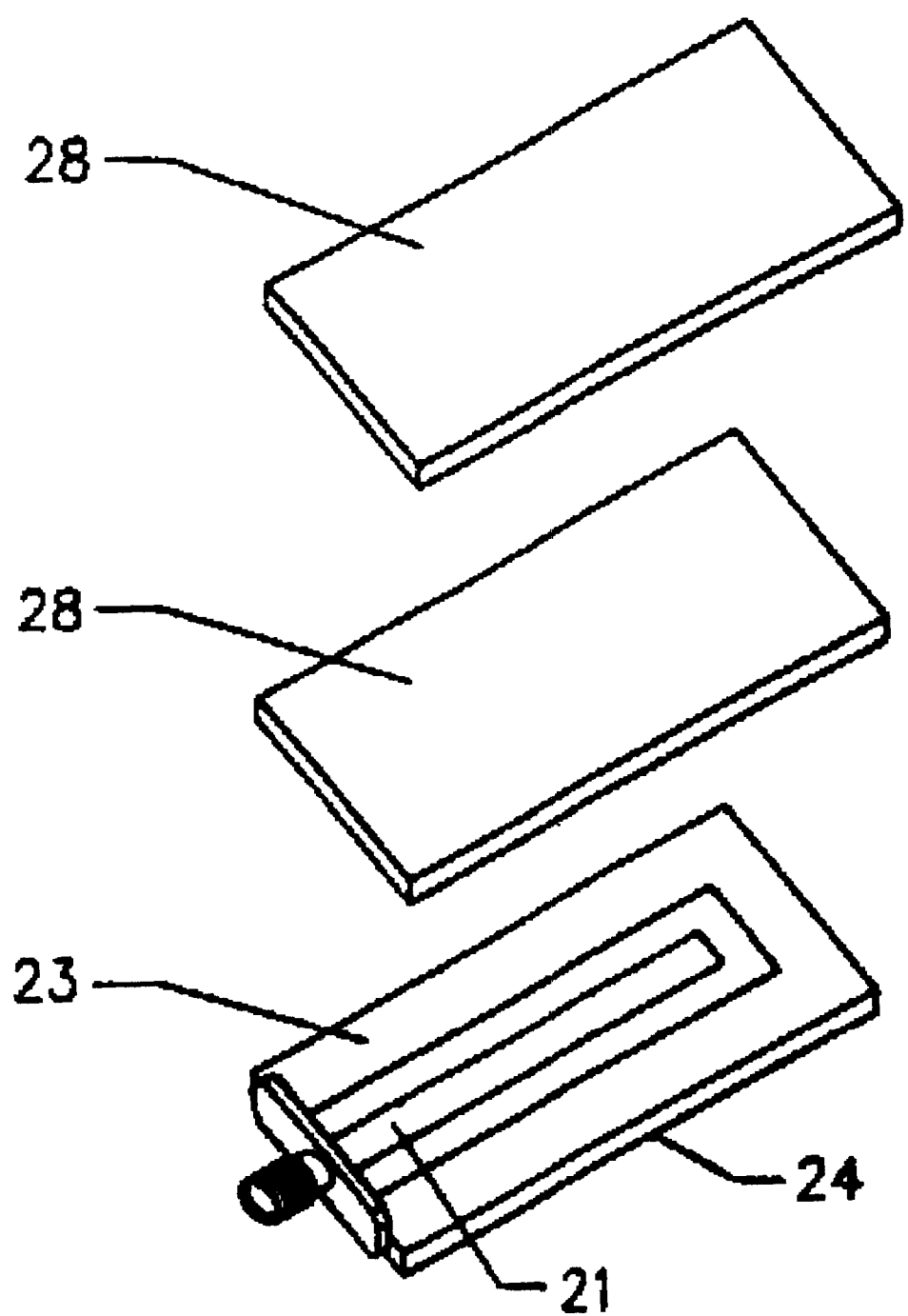
FIG. 3B shows assembly of a planar probe with a cover.
Figure 4C:
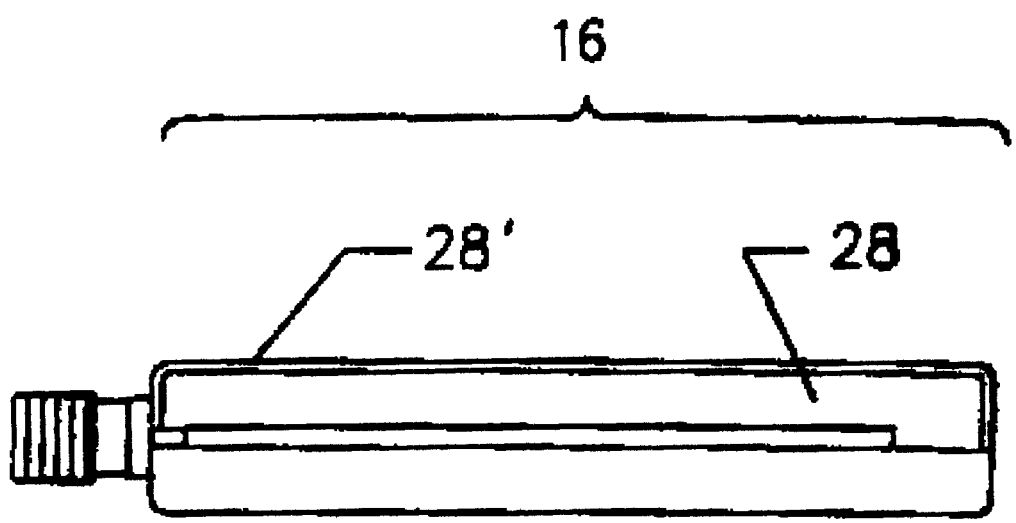
FIG. 4C shows a planar probe with an added selective absorption layer and a stabilizing overcoat.

FIG. 4C shows a planar probe 16 with an added selective absorption layer 28 and a stabilizing overcoat (protective membrane) 28'. FIG. 3B shows assembly of a planar probe substrate 24 to a selective absorption layer 28 and a stabilizing overcoat (protective membrane) 28'.

The selective material can be anything which will support an electromagnetic field and have specific properties far a chemical structure. Examples include zeolites, ceramics with specific absorptions, doped semiconductors which increase/decrease their conductivity/dielectric constant with absorption. A further alternative is the use of enzyme embedded in a porous structure which are altered by selective substances may also be possible. This change in the enzyme structure would be visible with the load pull scheme. If a substrate was embedded or coated with a material which would deteriorate with selective absorption, the monitoring of the degradation can give rise to determination of the amount of the chemical present.

For another example, zirconia hag unusual properties with oxygen at high temperatures. It forms a ion exchange with oxygen molecules which is used to measurement oxygen content of gas streams especially in cars and stack emission monitoring. It is contemplated that use of this as a substrate can be advantageous for $O_2$ monitoring.

In the medical, food and pharmaceutical industries, it can be advantageous to implement the selective-absorber substrate 16 and a throwaway substrate, to preserve sterility.

A particular advantage of the absorber-coated probe is that it can be designed to be self-calibrating. By contrast, other probes may need to be calibrated with a sample which is (or approximates) the material in question.

Figure 21:
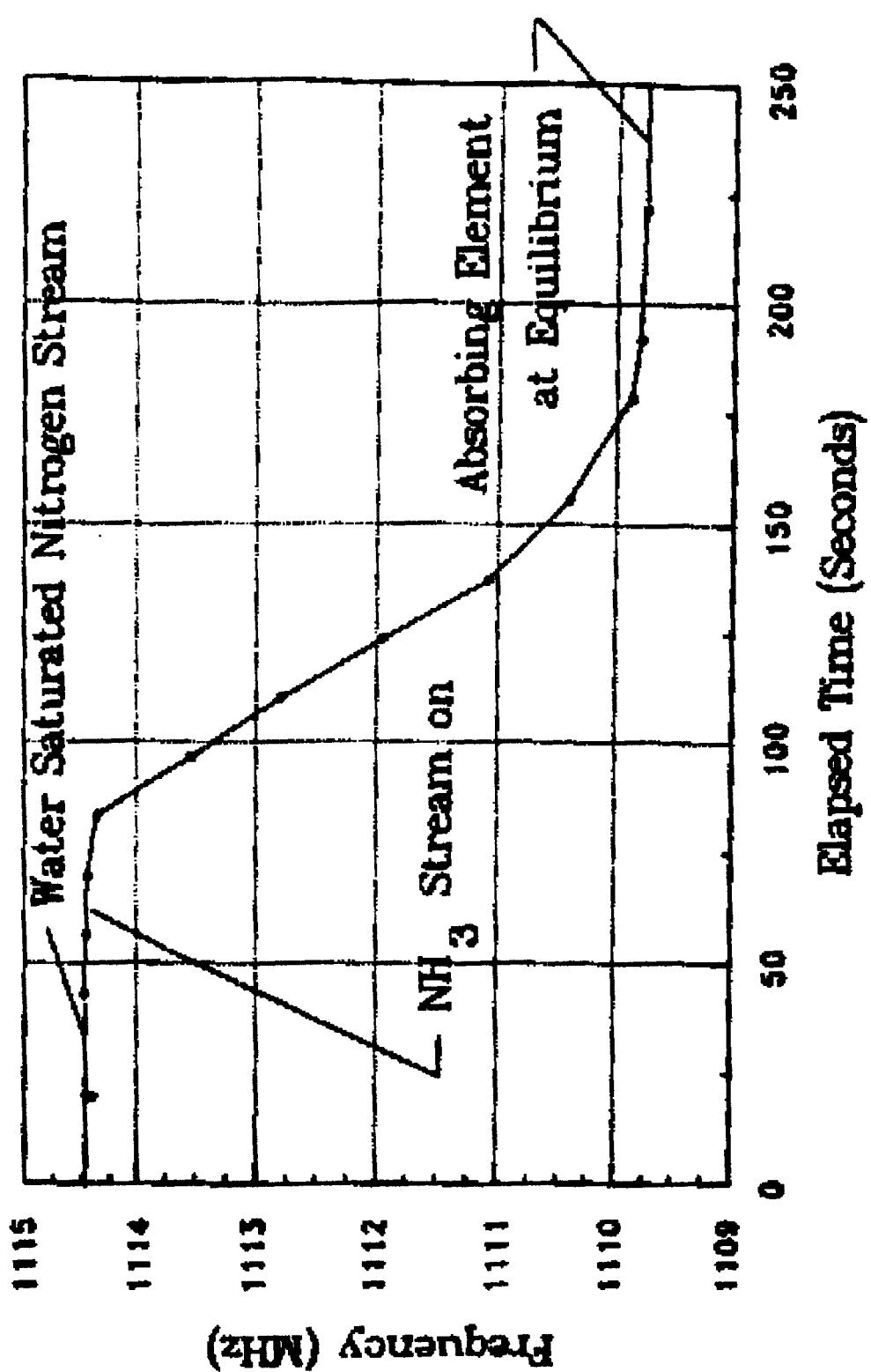
FIG. 21 shows actual data from in-situ monitoring of selective absorption of ammonia from atmosphere performed at room temperature using a modified zeolite on a planar probe.

FIG. 21 shows actual data from in-situ monitoring of selective absorption of ammonia from atmosphere performed at room temperature using a modified zeolite on a planar probe. The absorbing element is a modified zeolite which absorbs $NH_3$ but not water. The initial oscillator frequency was about 1114.5 MHz, and this did not shift significantly while a flow of $H_2O$-saturated nitrogen was applied. After an additional flow of ammonia was added to the $H_2O$-saturated nitrogen flow, the oscillator frequency shifted over a period of 30 minutes, as indicated on the chart, by 4.8 MHz downward. (The numerals on the X-axis are arbitrary designators; each numeral corresponds to about 13 seconds) Note that the rate of change declines markedly near the end, as the absorbs near equilibrium with the vapor-phase concentration. The specific zeolite used in this experiment also selectively absorbs HCN, so this same structure can also be used for a danger warning in an environment, e.g. in metal-plating operations.

The simplest application of selective absorption is for humidity sensing e.g. using an absorbs of low-density $Al_2O_3$ (alumina). Alumina will equilibrate to a moisture concentration which is exactly proportional (within a certain range) to the ambient humidity. (The interaction between alumina and water is typical of many materials systems, where the relative equilibrium concentrations of a solute S in materials A and B are linearly related by a segregation coefficient $k=[S]_A/[S]_B$.) However, the present invention does not require as much time as would be needed for equilibration. Instead the rate of uptake of humidity by the absorber is differentially monitored, and this provides a fast measurement which also is related to the ambient humidity.

Figure 11A:
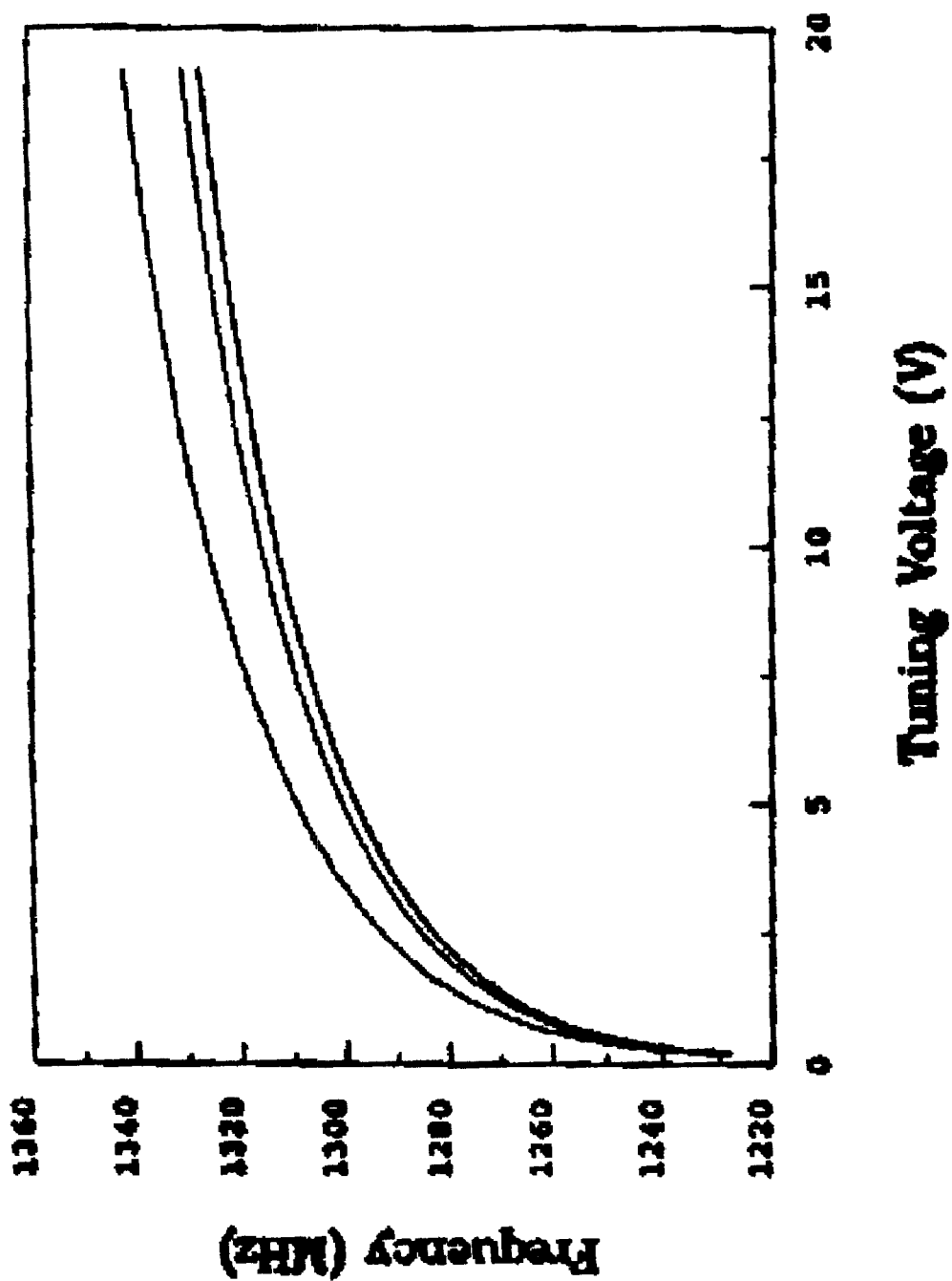
FIG. 11A shows actual measured results from monitoring moisture absorption by alumina beads (from Alcoa™) affixed to a planar probe.
Figure 11B:
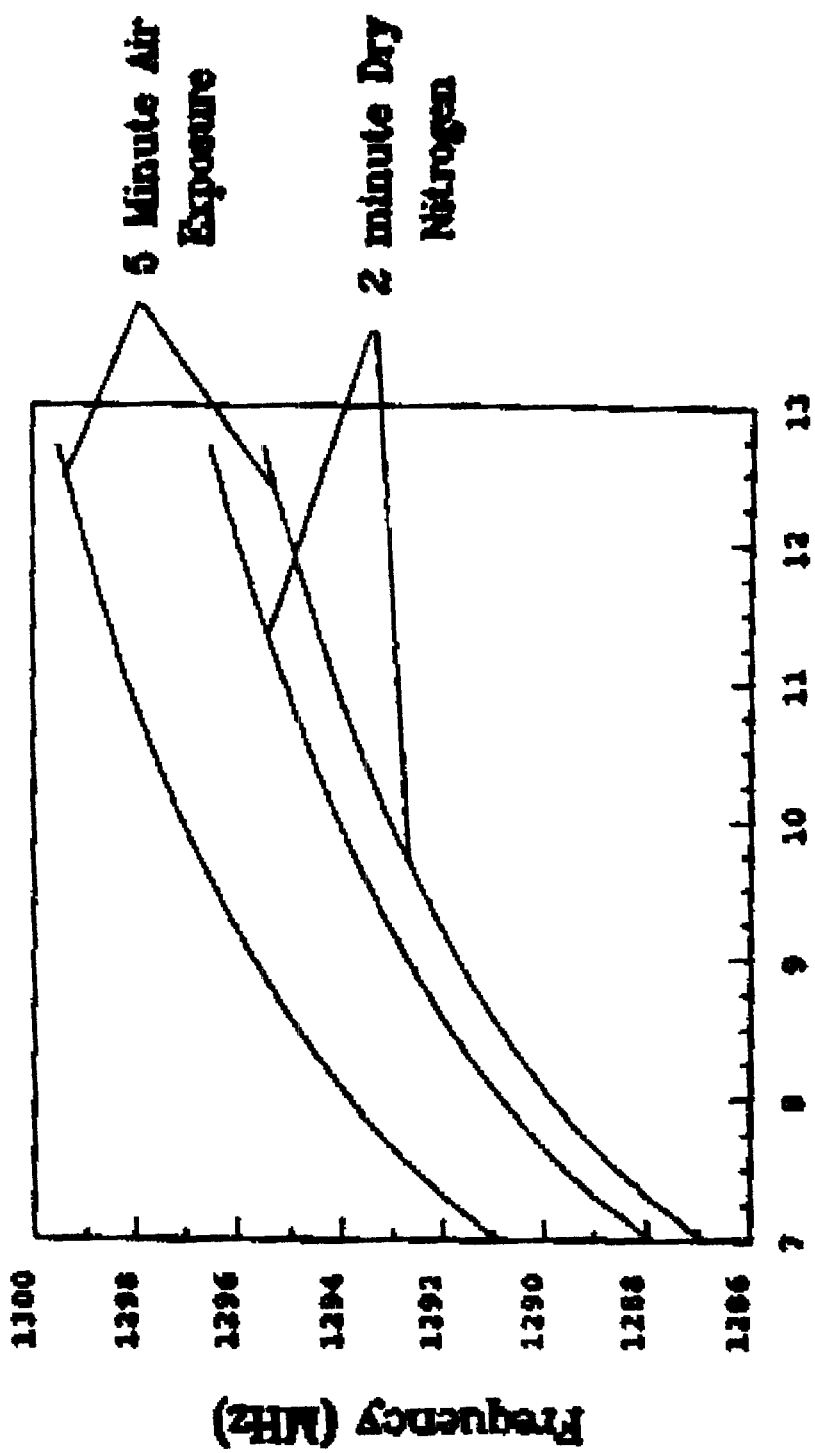
FIG. 11B is an expended plot of some key data points from the plot of FIG. 11A.

FIG. 11A shows actual measured results from monitoring moisture absorption by alumina beads 28" (from Alcoa™) affixed to a planar probe 15. In this Figure the oscillator frequency goes from 1230 to 1332 MHz as the tuning voltage, the is ramped from 4.3 V to 20 V. (In all of the following plot of oscillator frequency versus tuning voltage, the tuning voltage is typically swept across the range shown in tens of milliseconds to tens of seconds.) FIG. 11B is an expanded plot of some key data points from the plot of FIG. 11A. The top curve shows an initial state, in which the oscillator frequency goes from about 1286 to 1312.4 MHz as the timing voltage is ramped from 7 V to 13 V. The arrow marked * shows the shift in frequency behavior for 5 minute exposure to 100% relative humidity. In the resulting curve (the lowest shown), the oscillator frequency goes from below 1280 MHz w about 1306.5 MHz as the tuning voltage is ramped from 7 V to 13 V. The arrow marked ** shows the further shift in frequency behavior after exposure for 2 minutes to a dry nitrogen flush. In this curve the oscillator frequency gas from 1280 MHz to about 1307.6 MHz as the tuning voltage is ramped from 7 V to 12 V.

Figure 12:
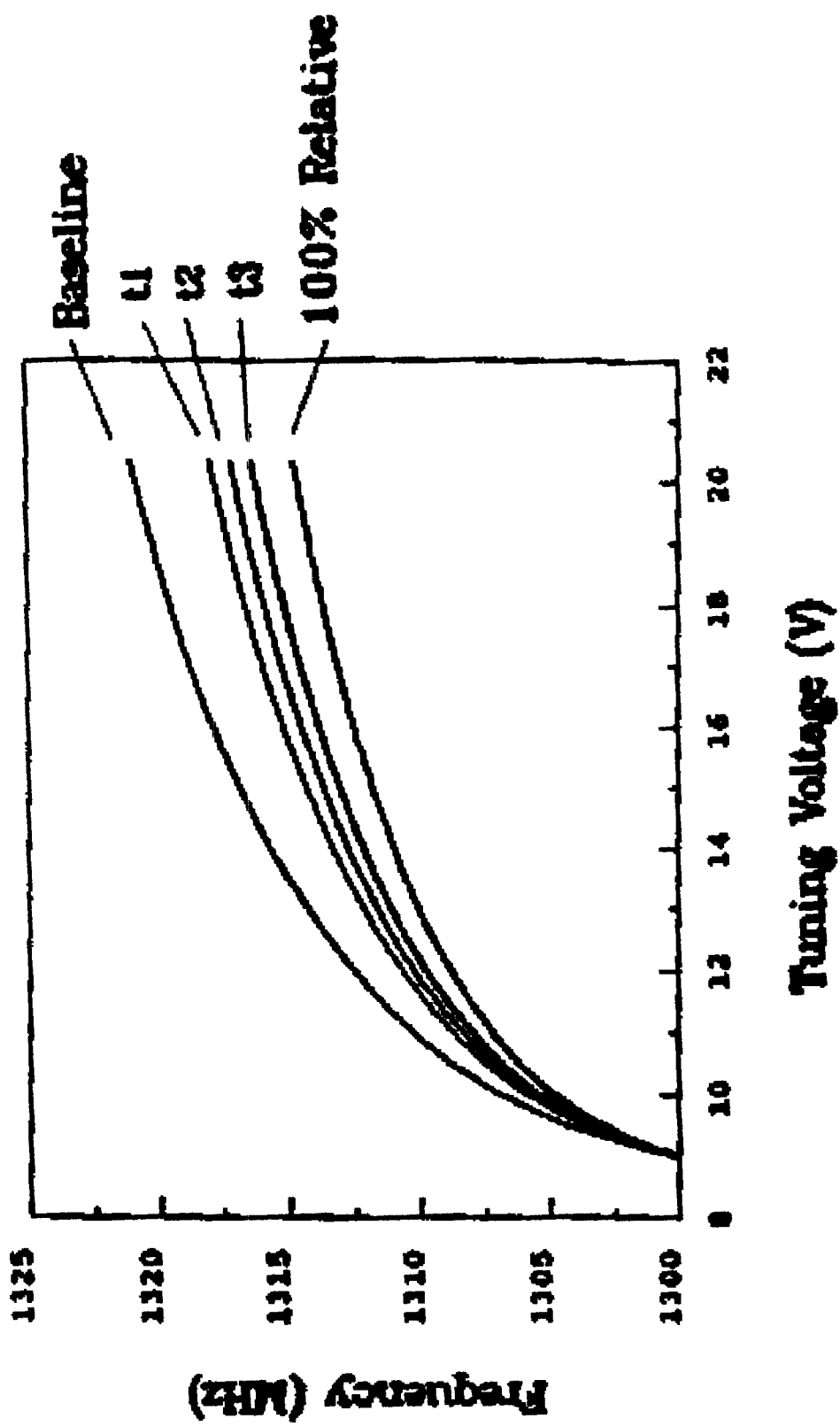
FIG. 12 shows actual measured results from moisture absorption by a low-density alumina disk affixed to a planar probe.

FIG. 12 shows actual measured results from monitoring moisture absorption by a low-density alumina disk affixed to a platter probe. This disk was custom-made for this periment by low-temperature sintering of "A-300" rehydratable activated alumina powder from LaRoche Chemicals Inc., Baton Rouge La. Two parts of unground powder are mixed with one part of water, pressed to shape, and baked for three hours at 400° C.

The multiple traces in FIG. 12 indicate successive runs at separate times $t_1-t_3$. The last run ($t_3$) was made after 12 hours in approximately 100% relative humidity. In this curve the oscillator frequency goes from about 1302 MHz to about 1317.1 MHz as the tuning voltage is ramped from 10.1 V to 20 V. Also shown, for comparison, is a "0" line (0% humidity, desiccated) and a curve for the bare planar probe. In the "0" line curve the oscillator frequency goes from about 1302.7 MHz to about 1320.4 MHz as the tuning voltage is ramped from 10.1 V to 20 V. Note that a frequency difference of more than 3 MHz is seen at the highest frequency. Thus, by interpolation, the minimum detectable humidity change would be about 0.001%!

Note that the absorbent material need not be readily reversible. For example, there is a vast literature on customizing zeolite structures to make "molecular sieves." However, the affinity of many such structures for their complementary substance is so high that the adsorbate is very tightly bound. Thus, a zeolite absorber may need to be periodically purged, or simply discarded when saturated.

Figure 29A:
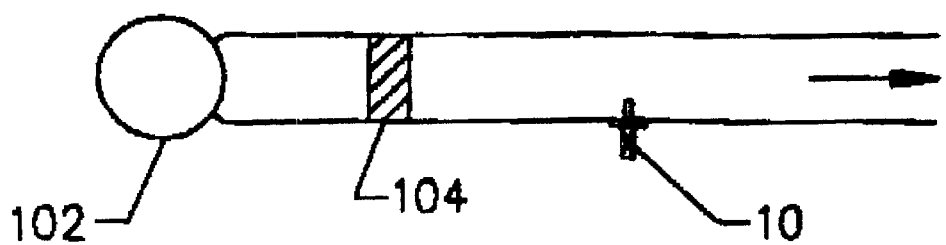
FIGS. 29A–29C show three system configuration in which the disclosed inventions are used for humidity measurement.
Figure 29B:
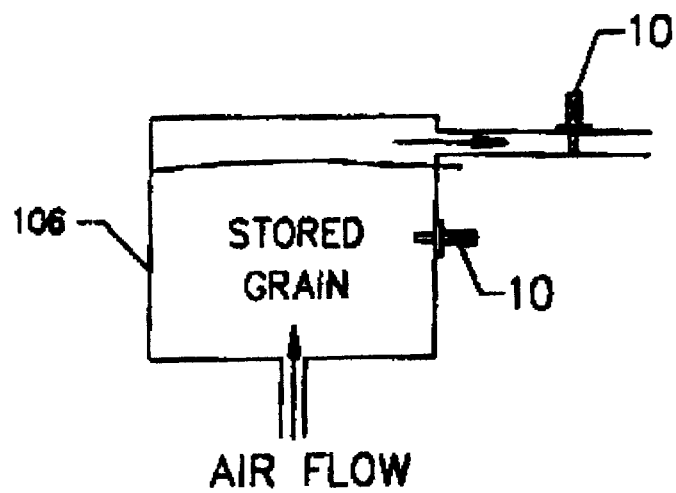
Figure 29C:
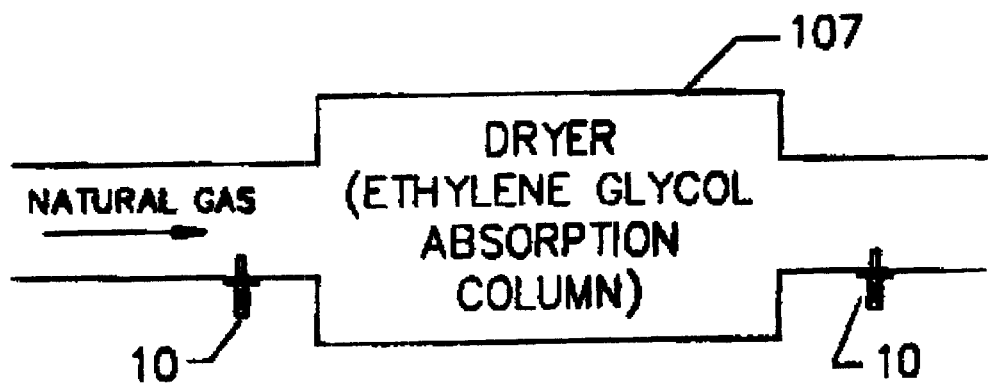

FIGS. 29A–29C show three system configurations in which the disclosed inventions are used for humidity measurement. FIG. 29A shows a blower 102 passing air over a humidifier 104, which is controlled in accordance with measurements taken at the probe 10.

FIG. 29B shows a system configuration used to measure the moisture equilibrium of water vapor (and hence grain water content) in a grain storage facility where air is flowed through a grain bin 106 to an exhaust port 108.

FIG. 29C shows a system configuration for measuring water content in a natural gas flow using RF probes 10, and controlling an ethylene glycol dryer column 107 accordingly.

One alternative class of embodiments uses an absorptive probe in a sealed package: if an active matrix material such as a zeolite is used for moisture measurement in grains and food solids, a "zip open" sealed bag can be useful for field use.

For example, an RF probe with a dry active zeolite is shipped sealed in a plastic bag. When the customer is ready to actually make the field measurement, the probe is connected to the RF line and placed in a container (for example, a carload of given), and the rip cord is pulled to open the bag and "activate the probe". This would allow use of a zeolite material which is very aggressive (to water). The advantage would be time to equilibrium. This may also be useful in other reactive substrate cases.

It should also be noted that the "absorber" material does not have to be a merely physical absorption, but may alternatively be a reactive material which chemically reacts (reversibly or irreversibly) with the target species.

Probe with Heater

A further embodiment provides an RF probe 17 which not only includes a selective-absorbing material 28 (such as alumina), but also includes a heater 29 for causing desorption of the absorbed material. This permits the heater to be "cycled" efficiently.

The heater 29 can be embedded in the ground plane or placed on the backside of the substrate. This heater would be activated at either a set value of frequency change or at time intervals. During the on cycle the change in the material can be simultaneously monitored by the same load pulled oscillator to determine when the regeneration point has been reached or to indicate to an operator that the time to replace the probe and material has arrived.

This embodiment also permits some aggressive absorbing materials (such as high-affinity zeolites) to be used for selective absorption.

This embodiment is particularly attractive for field measurement of humidity, but can also be used for measurement of other substances.

In some applications, this heater can also be used to provide temperature regulation of the probe's immediate environment, if the material under test would not provide a heavy thermal load. For example, this may be useful where the sample is gaseous and of variable temperature.

Figure 4D:
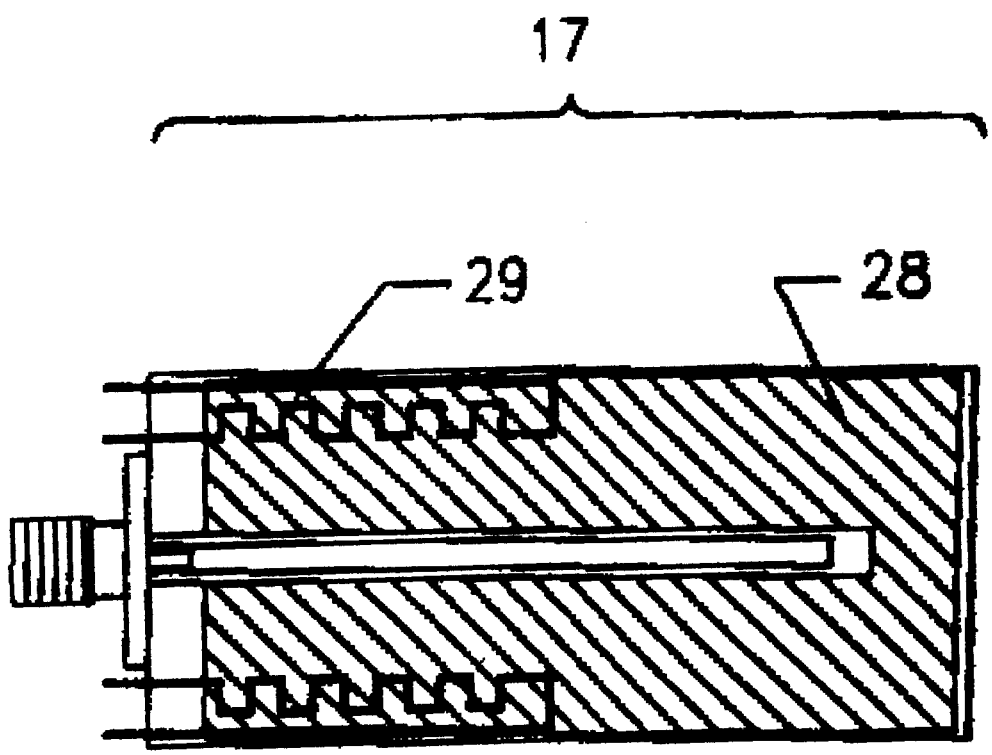
FIG. 4D shows a planar probe with an added relative absorption layer thereon, and with a heater integrated on the same substrate.

In the presently preferred embodiment of this invention, as shown in FIG. 4D, separate leads are provided to power two resistive heaters 29 in a planar structure. However, in an alternative embodiment a resistive heater can be driven by a DC component on the coaxial line (if the power detection diode is not used). In this embodiment, an isolating inductance can be used with the heater to avoid resonances.

In a further alternative embodiment, a backside heater is combined with a ground plane. In this case the ground plane should preferably have a reasonably high conductivity, to avoid excessive damping of the signal of interest, and therefore a low-voltage power supply is preferably used for the heater.

Figure 30A:
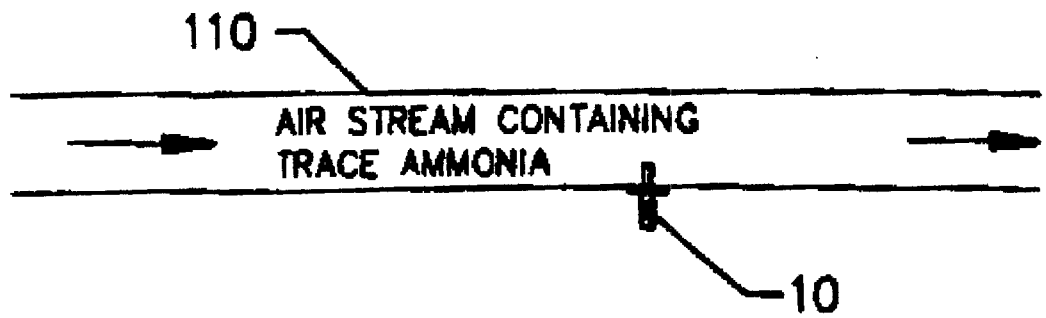
FIG. 30 shows absorption/desorption cycling, for use of a probe having a selective absorption material and also a desorption heater.
Figure 30B:
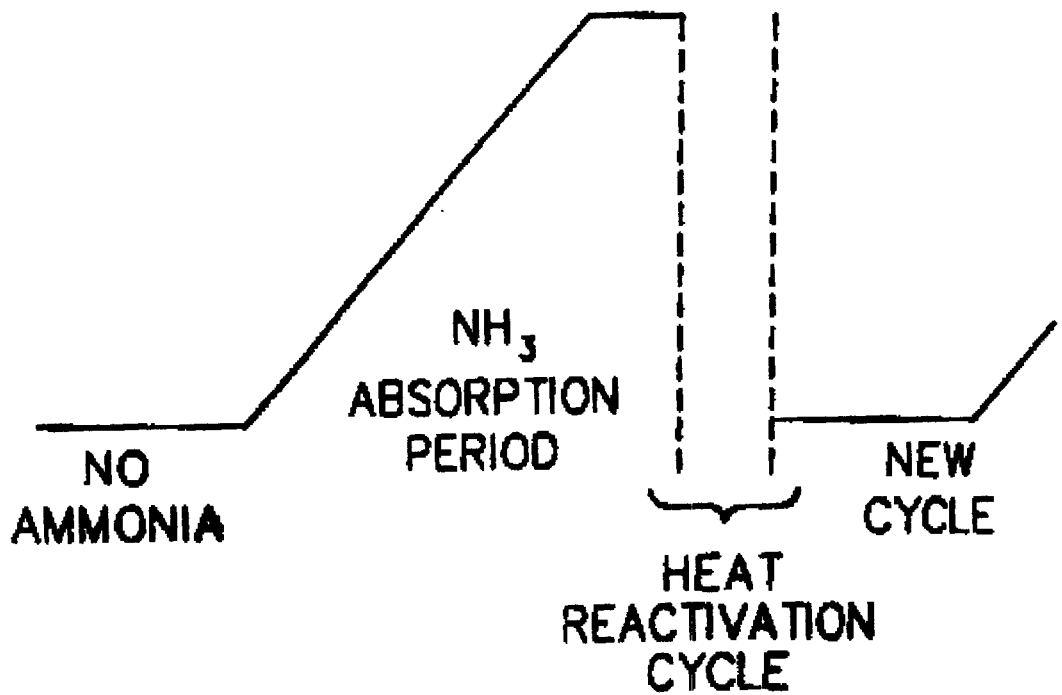

FIG. 30 shows absorption/desorption cycling, using a probe having a selective absorption material and also a desorption heater. The selective absorption material, in this example, is selective to ammonia ($NH_3$). An air stream 110 with traces of ammonia is passed over an RF probe 10 which includes a selective absorption element, and the change in oscillator frequency is used to monitor uptake of ammonia. When the absorber becomes loaded, the heater is activated, and a new cycle of absorption is begun.) During each absorption cycle, the rate of uptake can be measured using time-differentiated measurements. An integral is accumulated to provide an index of the total loading of the absorber. The relation between this integral and the rate of uptake provides an index of the ambient concentration. When the integral exceeds a certain threshold, this indicates that the absorber is becoming fully loaded. The heater is then activated to refresh the absorber and start the cycle again.

Probe with Two Selectable Transmission Lines

A further disclosed innovation is a single-ended probe which includes multiple transmission line segments, and which also includes an RF switching element connected to permit switching between the two segments (or at least controllable disabling of one segments). In the presently preferred embodiment, each transmission line is preferably nonresonant over the full range of frequencies of interest, although it may have resonances at other frequencies. However, it is also contemplated, as an alternative embodiment, that a structure which is resonant near a second harmonic of the operating frequency may be advantageous.

FIG. 4E shows a planar probe 18 with TWO transmission lines 21D (only one of them overlain by an added selective absorption layer), and an RF switch 22' to select which of the two transmission lines 21D will be active.

There are many ways to use this capability. For example, one of the two lines can be an uncovered metal trace and the other can be covered with a material which selectively absorbs (or reacts with) a particular chemical. This combination would provide a measurement of a specific substance using the covered side of the probe, and once this component of the material under study is known an additional component could be derived from the response from the bare side of the probe. For example, if the covered side uses an active material to discern glucose in a dextrose/glucose/water mixture, the bare side's additional information would permit determination of the water content of the mixture.

This can also be used to provide spatially-resolved differential measurement for detection of spatially-varying characteristics (e.g. material zone boundaries in a distillation or chromatographic column).

Patch Probe

In many applications the avoidance of direct contact with the materials under test is overwhelmingly desirable, to prevent contamination. To meet this need, the present application discloses a noninvasive RF probe which can be readily coupled, through a dielectric window, to a material under test. This probe provides a "single-ended" isolated-coupling element which permits load-pull measurements to be made on an increased variety of materials. The electrical configuration of this probe is like that of a patch antenna, and hence this probe may be referred to as a "patch probe". The patch probe is inherently less sensitive than a probe which is directly immersed in or inserted into the material under test, but may be sufficiently sensitive for many applications.

FIGS. 7A1 and 7A2 show a first sample embodiment 19A of a patch probe, for coupling through a dielectric wall (or window) to electrically monitor the contents of a vessel or process flow. This embodiment uses a spiral-inductor configuration.

FIGS. 7B1 and 7B2 show two views of a second path probe embodiment 19B, which also can be used for monitoring materials through a dielectric wall. In this embodiment the two leads of the incoming RF coaxial line are connected to a center dot 19B2 and a peripheral ring 19B1, both made of thick-film metallization. A circular path 7B3, on the opposite side of the dielectric puck, affects the near-field patterns to achieve proper electromagnetic coupling to the medium of interest.

Figure 8:
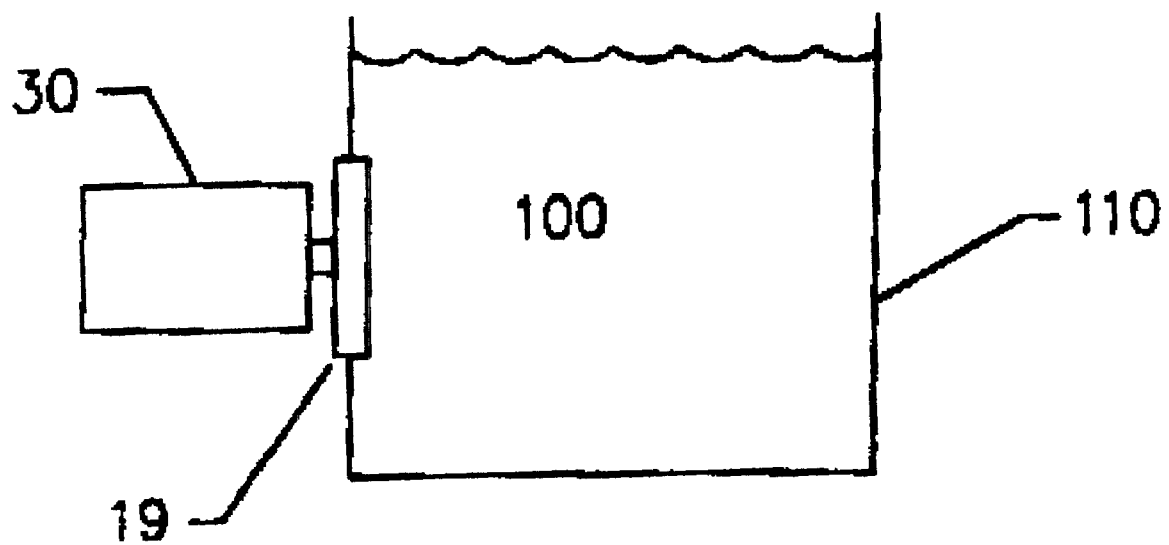
FIG. 8 shows an example of mounting a patch antenna, in a reflective configuration, to monitor the electrical characteristic of a fluid screen or a vessel.

FIG. 8 shows an example of mounting a patch probe, in a reflective configuration, to monitor the electrical characteristics of fluids 100 in a pipe or vessel 110.

A planar probe can also be used for coupling through a window. In this case the planar probe would be placed flat against the window. However, the patch probe is preferred for such applications.

One alternative modification of the disclosed invention is to use a pair of probes as transmit and receive antennas for propagation of the RF energy through a thickness of the material to be characterized. However, this is not presently preferred.

Method for Identifying Changes in a Given Process

The present application discloses a method for rapidly analyzing the state of a given process. A load-pulled oscillator is coupled to the material under test, and is swept across a range of frequencies. The oscillator frequency is swept, for example, by sweeping a tuning voltage, applied to a varactor in the oscillator circuits, across a predetermined range. The oscillator is coupled to the material under test by a probe which is electrically long (preferably at least several half-wavelengths when fully loaded by the material under test). The specific conditions (probe type, physical conditions of coupling, and range of tuning voltages or frequencies) will all have been previously defined, using the various considerations set forth in detail below. The oscillator frequency is monitored while the tuning voltage is swept in a predetermined direction (up rather than down, for example).

For this defined set of conditions, each sweep of the tuning voltage $V_{tun}$ will produce a corresponding range of oscillator frequency values $f_{osc}$. By integrating $f_{ose}$ over the predetermined range of $V_{tun}$, a single derived index number results. This turns out to be very useful in characterizing a given process under a given set of conditions.

Part of the reason for this is that shifts in material composition which produce even very small shifts in permittivity will have the effect of shifting the "knees" in the frequency curve. These knees, which are readily visible in plots of oscillator frequency as a function of tuning voltages, correspond to points where the oscillator phase goes through a 180° transition. When this occurs, the oscillator will return to its original operating frequency, and this frequency is likely to shift.

To better explain this method, some more extensive analysis will now be provided.

An oscillator builds up oscillations from a linear operating point if it has more gain than is necessary for oscillations. The oscillations begin with device noise as a triggering function. As the oscillations build up, the gain is reduced due to the change in the operating point on the load line of the current/voltage relationships of the active device. In essence, the device goes sufficiently far into saturation to reduce the gain to unity for the loop. This prevents the phase from being a simple linear function of the load.

Now, consider what happens when load impedance varies.[18] As the load impedance plane is traversed by the varying permittivity of the load, the gain and phase of the oscillator will shift in a non-linear fashion to maintain a unity gain and 180 degree phase shift. The point which satisfies both requirements of unity gain and 180 degree phase shift and this point becomes the new frequency of operation. This is the phenomenon of "load pull," and is conventionally avoided by appropriate isolation of the oscillator from the load; but in the load-pulled oscillators used to implement the present inventions, of course it is not desired to avoid his effect.

[18]Of course, at frequencies above approximately 100 MHz, any load will tend to act as distributed rather than lumped, and a transmission line type of analysis is required.

The load pull phenomena has a characteristic of a change in frequency with a change in load impedance seen at the oscillator's output terminal. However, this frequency cannot continue to change indefinitely; it only changes up to a point where the phase exceeds 180 degrees from the lowest frequency's impedance, and at this point the oscillator returns to its original frequency. These transitions will be referred to herein as "knees."

Figure 28:
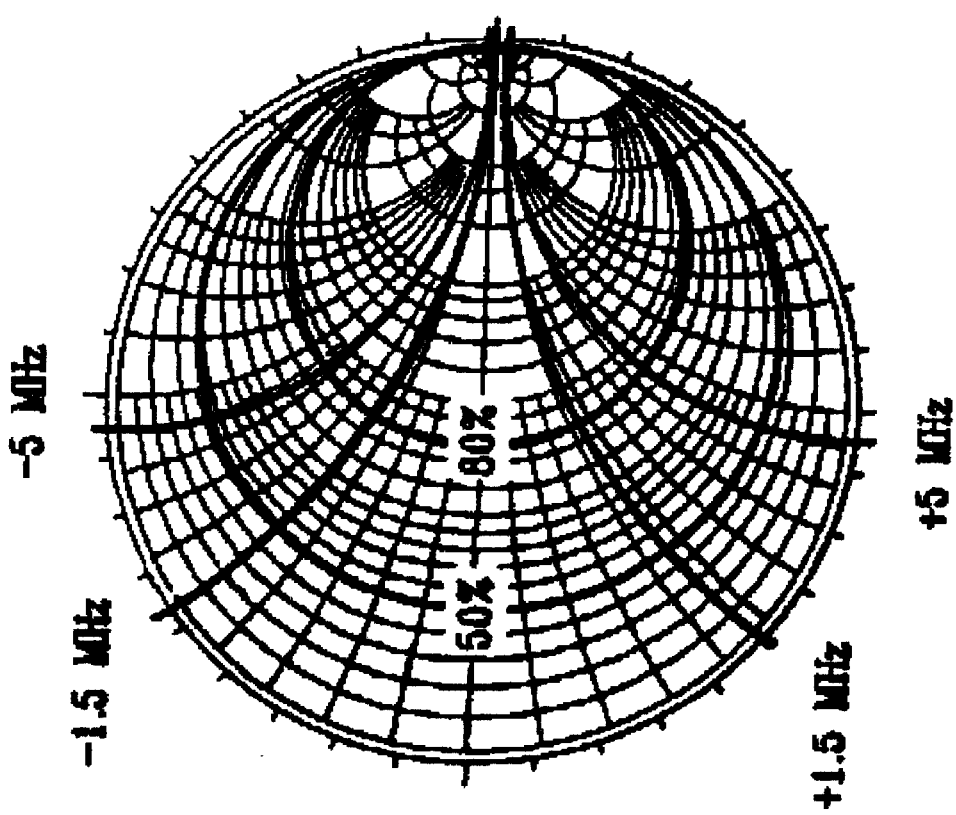
FIG. 28 shows an example of a Rieke plot, in which oscillator power and frequency are plotted as a function of the load admittance presented at some point in the output circuit of the oscillator.

Oscillator load pull is characterized by a graph called a Rieke plot. (A sample Rieke plot, for an ideal case, is attached as FIG. 28.) This is a plot of the oscillator power and frequency as a function of the load admittance[19] presented at some point in the output circuit of the oscillator. It is presented on a Smith admittance chart with an overlay of constant power and frequency contours. The susceptance[20] component of the load admittance adds to the susceptance of the oscillator tank circuit, to produce a net susceptance (or reactance) which determines the frequency of operation. The oscillator's susceptance must compensate for this change in output admittance by a change in frequency to again cancel contribution from the output and meet the requirement for 180 degrees of phase shift around the active device. The reason for this is because we are dealing with a transmission line system where the line lengths internal to the oscillator and the load can go from inductive to capacitive at a given plane of reference at the output of the oscillator. (This explains the existence of "knees".) In addition, the output power relationships must also maintain a constant relationship with the conductance. In the purest case the lines of constant conductance relate directly to those of constant power, and those for constant susceptance relate to constant frequency. Since this is the case, the "Q" (resonant quality factor) of the oscillator's resonant circuit determines the amount of frequency change per unit of susceptance. This "Q" factor is set by the circuit elements of the oscillator's feedback path. Deviations from this are seen in the actual Rieke diagrams and are caused by the non-linear effects due to the changes in device terminal susceptances as the device's operating point goes further into saturation (or

[18]Of course, at frequencies above approximately 100 MHz, any load will tend to act as distributed rather than lumped, and a transmission line type of analysis required.
[19]Admittance is the reciprocal of impedance, and is a complex number.
[20]Susceptance is the imaginary part of admittance, and also corresponds to the reciprocal of reactance (the imaginary part of impedance). out of saturation). Also, it can be shown that the output power is related to the load in such a fashion that for increased output power, the unstable/no-oscillations region about the infinity portion of the Smith chart will increase in size.

Each unit change of susceptance can be related to the load impedances by the equation for the reflection coefficient for a transmission line. The voltage reflection coefficient is $$\Gamma = \frac{Z_r - Z_o}{Z_r + Z_o}$$

where $Z_o$ is the standard impedance of the 50-ohm coaxial line, and $Z_r$ in this case is the input impedance of the transmission line, or $$Z_r = \sqrt{\frac{R + j\omega L}{G + j\omega C}}$$

where R, C, L, and G are distributed parameters for series resistance, shunt capacitance, series inductance, and shunt conductance, respectively. The reflection coefficient is the vector which describes the trajectory around the Smith chart which forms the outer bounds of the chart for an equal impedance line of $Z_o$. Since this equation relates the phase angle of the load to the impedance, the phase length (and therefore frequency) will become a function of the unit susceptance. Therefore, longer transmission lines will cross a given unit susceptance interval more quickly than shorter lines and increase the sensitivity of a load-pull system. This means that pulling is relational to the wavelength (which is frequency and length).

In a typical application the oscillator's basic frequency can be forced to change by the inclusion of a varactor (a voltage variable capacitor) in the primary resonant loop of the circuit. By applying a DC voltage on this varactor, many oscillators can be tuned over an octave band. In the description above, the oscillator and load pull performance was assuming a fixed frequency (no varactor) circuit. If the load was a fixed length of lossless transmission line and the oscillator frequency was forced by the applied voltage on the varactor as opposed to the load pull phenomena, the "knees" would be seen as the phase seen at the oscillator was swept through 180° because the effect of decreased wavelengths at higher frequencies. The number of knees appearing in the voltage vs frequency plot is dependent upon the dielectric constant of the medium in the transmission line, the length of the line and the frequency.

Figure 22A:
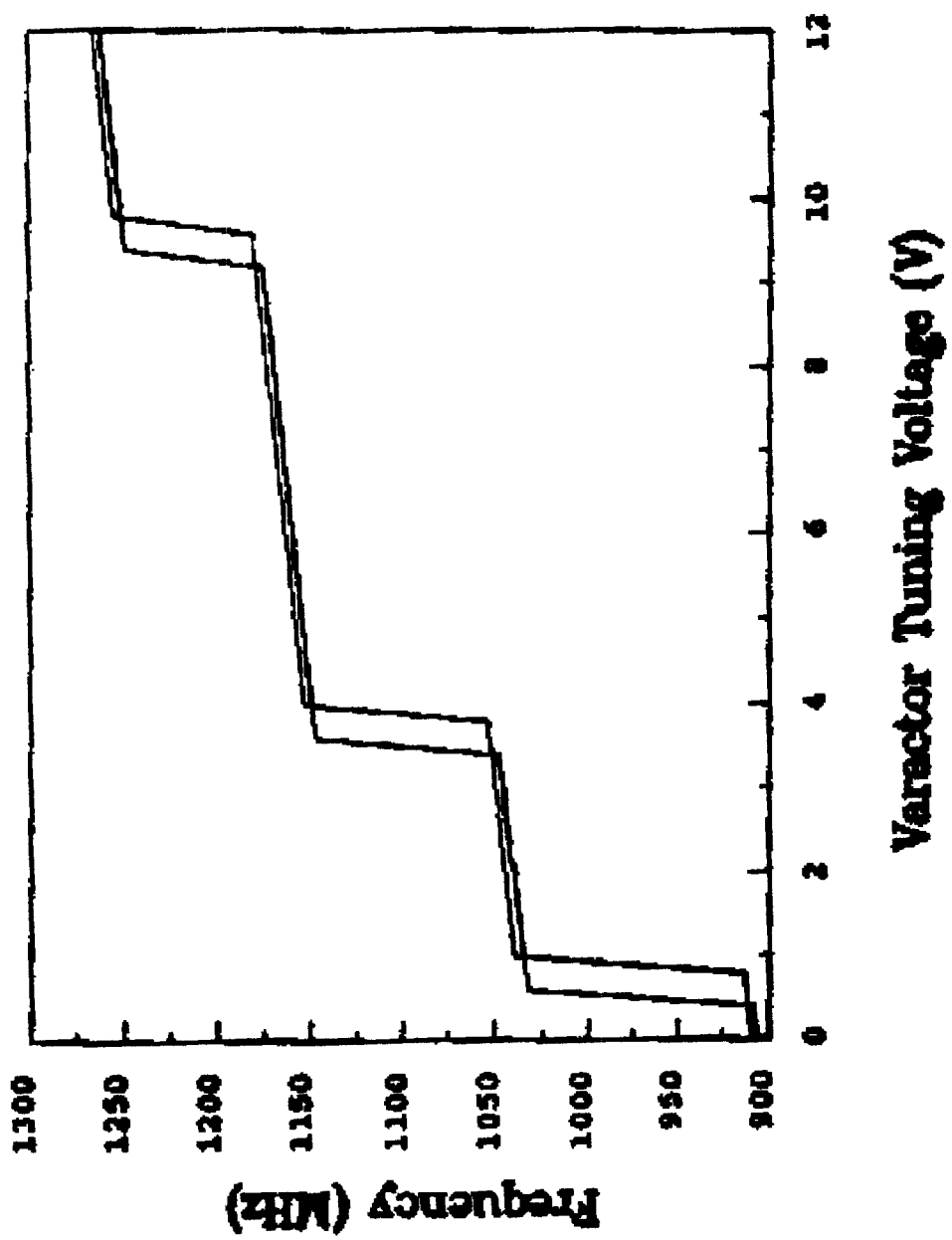
FIG. 22A shows a pair of sample curves of $f_{OSC}$ versus $V_{tun}$, for a system which has been modified.
Figure 22B:
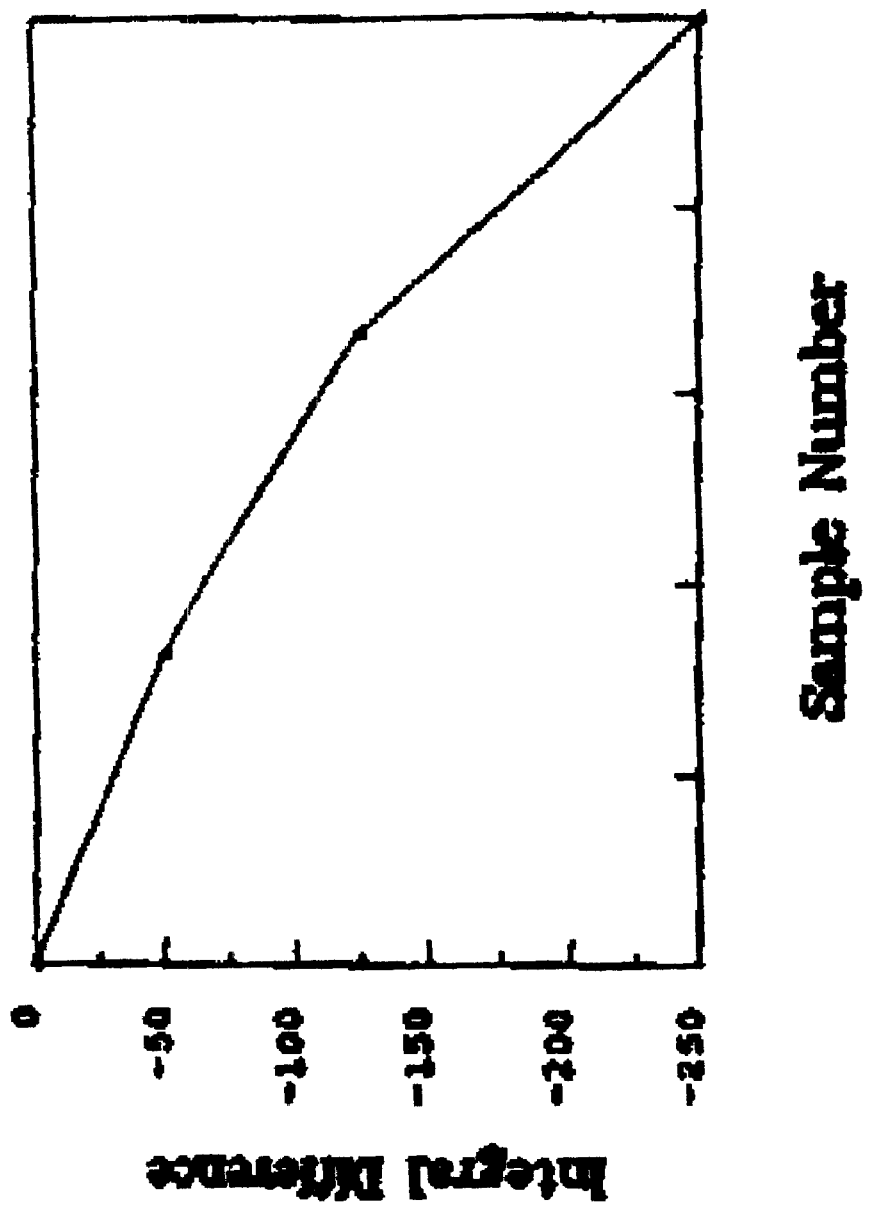
FIG. 22B shows the difference between the derived data parameters corresponding to these curves.

FIG. 22A shows a pair of sample curves of $f_{ose}$ versus $V_{tun}$, for a system which has been modified, and FIG. 22B shows the difference between the derived data parameters corresponding to these curves. Two samples of gasoline with different water contents were measured. An integration of the area under the curved was done for both measurements, and the difference of the integrals was taken. The result is shown in the FINAL RESULT plot. As more knees come into the plot, the integral increases.

Figure 22C:
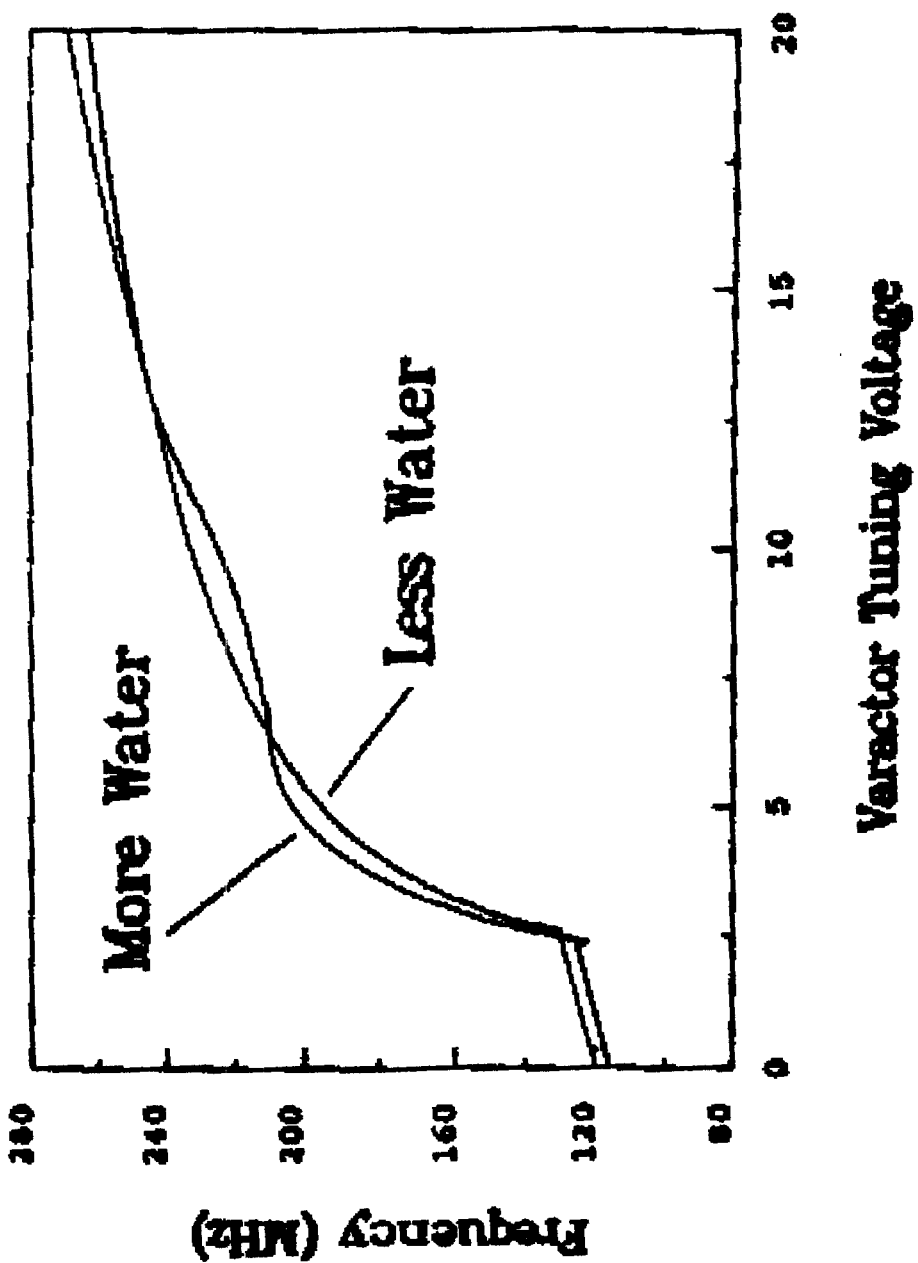
FIG. 22C shows another pair of sample curves of $f_{OSC}$ versus $V_{tun}$, for a highly lossy composition before and after modification.
Figure 22D:
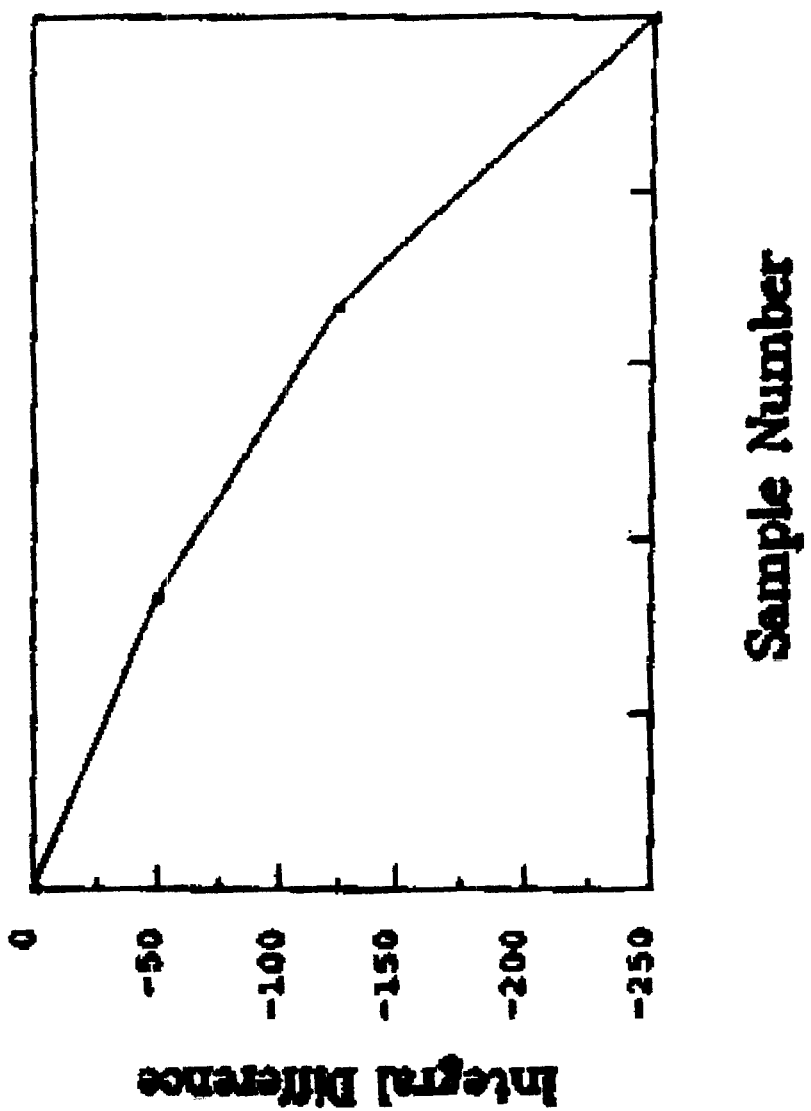
FIG. 22D shows the difference between the derived data parameters corresponding to these curves.

FIG. 22C shows another pair of sample curves of $f_{ose}$ versus $V_{tun}$, for a highly lossy composition (oil in 3% salt water) before and after modification, and FIG. 22D shows the difference between the derived data parameters corresponding to these curves. The knees are not very distinguishable because of the added loss is decreasing the sharpness of the 180 degree phase transitions. However, again the same trend is seen in the difference of the integrals for the two curves.

This technique can be used to eliminate the multiple valued problem that may exist if the oscillator is not a VCO (varactor controlled oscillator). As long as the process is slow enough to allow a sweep, exact values can be reproduced. If the process variable is changing during a sweep the resultant data is an average value of the process during that time interval. This provides for a graceful measurement under any circumstances.

In an alternative class of embodiments, signal processing software is used to look at not only the frequency response, but also the time rate of change and a slope of the frequency as tuning voltage is swept at a constant rate. Both of these factors can provide further differentiated characterizations of both the materials and the baseline chemical. The frequency sweep can thus detect very slow polar moments (KHz variety) even though the system is operating at microwave frequencies. This may especially be true with some of these crystal like structures which will have long relaxation times. It also would be indicative of the amount of "loading" of the planar substrate absorptive material at that particular time.

In the experimental runs given herein, the tuning voltage $V_{tun}$ is typically swept across the whole range shown every 100 milliseconds or so. However, by varying the rate of voltage sweep, phenomena having different relaxation time constants may be distinguished. See generally McCrum et al., ANELASTIC AND DIELECTRIC EFFECTS IN POLYMERIC SOLIDS (1967), which is hereby incorporated by reference. (In production installations, it is generally preferably to simply let the oscillator run at a fixed frequency).

Thus, simple data reduction can be performed to derive a single index number for a given set of conditions. This is particularly useful where a given system is being tracked over time, since the time-domain behavior of the index number can easily be tracked. Thus, for instance, for endpoint detection in monitoring a batch process, the endpoint can be identified when the index value has shifted by a certain percentage from its initial value and the rate of change has declined to a certain percentage of its maximum value during the process run.

Figure 24A:
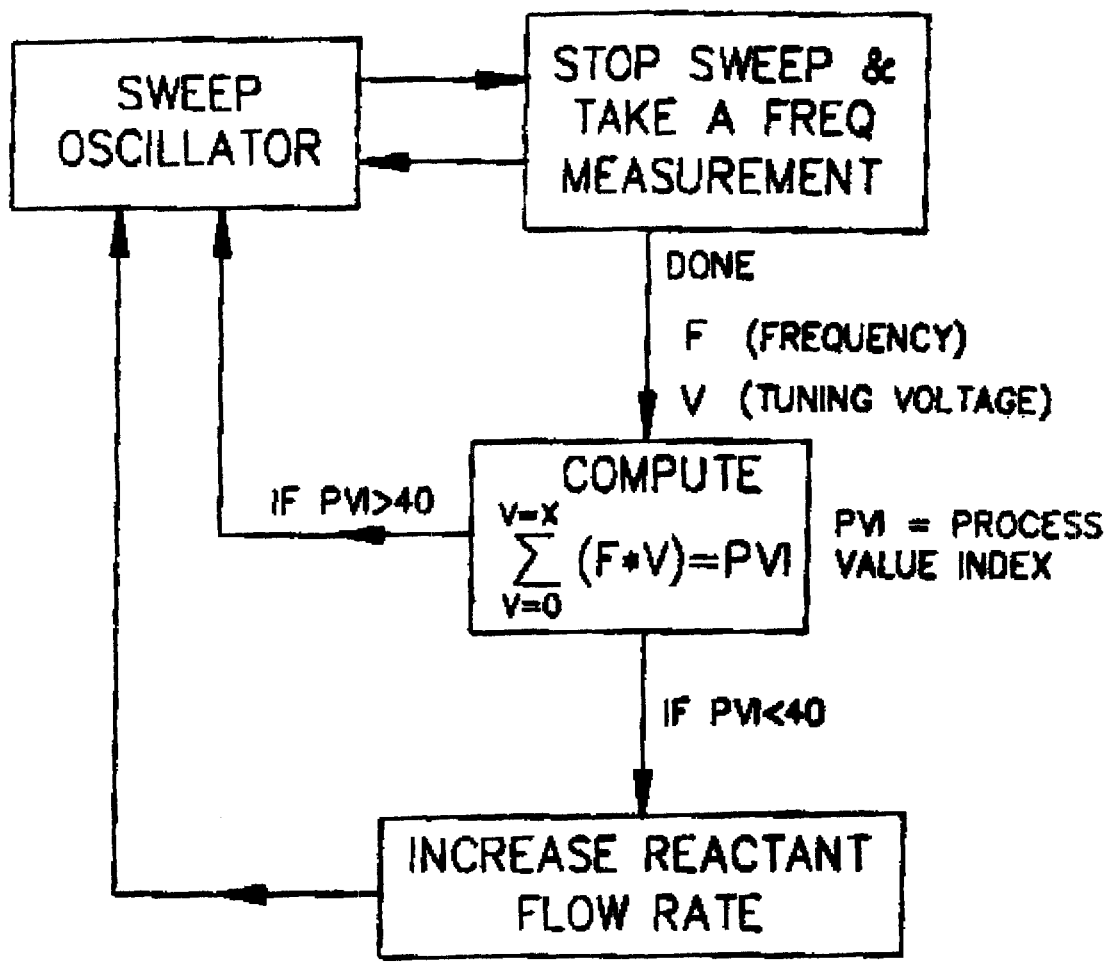
FIG. 24A shows a flow chart for process control based on a "process index" value, derived as in FIGS. 22A–22D, in a simple process example as shown in FIG. 24B.
Figure 24B:
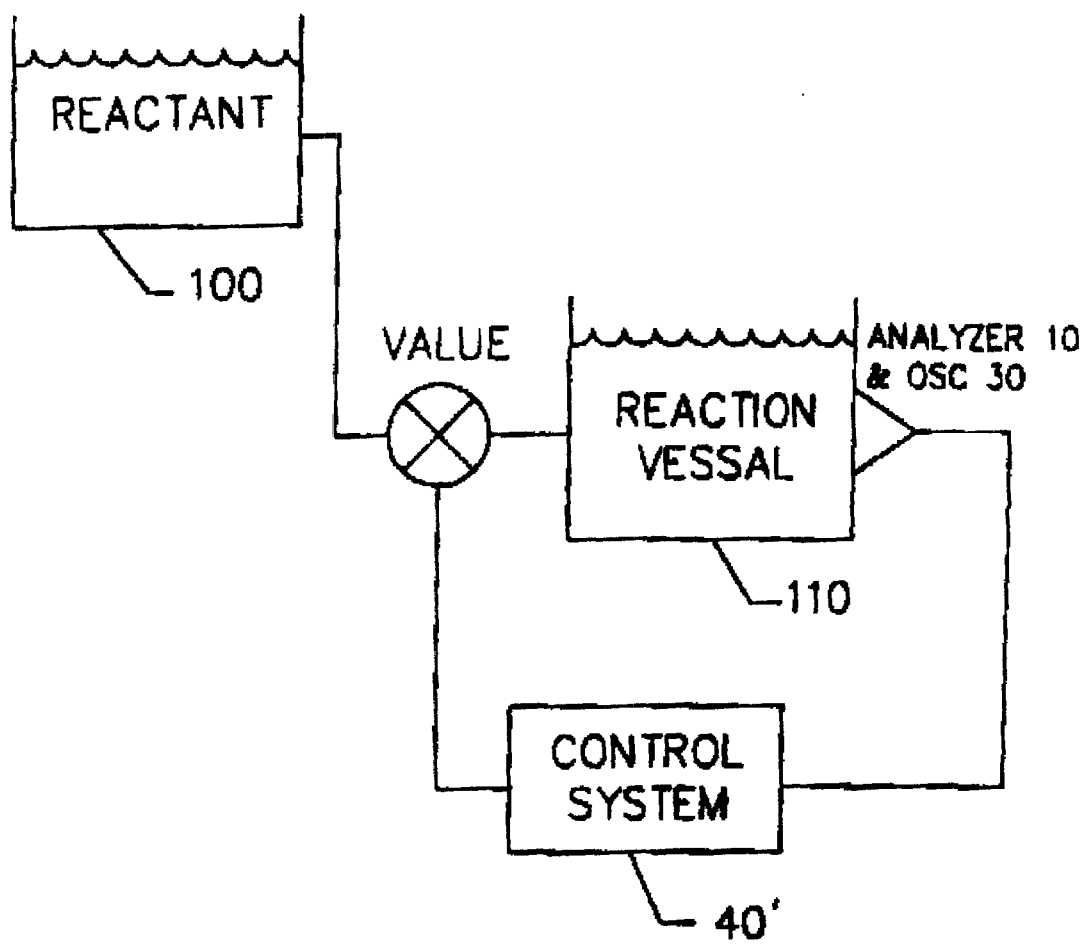

FIG. 24A shows a flow chart for process control based on a "process index" value, derived as in FIGS. 22A–22D, in a simple process example as shown in FIG. 24B. In this example, flow of material 100 into the vessel 110 is controlled in real time by electronics 40', in accordance with the above procedures, using a probe 10 and voltage-controlled oscillator 30.

Monitoring Fermentation Processes

The present application discloses processes for monitoring bulk fermentation, and for partially characterizing the composition of a batch fermentation, by observing the frequency of a load-pull oscillator which is RF-coupled to the material under test (preferably by a simple single-ended RF probe).

Most pharmaceutical fermentations are done in a small batch mode where there is no flow. The planar probe structure is very well adapted to such applications. The planar structure also lends itself to throw away replacements to maintain sensitivities and prevent bacteriological growth in these sensitive vats. Of course, sterile load-lock procedures are preferably used for insertion of a sterile RF probe into a culture vat.

It should be noted that the disclosed methods are not only useful for pharmaceutical applications, but may also be useful in brewing, winemaking, and in food industry processes using biologically active agents.

The disclosed methods also permit the biomass of a fluid stream to be measured. Thus metering of a starter culture can be optimized without waste.

The disclosed methods also provide a direct test for yeast viability in solution. Thus the presence of yeast activity can be checked during the early stages of fermentation, before the yeast mass has multiplied sufficiently to be unmistakably active.

Figure 25A:
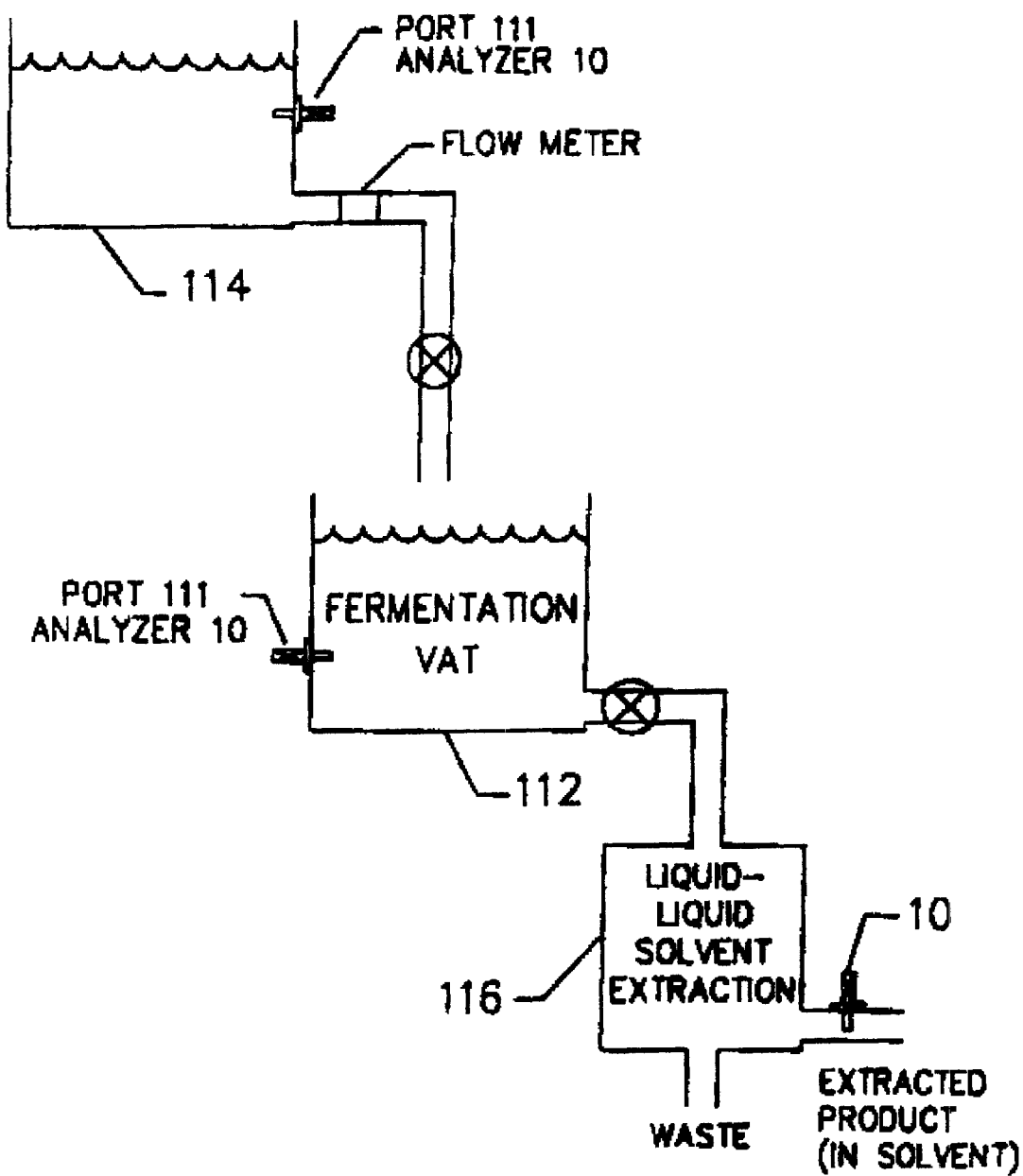
FIG. 25A shows a sample process flow for fermentation monitoring according to the disclosed inventions.
Figure 25B:
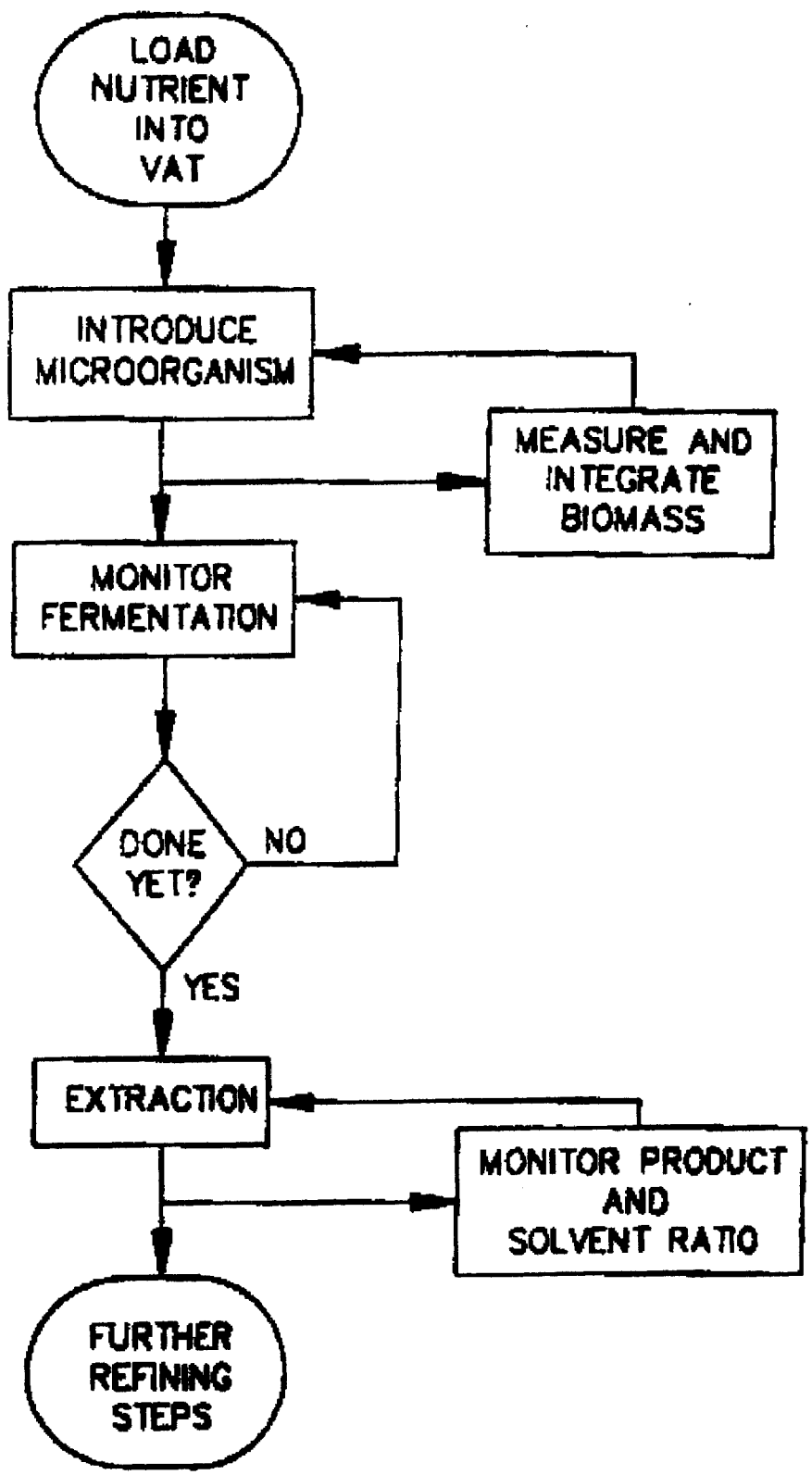
FIG. 25B shows a flow chart for corresponding controls logic, in which the capability of FIG. 25A is used for endpoint detection and yeast viability assurance.

FIG. 25A shows a sample process flow for fermentation monitoring according to the disclosed inventions, and FIG. 25B shows a flow chart for corresponding control logic, in which the capability of FIG. 25A is used for endpoint detection and yeast biomass control.

FIG. 25A shows a typical antibiotic production process. After the fermentation process has gone to completion (or at least begun to slow down), the liquor from the vat 112 is passed to an extraction stage 116, for removal and purification of the desired end-product. For antibiotic extraction, this may be, for example, a liquid-liquid extraction using a methyl actate/heptane solvent. (Of course, the extraction and purification operations can be very complex indeed, and the single stage shown is merely illustrative).

Bio-mass measurements is performed on the organisms as they are introduced into the fermentation tank 112 from the starter stock 114. This permits the amount of the starter culture (which otherwise has to be measured by volume) to be optimized, avoiding unnecessary consumption of the starter culture and also avoiding unnecessary delay in the fermentation process.

An initial measurement is taken on the loaded Fermentation tank 112 to produce a "process signature". This is then used as a baseline to track the progress of fermentation. A load-pulled oscillator, connected to the probe 10 at port 111, is then used to monitor progress of the fermentation, and to determine when to transfer the liquor to the extraction column.

In the embodiment shown, additional probe interfaces 10 are located before and after the extraction column 116, to provide a measure of column up-take efficiency. This permits the user to accurately optimize the trade-off between efficient use of solvent and efficient extraction of product.

Figure 25C:
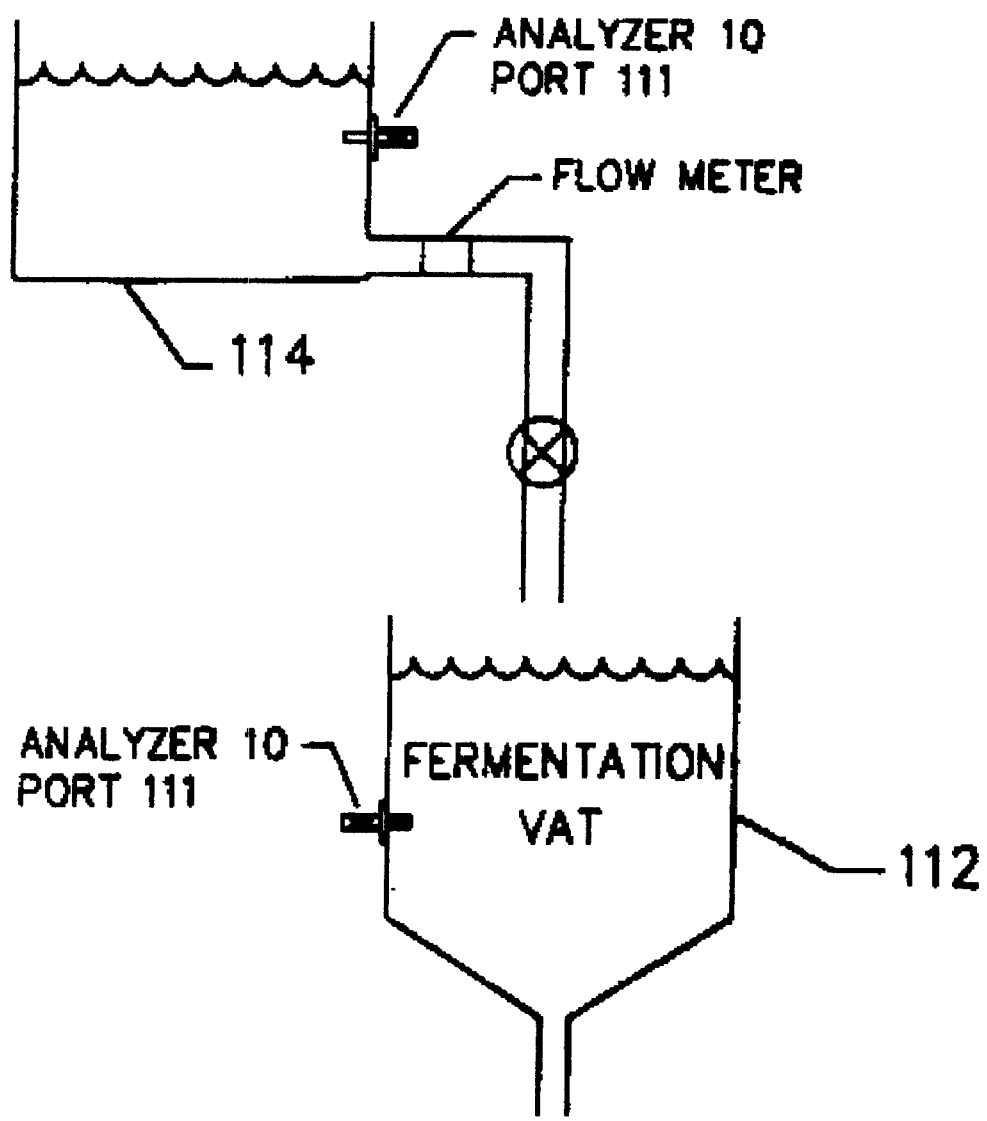
FIG. 25C shows a fermentation process for sugar conversion.
Figure 25D:
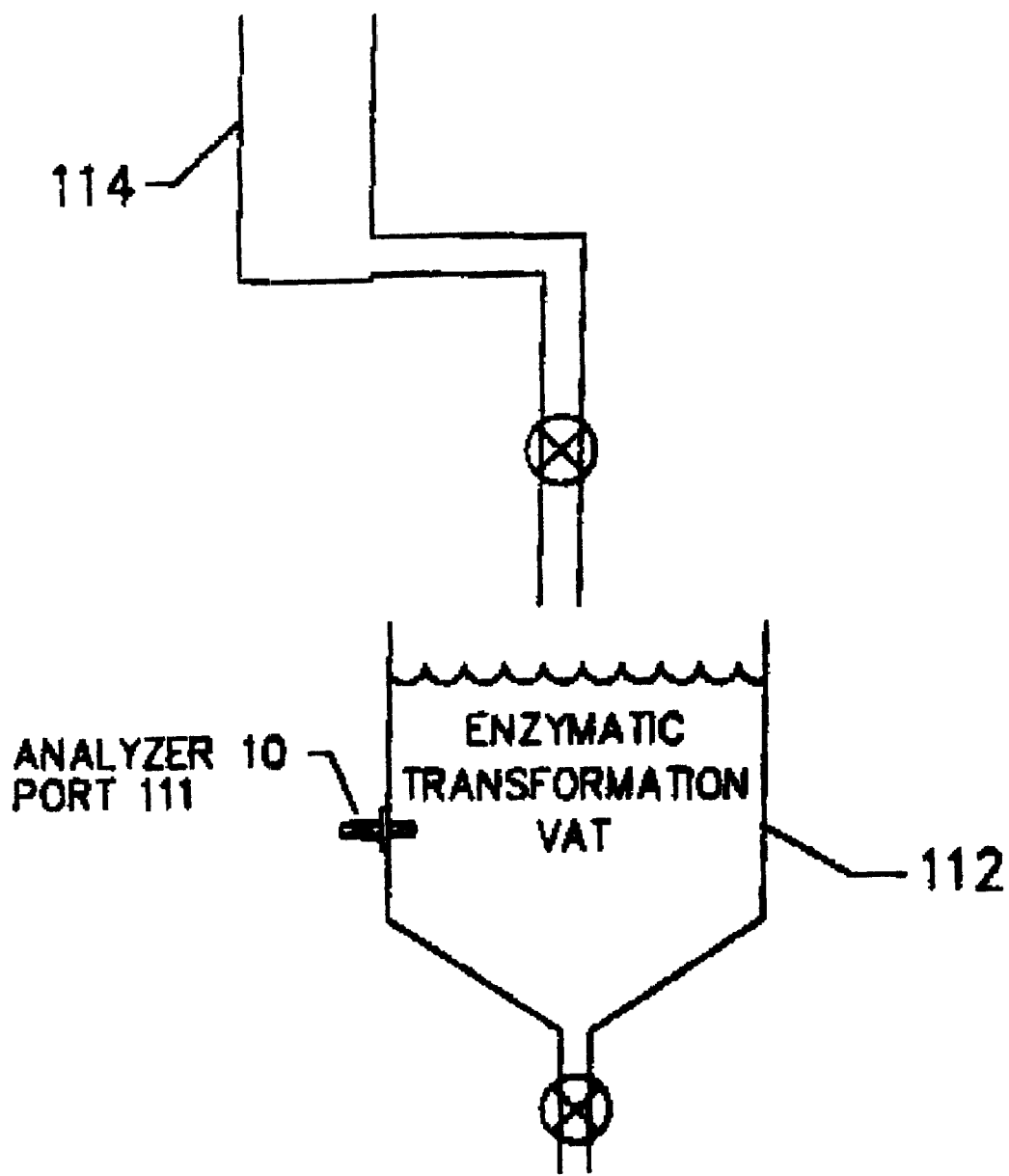
FIG. 25D shows an enzymatic modification process.

FIG. 25C shows a fermentation process for sugar conversion, and FIG. 25D shows an enzymatic modification process. In this process glucose Isomerase is used to convert into a glucose+fructose mixture ("HFSC"). Control logic like that of FIG. 25B can be analogously applied, mutatis mutandis, to these cases too.

Figure 18A:
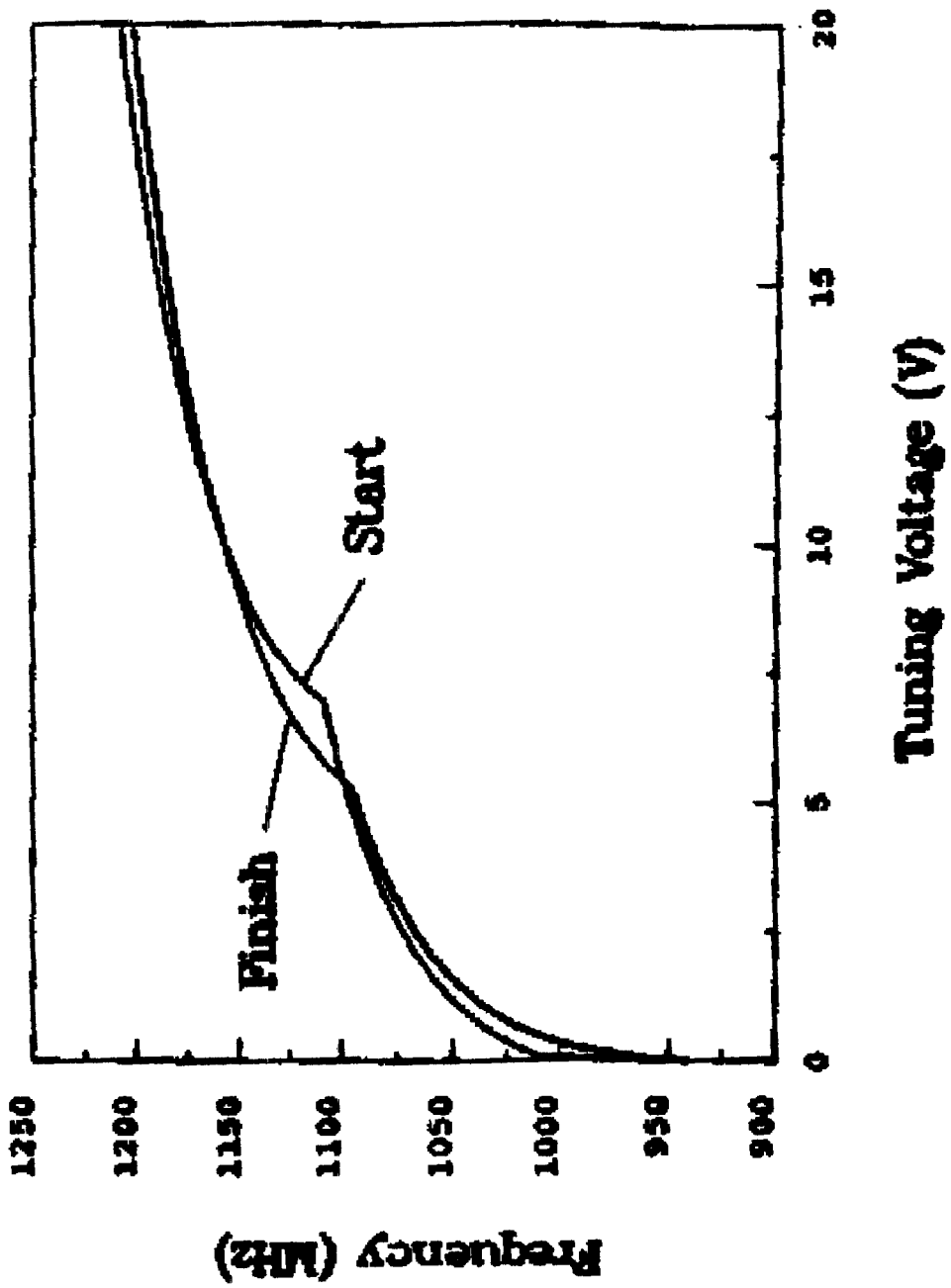
FIG. 18A shows actual measured results from monitoring a fermentation process, using a planar probe.

FIG. 18A shows actual measured results from monitoring a fermentation process, using a planar probe. The trials of FIGS. 18A and B were performed with 500 ml $H_2O$ at 45° C., using 2.5 g dry yeast and 10 g fructose. The yeast used was standard dried baking yeast packaged for consumer use. The yeast was initially started in a portion of the warm water, and then all ingredients were combined. The curve marked "start" shows an initial measurement after mixing the yeast starter culture into the nutrient solution. In this curve the oscillator frequency goes from about 1162 MHz to about 1182 MHz as the tuning voltage is ramped from about 3.5 V to 6.6 V. Fermentation was then performed for 12 hours. The curve marked "finish" shows another set of measurements which were then taken. In this curve the oscillator frequency goes from about 1162 MHz to about 1218 MHz as the tuning voltage is ramped from 3.5 V to 6.6 V.

Figure 18B:
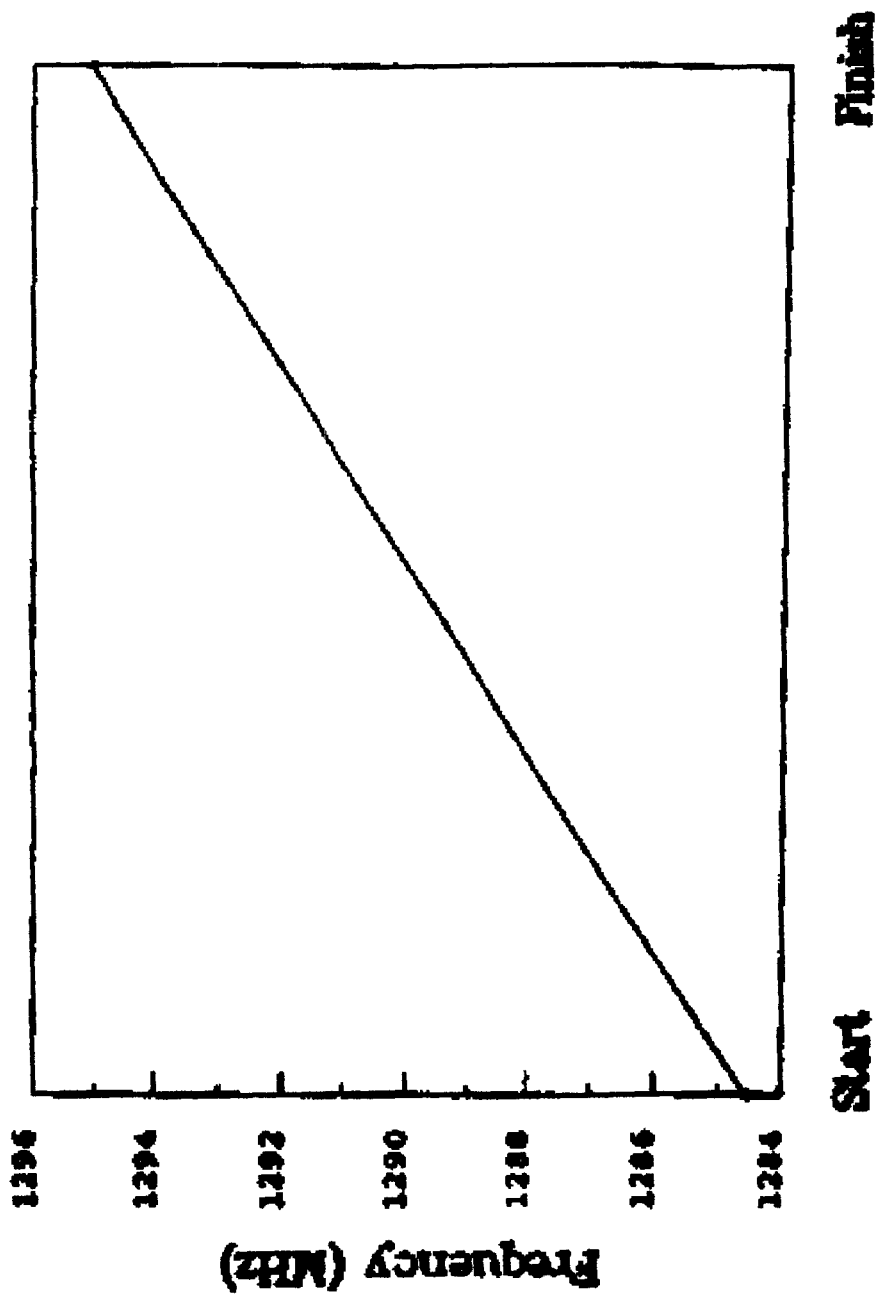
FIG. 18B is an expanded plot of some key data points from the plot of FIG. 18A.

FIG. 18B is an expanded plot of data points from the plot of FIG. 18A at a constant $V_{tun}$=20 V. (The numbers on the X-axis of this plot are insignificant; this plot is merely a graphic way to indicate the large observed difference in oscillator frequency at a given tuning voltage. By dividing this observed frequency difference by the frequency resolution of 30 Hz, it may be seen that the plotted difference is many times the least-measurable-increment).

Applications of the Phase Transition Model to Intact Cells

It has been known for many years that when dry organisms such as yeast cells and seeds and pollen of plants are placed in cold water, they lead their contents into the water and are killed. (It has been reported that the reason for this effect has been reported to be identical to the mechanism explained above for liposomes (32–34). Dry baker's yeast, for instance, must be rehydrated above about 40° C. Below that temperature, the cells leak their contents during rehydration and are killed. However, if the dry cells are placed in water >40° C., their membrane phospholipids undergo a phase transition during rehydration.

Figure 17A:
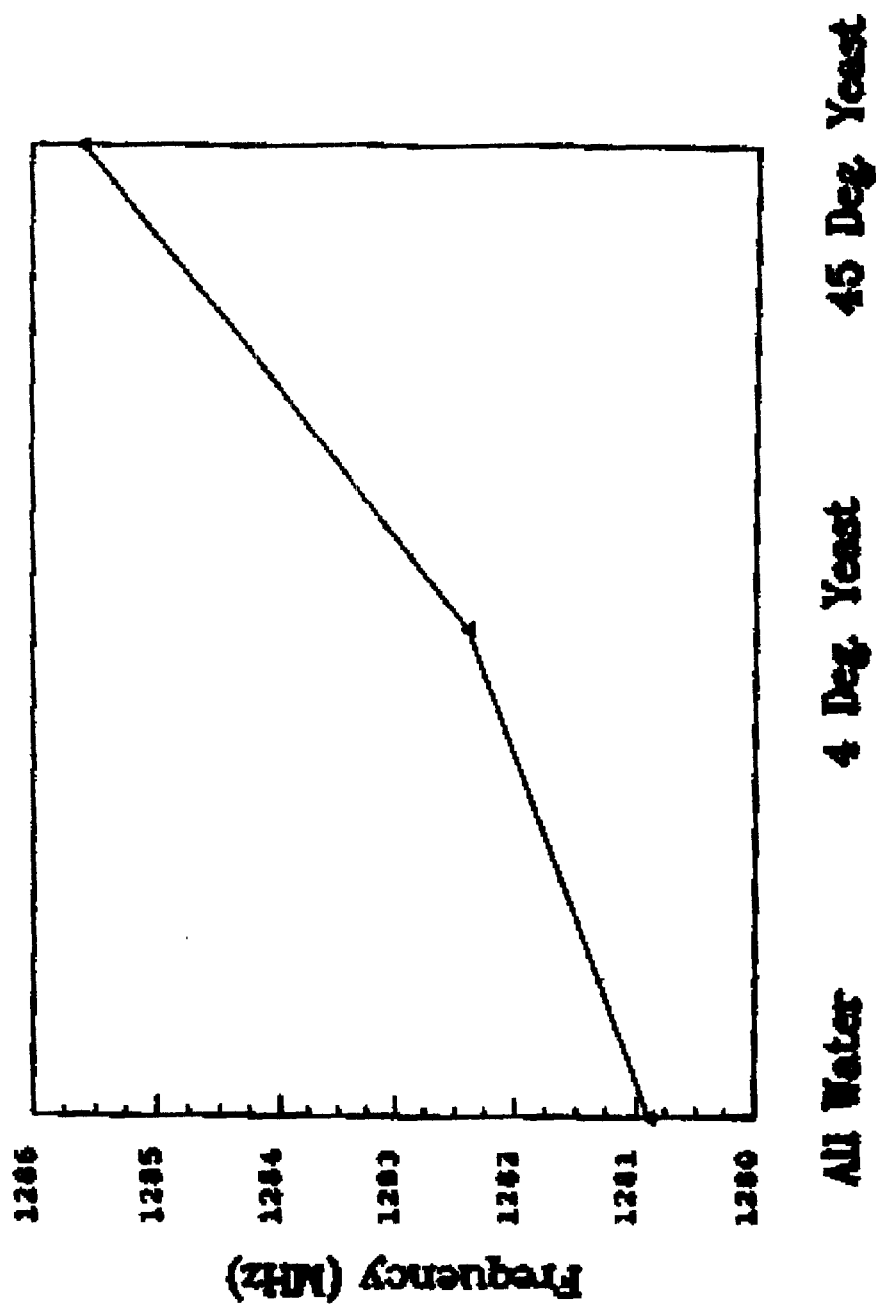
FIG. 17A shows a biomass determination is which the presence of live yeast is readily distinguished from the presence of dead yeast.
Figure 17B:
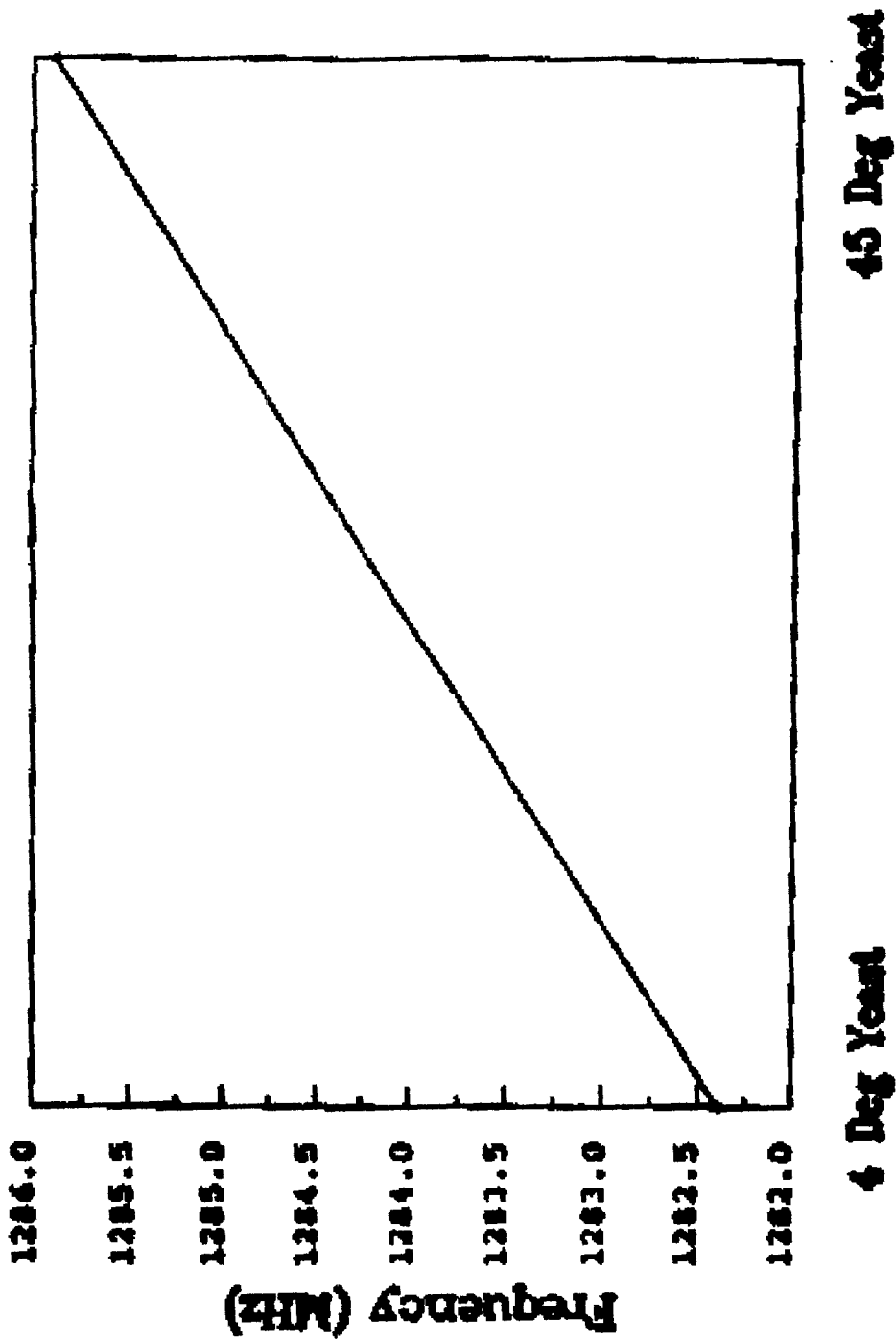
FIG. 17B is an expanded plot of some key data points from the plot of FIG. 17A.

FIG. 17A shows a biomass determination, in which the presence of live yeast is readily distinguished from the presence of dead yeast. In the experimental setup , 5 grams of yeast was mixed with 200 ml of $H_2O$ to produce a 2.4% solution (5/205). This was measured at 30° C. after yeast was mixed in two runs at 4° C. and 45° C. (Mixture at 4° C. kills the yeast.) A measurement of pure water was also taken for comparison. At a fixed tuning voltage of 20 V, the oscillator frequency was 1280.93 MHz for pure water, 1282.48 MHz for water with dead yeast, and 1285.4 MHz for water with live yeast. FIG. 17B is an expanded plot of some key data points from the plot of FIG. 17A. The numbers on the X-axis of this plot are insignificant; this plot is merely a graphic way to indicate the large observed difference in oscillator frequency at a given tuning voltage. By dividing this observed frequency difference by the frequency resolution of 30 Hz, it may be seen that the plotted difference is about 100,000 times the least-measurable-increment. Thus, it may be seen that load-pulled measurement provides sensitive discrimination between equal concentrations of live and dead yeast, and thus provides a technique for direct measurement of biomass.

Monitoring Curing and Crystallization Processes

The present application discloses processes for monitoring the state of curing (or microcrystalline change) of solid materials, by observing the frequency of a load-pull oscillator which is RF-coupled to the material under test (preferably by a simple single-ended RF probe).

One area where this technique is of particular interest is in monitoring the curing of shaped aerodynamic composite materials.

Figure 26A:
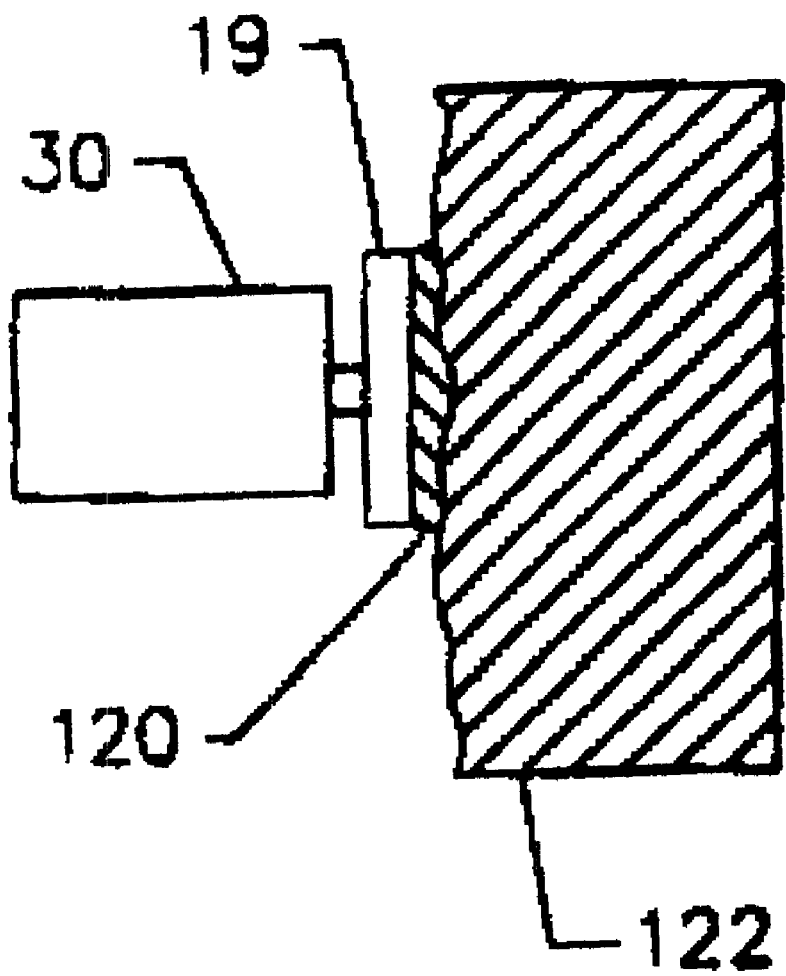
FIG. 26A shows a sample setup for monitoring of material curing according to the disclosed invention.
Figure 26B:
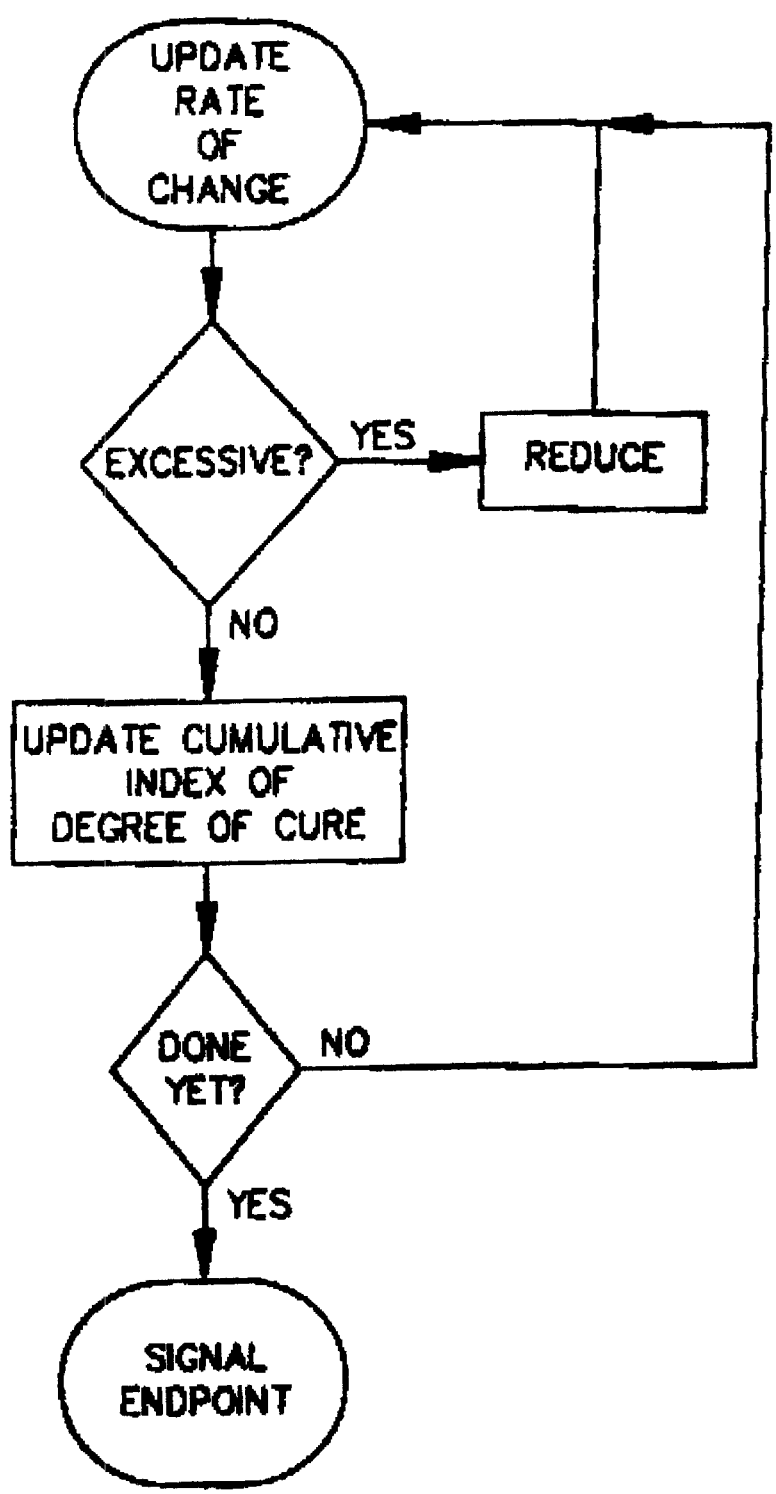
FIG. 26B shows a flow chart for corresponding control logic, in which the capability of FIG. 26A is used for control of curing rate end also for endpoint detection.

FIG. 26A shows a sample setup for monitoring of material curing according to the disclosed inventions, and FIG. 26B shows a flow chart for corresponding control logic, in which the capability of FIG. 26A is used for control of curing rate and also for endpoint detection. In the setup of FIG. 26A, a gel 120 is preferably used to provide reliable contact and good coupling between a single-ended probe (e.g. a patch probe 19) and a formed body 122 of material undergoing cure.

Another area of particular interest is in monitoring the curing of concrete and cement compositions. Cement curing is a complex process which requires a fairly extended period. In curing Portland cement (and related compounds), it is generally desirable not to cure too rapidly. Dendritic crystalline growth occurs during the normal curing process, and the interpenetration and interlocking of the resulting crystallites gives the final material its strength. If curing is performed too rapidly, this interpenetration will not occur, and the material will be weaker.

To meet this need, the present application also provides methods for monitoring and controlling the rate of cure of composite materials. When the real-time monitoring process indicates that the rate of cure is excessive, then steps are taken to reduce the rate of cure (normally by lowering the temperature).

Where it is required merely to detect the endpoint of a curing process, a useful alternative is to use rate-of-change measurements instead of (or in combination with) absolute measurement.

Figure 13:
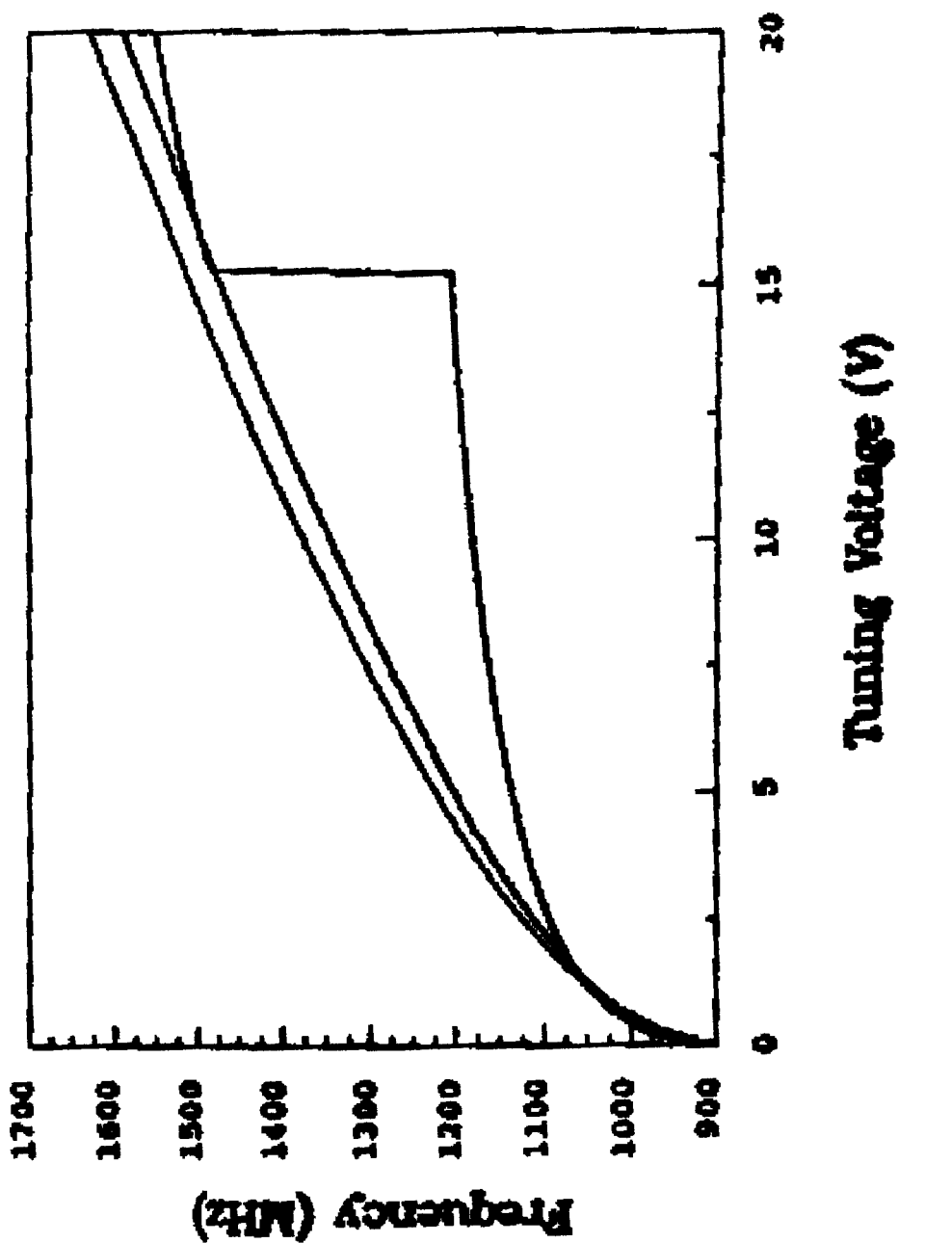
FIG. 13 shows actual measured results trap monitoring microcrystalline changes during setting of a cement slurry. Various time intervals was were used as induced by the drawing.

FIG. 13 shows actual measured results from monitoring microcrystalline changes during setting of a cement slurry. Various time intervals were used as indicated by the drawing. The curve marked "start" actually includes multiple traces, taken at 30 second intervals; but at this point the shift in properties is sufficiently slow that the different traces cannot be separated by eye on the plot shown. In this curve the oscillator frequency goes from about 1127 MHz to about 1283 MHz as the tuning voltage is ramped from 2.2 V to 13.2 V. The second group of curves, taken at 5 minute intervals 30 minutes after beginning, shows some separation of the individual traces at the higher tuning voltages. In this Figure the oscillator frequency goes from about 1120 MHz to about 1262 MHz as the tuning voltage is ramped from 2.2 V to 13.2 V. (Note too that a significant spread is seen among the 5-minute-separated runs at the higher tuning voltages). The last trace, taken 7 days later, shows the markedly different properties of the solidified material. In this curve the oscillator frequency goes from about 1155 MHz to about 1192 MHz as the tuning voltage is ramped from 2.2 V to 13.2 V.

Food Analysis and Food Process Monitoring

The present application discloses processes for monitoring the state of processing of, and for partially characterizing the composition of, food and feed products, by observing the frequency of a load-pull oscillator which is RF-coupled to the material under test (preferably by a simple single-ended RF probe).

The simplest way to use this monitoring technique analytically is to look at the time derivative of the measured RF frequencies: a certain percentage decrease in the rate of change can be used for an endpoint signal, to terminate a batch cooking stage. (Of course, this percentage decrease would be customized for a particular process, and would allow for continued cooking as the temperature of the food materials is ramped down.)

Figure 27A:
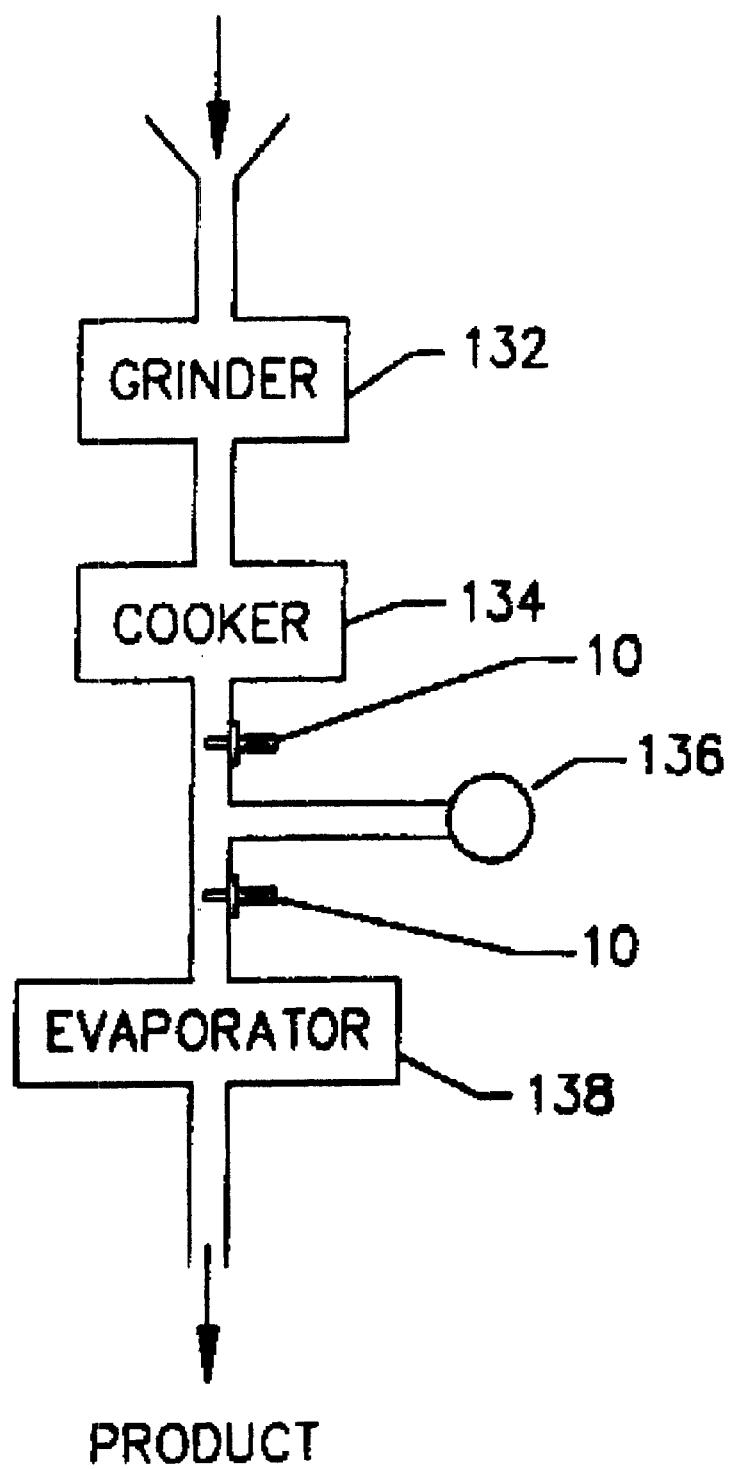
FIG. 27A shown a simple process flow for monitoring of food processing according to the disclosed inventions.
Figure 27B:
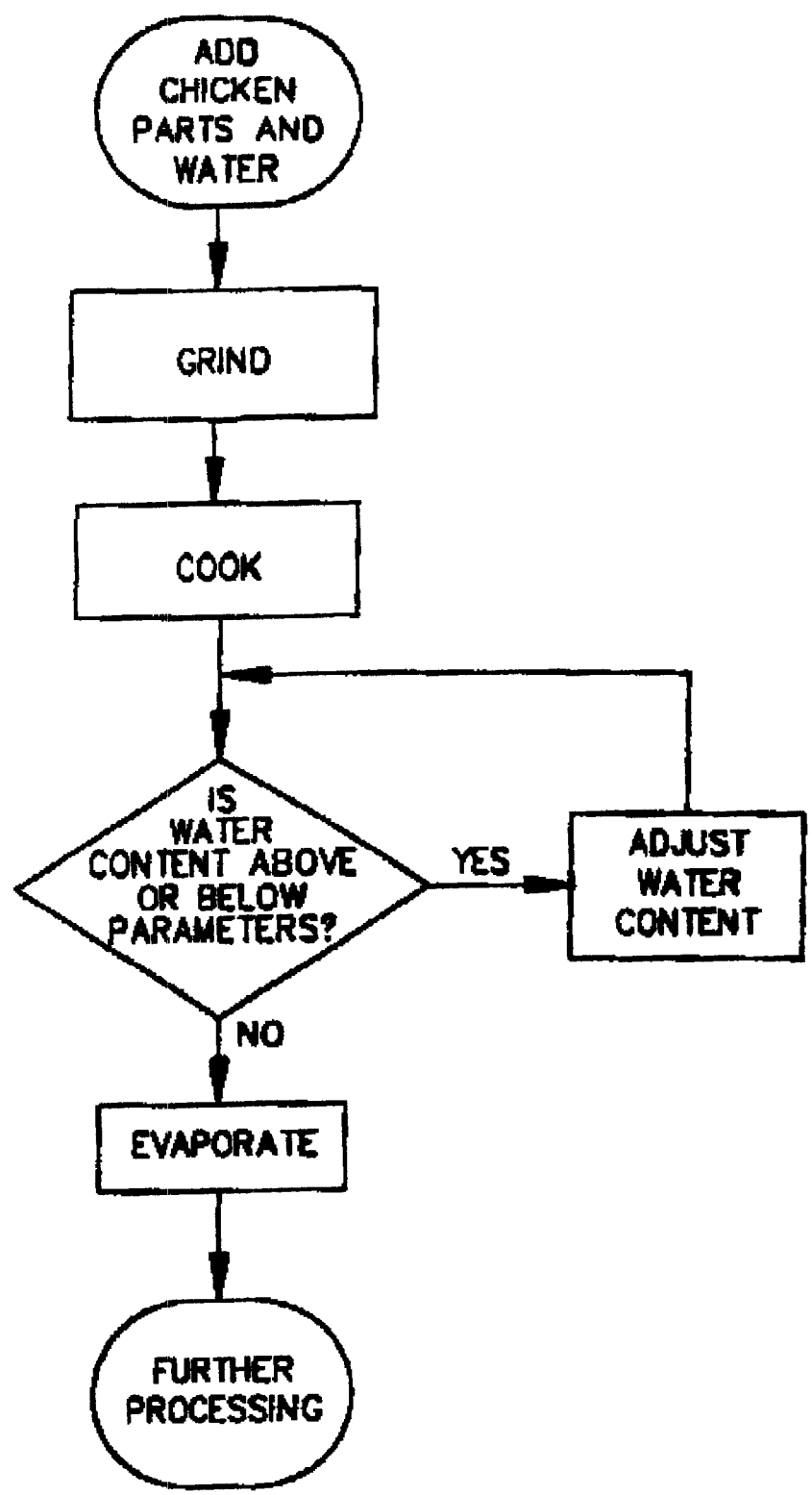
FIG. 27B shows a flow chart for corresponding control logic.

FIG. 27A shows a simple process flow for monitoring of food processing according to the disclosed inventions, and FIG. 27B shows a flow chart for control logic corresponding to FIG. 27A. In this sample flow, animal parts are fed through grinder 132 and cooker 134 to evaporator 138. The water injector 136 is regulated, using measured data from the probe 10, to achieve a water content into the evaporator of 40 to 50%. (Too low water content will cause the evaporator to clog; too high a water content will waste energy in the evaporator).

Figure 14A:
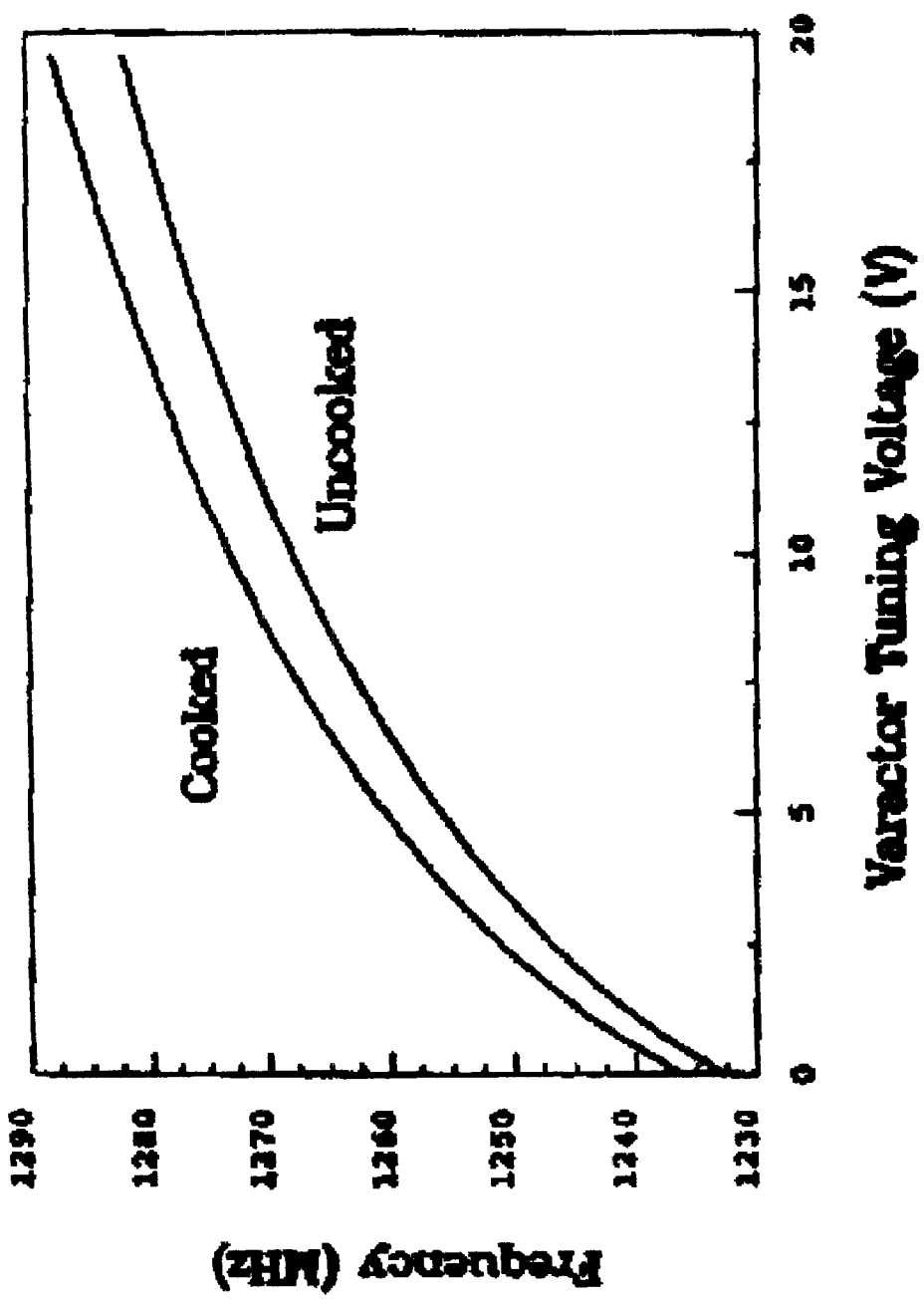
FIG. 14A shows actual measured results from monitoring conformational changes (molecular expansion) of xanthan from thermal treatment, using a bare planar probe.
Figure 14B:
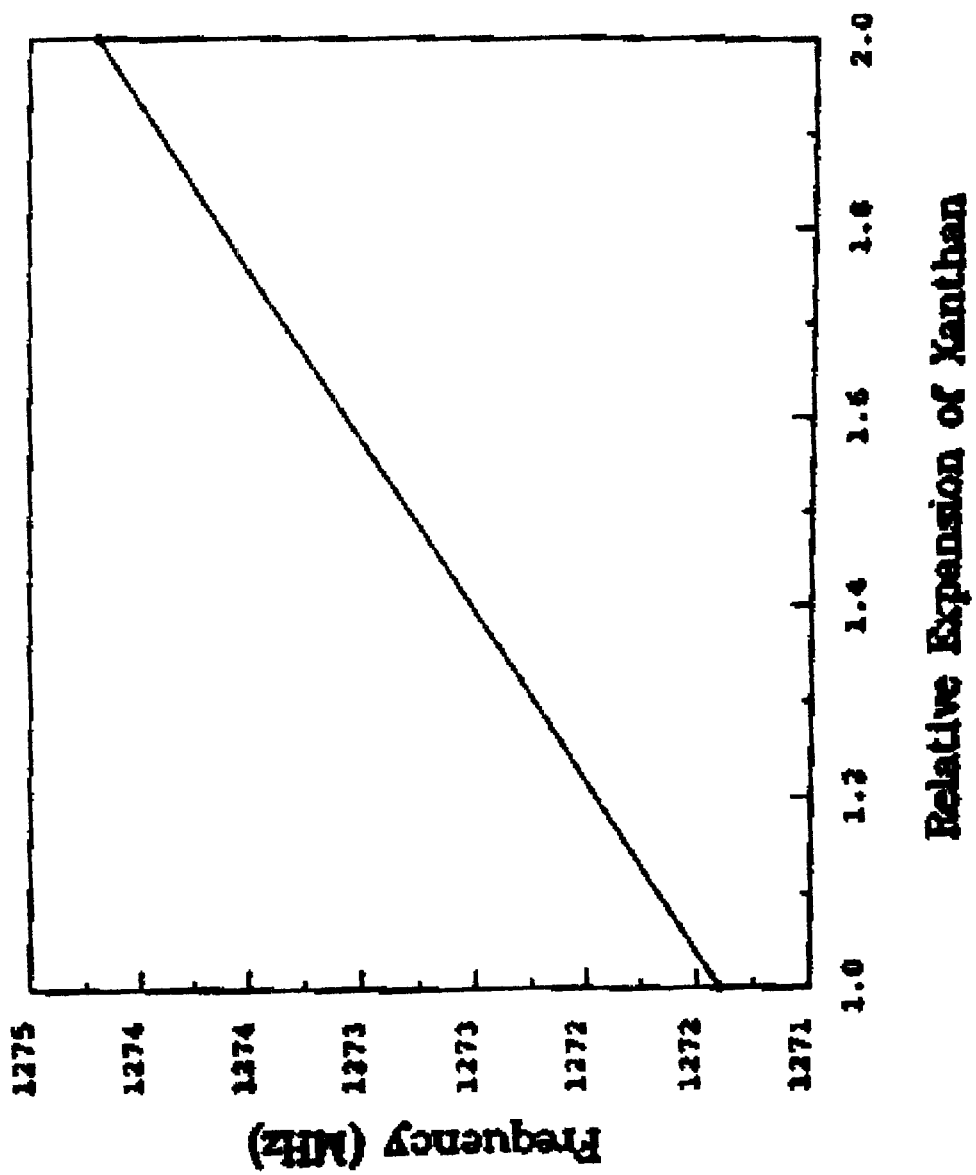
FIG. 14B is an expanded plot of some key data points from the plot of FIG. 14A.

FIG. 14A shows actual measured results from monitoring conformational changes (molecular expansion) of xanthan from thermal treatment, using a bare planar probe. The bottom curve shows uncooked material. In this Figure the oscillator frequency goes from about 1233 MHz to about 1271.4 MHz as the tuning voltage is ramped from 10 V to 20 V. In this curve the oscillator frequency goes from about 1233.4 MHz to about 1274.2 MHz as the tuning voltage is ramped from 10 V to 20 V. FIG. 14B is an expanded plot of some key data points from the plot of FIG. 14A. (The numbers on the X-axis of this plot are insignificant; this plot is merely a graphic way to indicate the large observed difference in oscillation frequency of a given tuning voltage. By dividing this observed frequency difference by the frequency resolution of 30 Hz, it may be seen that the plotted difference is many times the least-measurable-increment.)

Figure 14C:
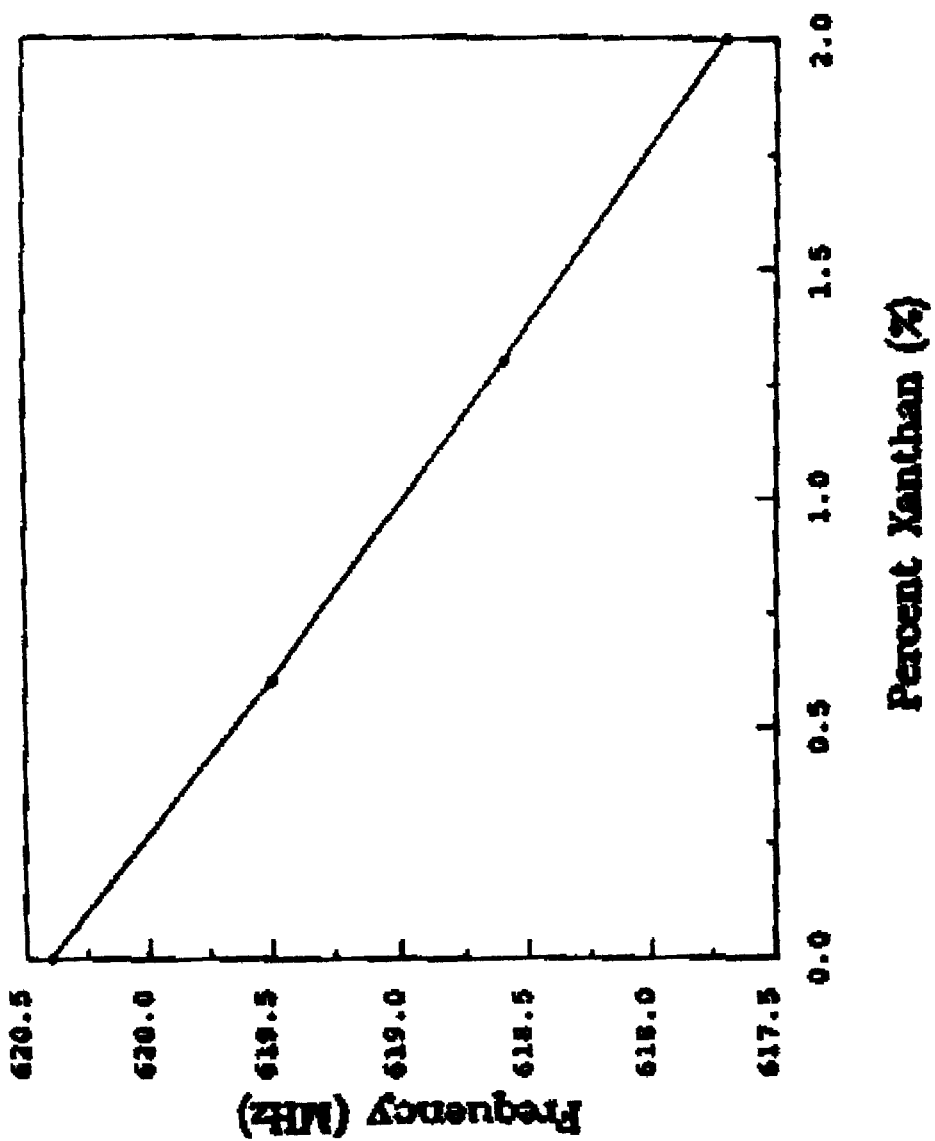
FIG. 14C is a plot showing measurement of the concentration of xanathan in water.

FIG. 14C is a plot showing measurement of the concentration of xanthan in water. In this curve the oscillator frequency goes from about 620.55 MHz to about 617.7 MHz as the concentration of xanthan is varied from 0% to 2.0%.

Figure 14D:
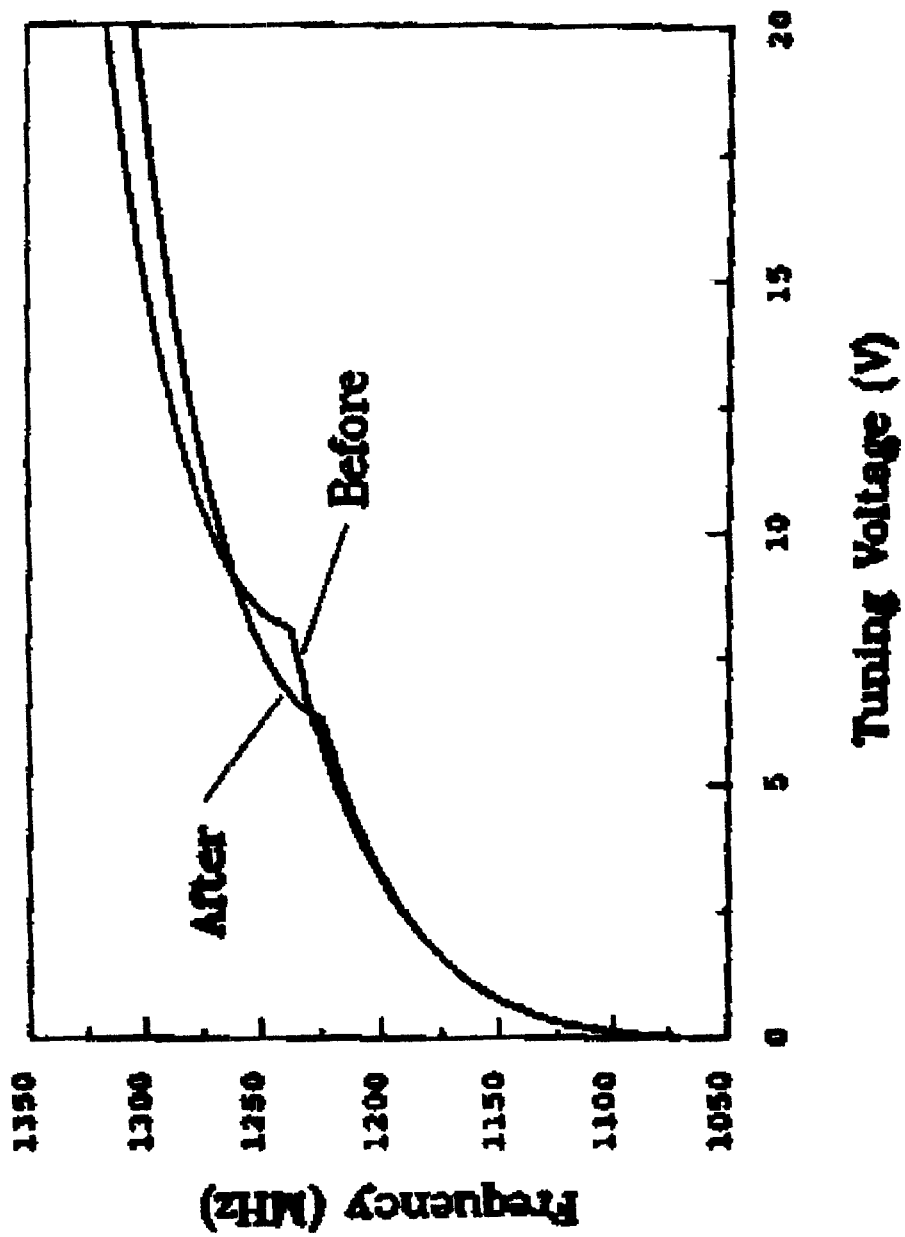
FIG. 14D shown actual measured results from monitoring conformational changes (molecular expansion) of starch from thermal treatment, using a bare planar probe.

Xanthan is a polysaccharide which is in some ways analogous to starch. Similar measurements of starch under heat treatment have yielded curves similar to those of FIGS. 14A and 14B. FIG. 14D shows actual measured results from monitoring conformational changes (molecular expansion) of starch from thermal treatment, using a bare planar probe. In this process a 7% solution of starch was heated for 20 minutes at 70° C. The measurement was performed at room temperature. The curve marked "before" shows starch which has not undergone the conformational changes induced by heat treatment; in this curve the oscillator frequency goes from about 1240 MHz to about 1255 MHz as the tuning voltage is ramped from 8 V to 10 V. The curve marked "after" shows starch which has been cooked. In this curve the oscillator frequency goes from about 1240 MHz to about 1246 MHz as the tuning voltage is ramped from 8 V to 10 V. The bottom curve is a measurement of reflected power, and shows the general shaped of an insertion loss measurement.

Figure 14E:
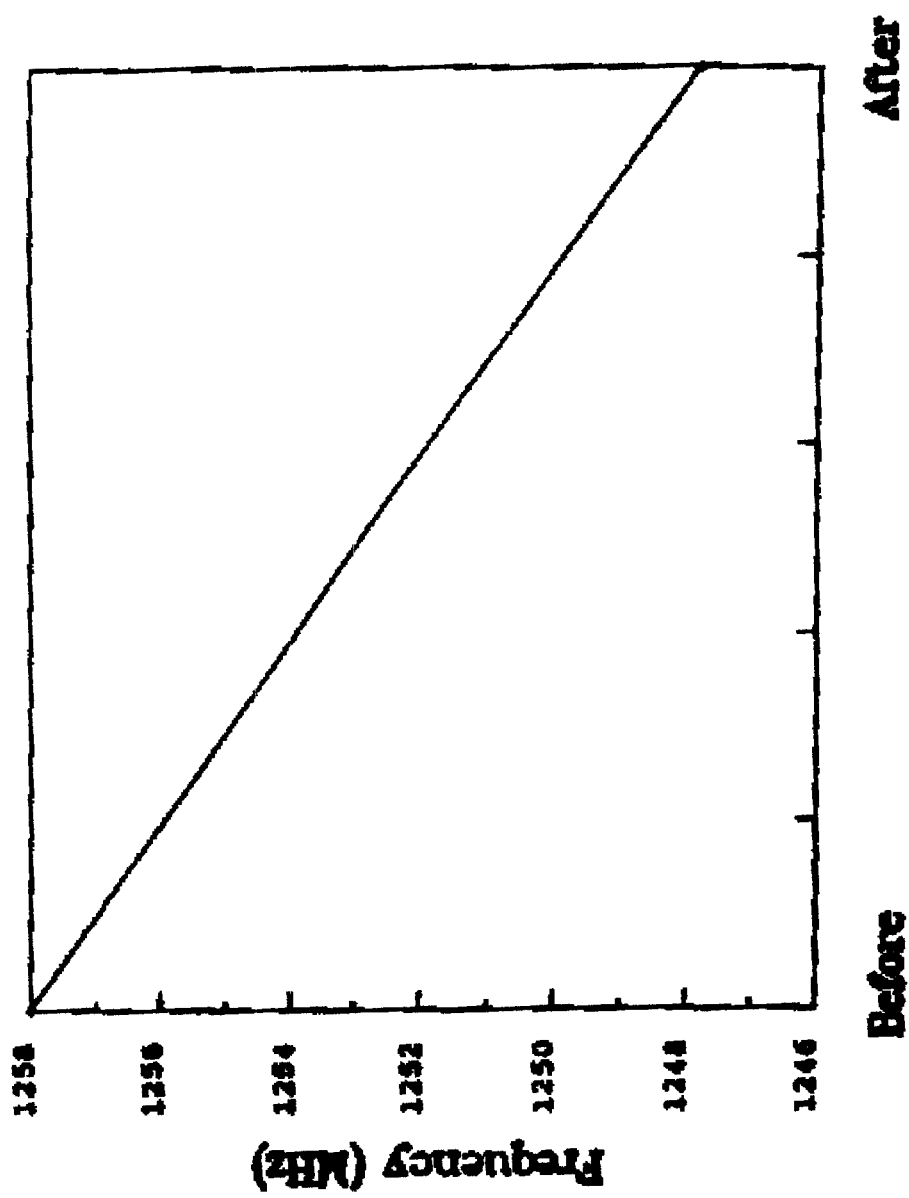
FIG. 14E is an expanded plot of some key data points from the plot of FIG. 14D.

FIG. 14E is an expanded plot of some key data points from the plot of FIG. 14D. (The numbers on the X-axis of this plot are insignificant; this plot is merely a graphic way to indicate the large observed difference in oscillator frequency at a given tuning voltage. By dividing this observed frequency difference by the frequency resolution of 30 Hz, it may be seen that the plotted difference is many times the least-measurable-increment.)

Figure 15A:
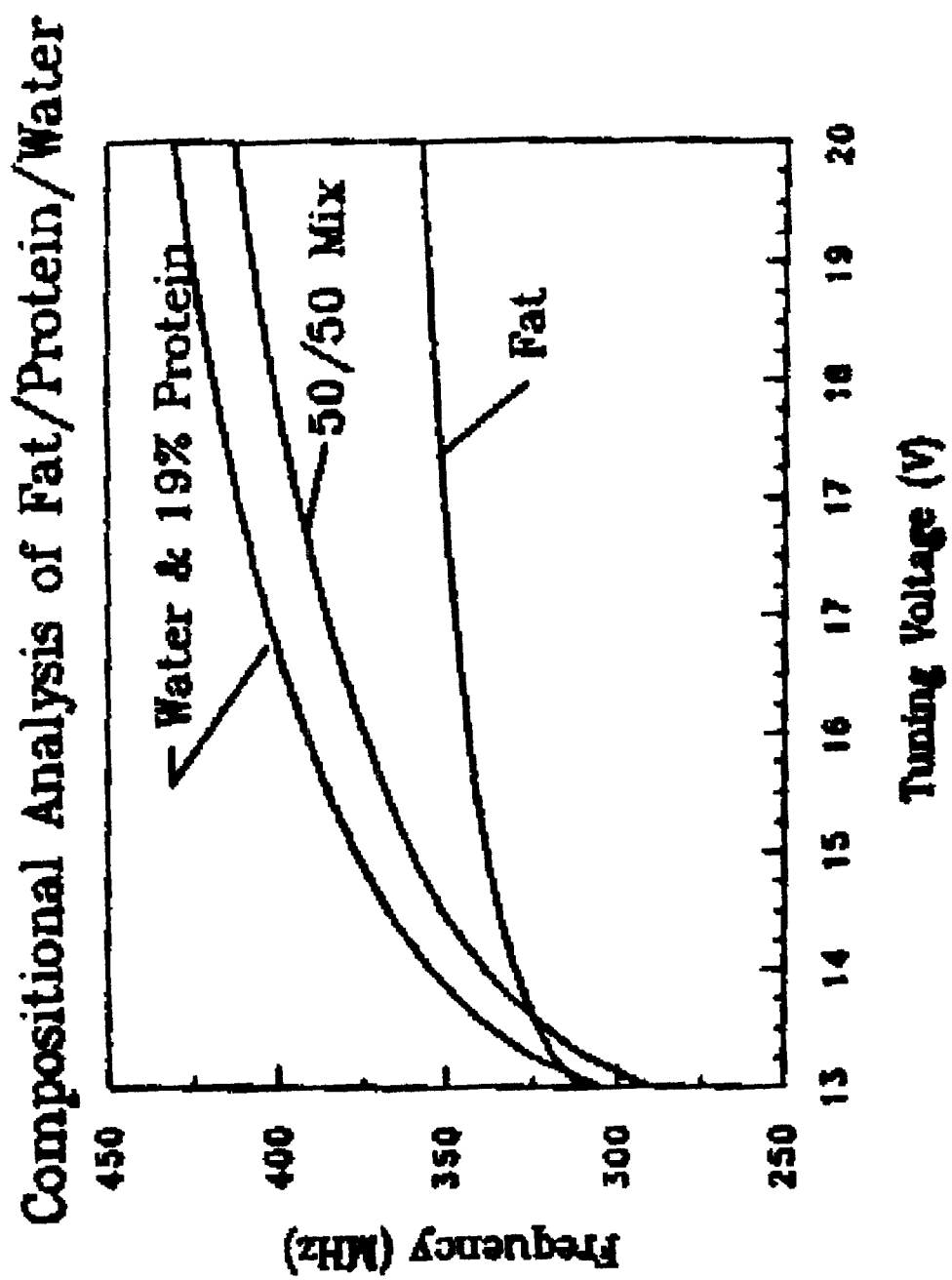
FIG. 15A shown actual data from compositional measurement of a mixture of water with animal protein and fat, using a tapered planar probe with a sheath cover.

FIG. 15A shows actual data from compositional measurement of various mixtures of water with animal protein and fat, using a tapered planar probe with a cover. The top curve shows measurement of a mixture of protein alone (19% wt protein in water). In this curve the oscillator frequency goes from about 391 MHz to about 439 MHz as the tuning voltage is ramped from 13 V to 20 V. The middle curve shows measurements of an equal mixture of the protein solution of the first curve with chicken fat. In this curve the oscillator frequency goes from about 390 MHz to about 430.5 MHz as the tuning voltage is ramped from 13 V to 20 V. The bottom curve shows measurement of pure chicken fat. In this curve the oscillator frequency goes from about 391 MHz to about 400 MHz as the tuning voltage is ramped from 13 V to 20 V.

Figure 15B:
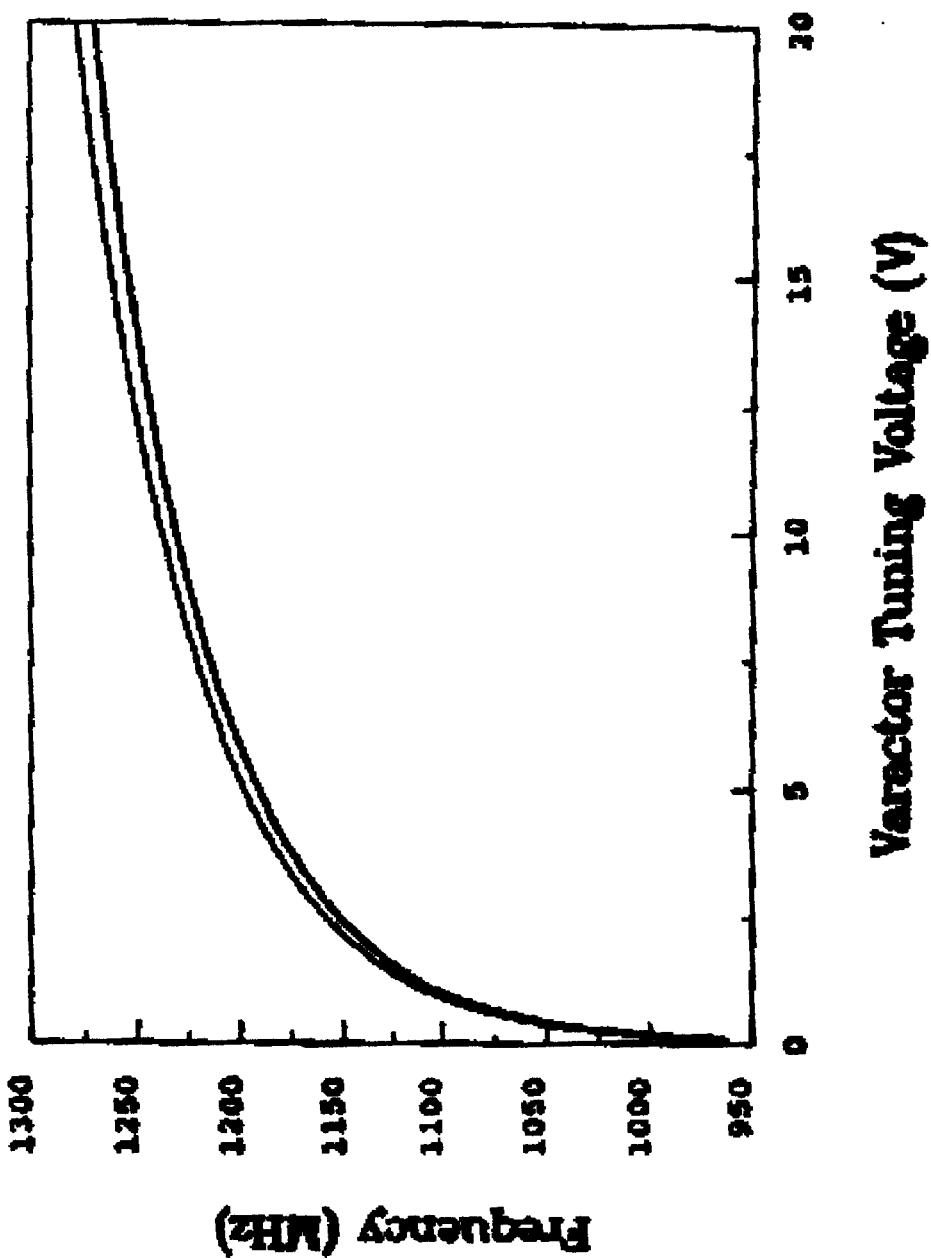
FIG. 15B shown actual measured results from measurement of molecular modification of proton (thermally) (i.e. cooking), using a planar probe with a sheath cover.
Figure 15C:
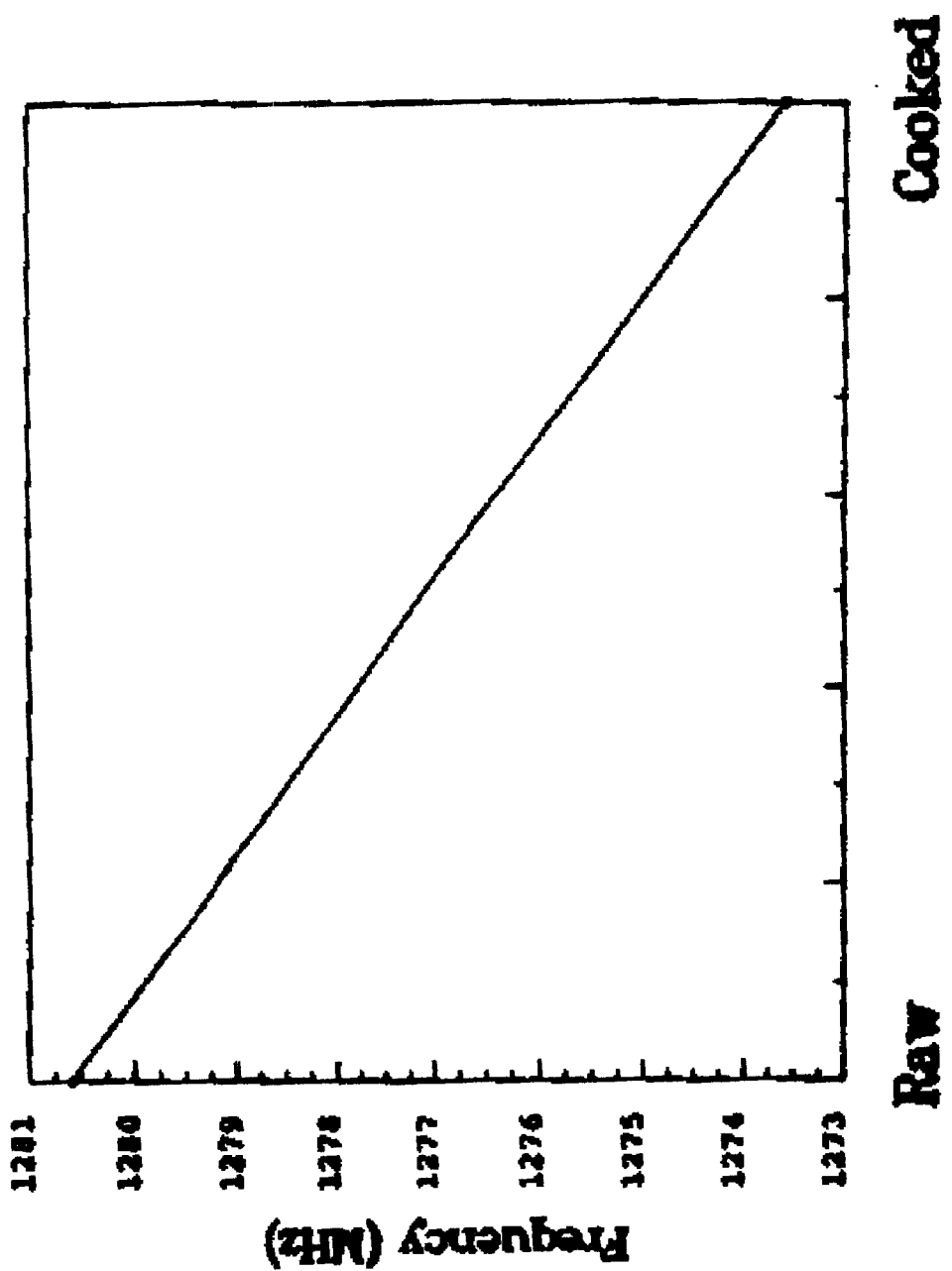
FIG. 15C is an expanded plot of some key data points from the plot of FIG. 15B.

FIG. 15B shows actual measured results from measurement of molecular modification of protein (thermally) (i.e. cooking), using a planar probe with a sheath cover. The top curve shows measurement of an uncooked slurry of animal protein in water. In this curve the oscillator frequency goes from about 1189 MHz to about 1281 MHz as the tuning voltage is ramped from 6.6 V to 19.8 V. The bottom curve shows measurement of the same slurry composition after cooking. In this curve the oscillator frequency goes from about 1189 MHz to about 1274 MHz as the tuning voltage is ramped from 6.6 V to 19.8 V. FIG. 15C is an expanded plot of some key data points from the plot of FIG. 15B. (The numbers on the X-axis of this plot are insignificant; this plot is merely a graphic way to indicate the large observed difference in oscillator frequency at a given tuning voltage. By dividing this observed frequency difference by the frequency resolution of 30 Hz, it may be seen that the plotted difference is many times the least-measurable-increment).

It should be noted that such electrical measurement of cooking operations is preferably used in combination with temperature monitoring. However, since many cooking operations are isothermal, temperature measurement cannot provide endpoint detection. Alternatively, a controlled time/temperature profile can be used, but this too does not permit endpoint detection by measurement of temperature.

Figure 16A:
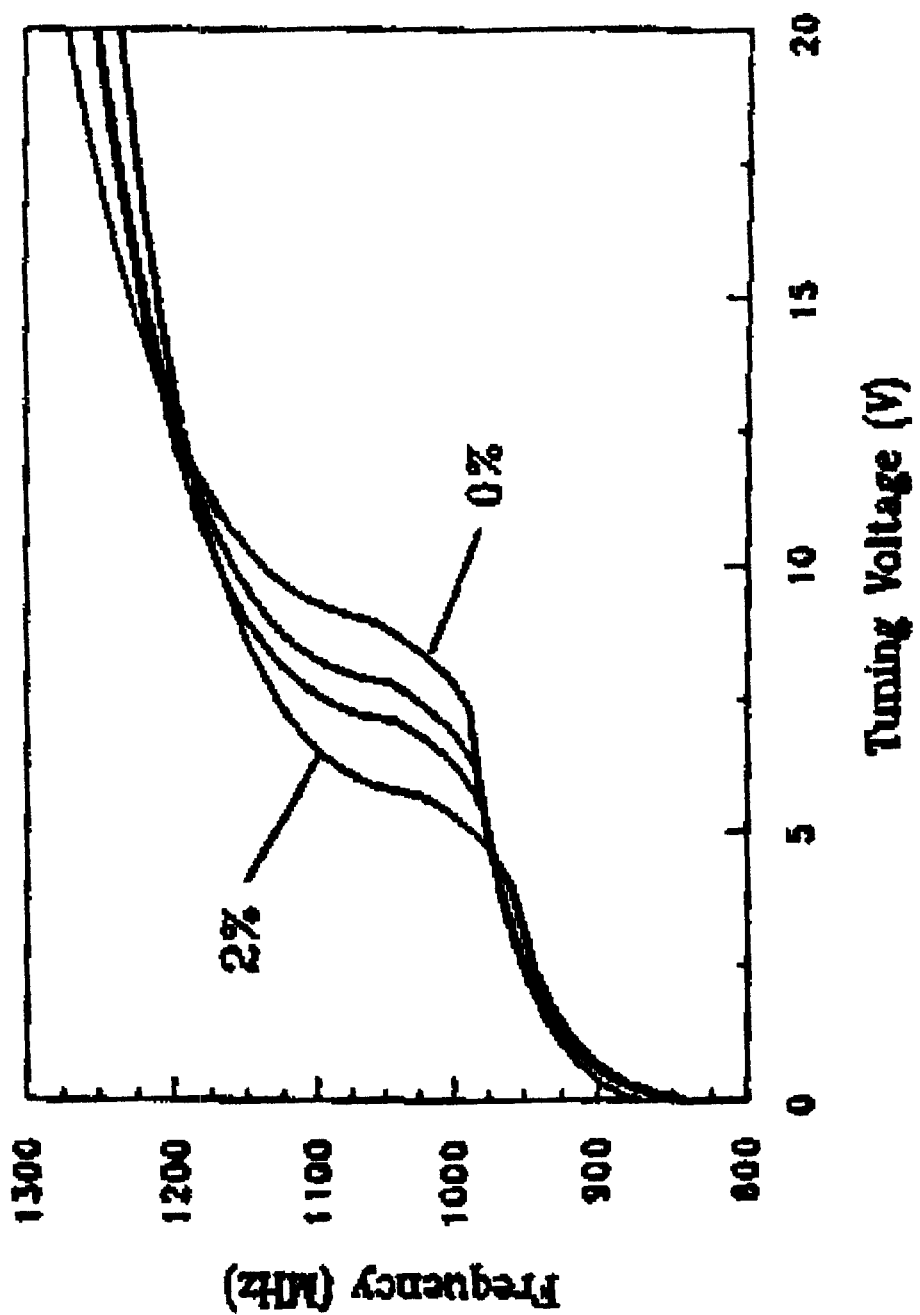
FIG. 16A shows a family of curves from measurement of glucose concentration in a 0.1% saline solution.
Figure 16B:
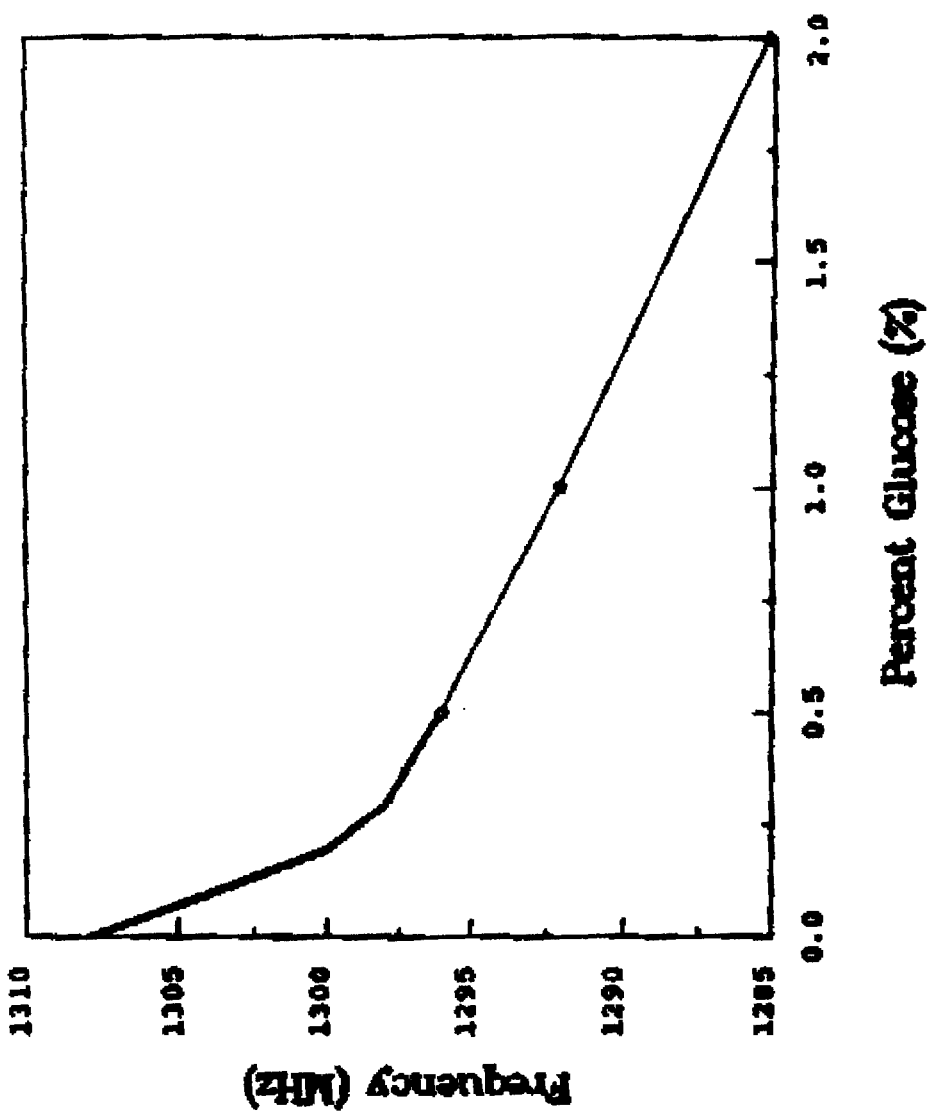
FIG. 16B is a breakout of datapoints from the family of curves of FIG. 16A.

FIG. 16A shows a family of curves from measurement of glucose concentration in a 0.1% saline solution. The measurements were performed with a planar, bare, shorted probe configuration at room temperature. In the plot for a 2% solution, the oscillator frequency goes from about 1202 MHz to about 1210 MHz as the tuning voltage is ramped from 6.6 V to 8.8 V. Also plotted for comparison is a solution with no glucose present. In this curve the oscillator frequency goes from about 1163 MHz to about 1178 MHz as the tuning voltage is ramped from 6.6 V to 8.8 V. (In general, the 0% point in "binary" plots of complex systems is usually significantly separated from the other points, as in the example shown. This is usually caused by hydrolization or formation of other bonds.) The intermediate curves correspond to intermediate concentrations (1% and 0.5%) of glucose. FIG. 16B is a breakout of datapoints from the family of curves of FIG. 16A. (The numbers on the X-axis of this plot are insignificant; this plot is merely a graphic way to indicate the large observed difference in oscillator frequency at a given tuning voltage. By dividing this observed frequency difference by the frequency resolution of 30 Hz, it may be seen that the plotted difference is many times the least-measurable-increment.)

Figure 19A:
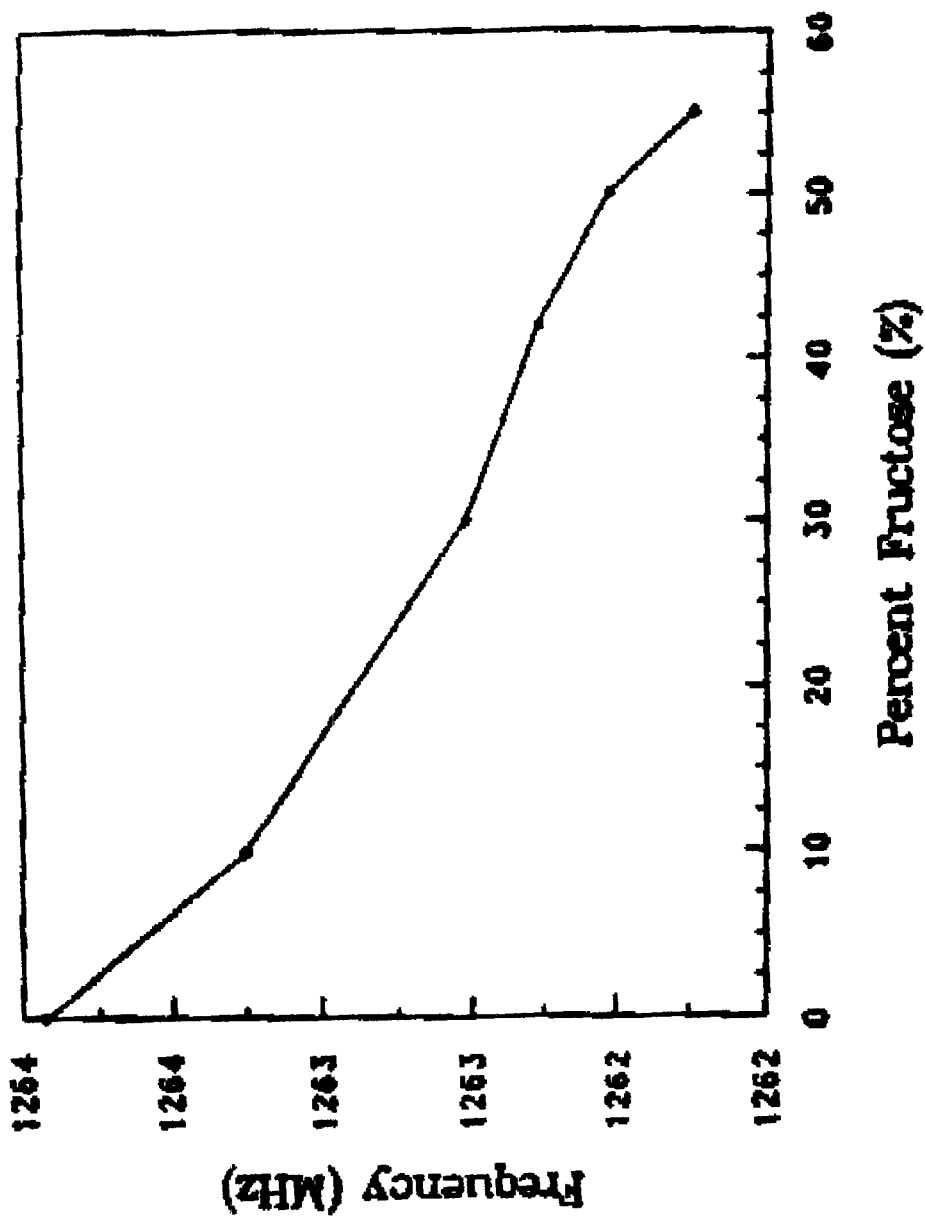
FIGS. 19A shows actual data from in-situ monitoring of enzymatic conversion of glucose to a glucose/fructose mixture, using a planar probe.
Figure 19B:
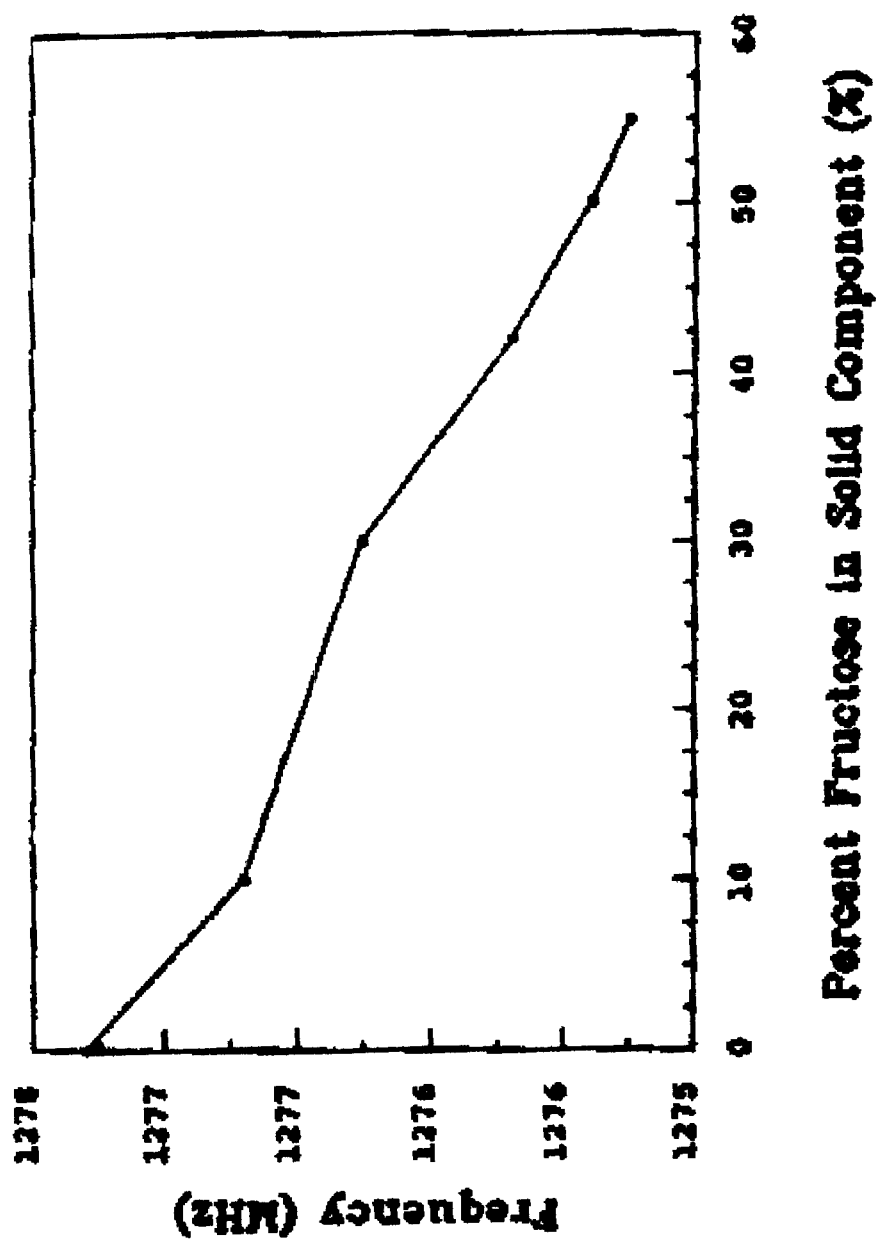
FIG. 19B is an expanded plot of some key data points from the plot of FIG. 19A.

FIGS. 19A and 19B show measurement of the fructose percentage in a range of glucose/fructose mixtures, using a bare planar probe. FIG. 19A shows measurements at a constant tuning voltage of 15 V. In this curved the oscillator frequency goes from about 1263.9 MHz to about 1261.8 MHz as the concentrations varies from 0% wt fructose to 54% wt fructose. FIG. 19B shows measurements at a constant tuning voltage of 20 V. In this curve the oscillator frequency goes from about 1277.3 MHz to about 1275.3 MHz as the concentration varies from 0% wt fructose to 54% wt fructose. In all of these experimental measurements, the initial mixture was 45% solids and 55% $H_2O$ by weight. This capability permits high-resolution in-situ real-time monitoring of enzymatic conversion of glucose to a glucose/fructose mixture.

One of the common goals of food processing is to prepare sweetened material from grains, particularly corn (maize). The normal processing cycle uses a series of enzymatic and catalytic digestion steps in the sequence starch→dextrin→maltose→glucose+fructose. (Fructose is an attractive end-product, since it is much sweeter than glucose.)

Figure 20:
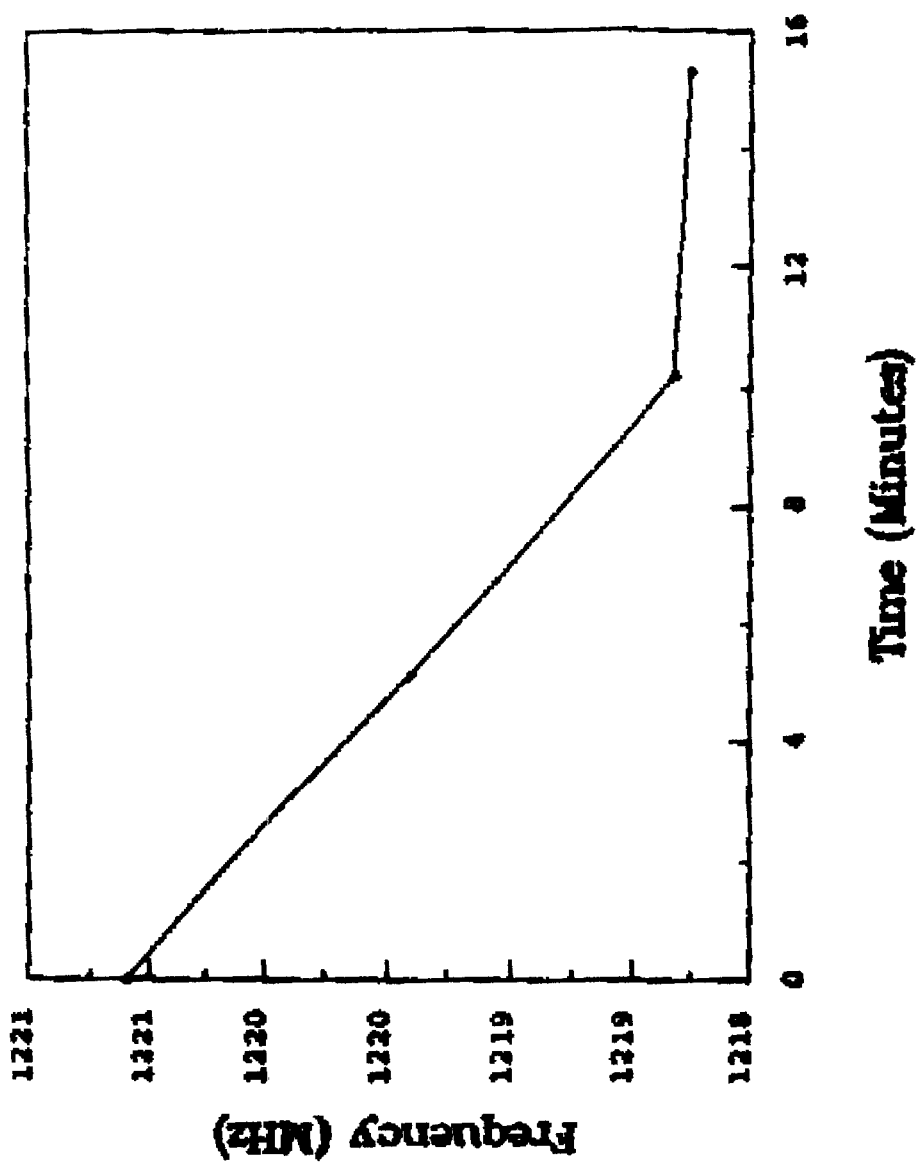
FIG. 20 shows actual data from in-situ monitoring of relative absorption of glucose from a protein/saline solution onto a modified zeolite, using a planar probe (as shown in FIG. 4C) with an added selective absorption layer and a stabilizing overcoat.

FIG. 20 shows actual data from in-situ real-time monitoring of selective absorption of glucose from a protein/saline solution onto a modified zeolite, using a planar probe (as shown in FIG. 4C) with an added selective absorption layer and a stabilizing overcoat. The solution consists of 10% protein (emulsion), 0.1% NaCl saline solution, and 5% glucose solution all measured at room temperature. In this curve the oscillator frequency (at a constant tuning voltage of 10 V) goes from about 1220.6 MHz to about 1218.3 MHz within about 10 minutes after immersion. At this time the absorber was apparently approaching equilibrium (or becoming loaded), since the rate of change of the oscillator frequency was markedly reduced. The final measured data point showed an oscillator frequency of about 1218.2 MHz after 15 minutes. The protein in this mixture shows that the selective absorption measurement works well in the presence of other complex biomaterials. Thus, this operation may be used for monitoring simple materials (such as glucose) in very complex mixtures (such as food ingredients, or materials of medical interest such as blood or urine).

Figure 23:
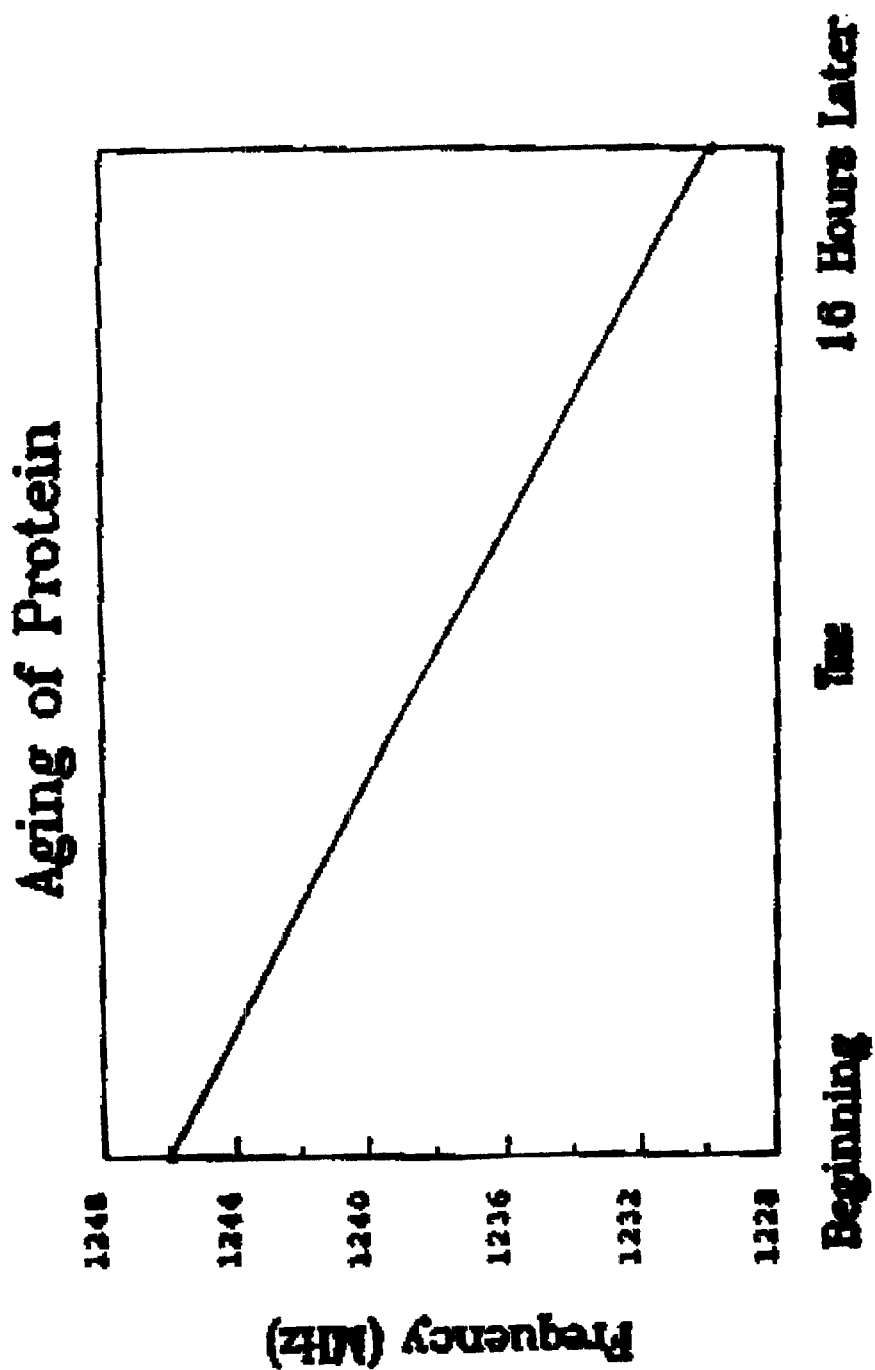
FIG. 23 shows measurement of aging of a fat/protein mixture at ambient temperature.

FIG. 23 shows aging of a fat/protein mixture at ambient temperature. A blended mix of 1 part animal protein in 2 parts of water was allowed to age in an uncovered beaker for 16 hours at room temperature (about 25° C.). Thus, this system provides a proxy for deterioration of protein-rich food produces due to oxidation, bacterial growth, etc. Time-resolved measurements were taken, without sweeping the oscillator ($V_{tun}$=12 V), at two points 16 hours apart. During the 16 hours, the oscillator frequency changed from 1245.62 MHz to 1230.1 MHz, for a change of 15.52 MHz. The specified resolution of the frequency measurement apparatus used (shown in FIG. 10) is about 30 Hz. (The actual resolution is significantly better—probably close to 10 Hz). Thus, the measured change is more than 500,000 times the minimum measurable increment. The shape of the curve is typically an exponential or power-law curve, but straight-line interpolation of the number of datapoints over the time interval corresponds to one detectable increment every seven seconds! Thus, even assuming that the rate of change is much slower at first, the very high resolution provided by the disclosed invention permits accurate detection of the smaller rate of change at the beginning of the process.

Further Modifications and Variations

It will be recognized by those skilled in the art that the innovative concepts disclosed in the present application can be applied in a wide variety of contexts. Moreover, the preferred implementation can be modified in a tremendous variety of ways. Accordingly, it should be understood that the modifications and variations suggested below and above are merely illustrative. These examples may help to show some of the scope of the inventive concepts, but these examples do not nearly exhaust the full scope of variations in the disclosed novel concepts.

For example, the preferred method of monitoring the characteristics of the material in the test loop is simply by observing the shifts in the frequency of the free-running oscillator, as discussed above; but in an alternative class of embodiments, the behavior of the free-running oscillator may be observed in a different way: instead of monitoring the frequency of oscillation, a phase-lock loop configuration can be used, and the error signal of the phase-lock loop tracked. This is essentially equivalent to observing the frequency shifts which would have occurred without the feedback control relationship used to implement the phase-locked-loop (or frequency-locked-loop) configuration.

In phase-locked-loop systems, a phase detector is used to detect phase differences between a reference signal and the output of a voltage-controlled oscillator. The phase-detector generates an error signal accordingly, which is usually combined with a control signal, and fed back to control the voltage-controlled oscillator. Thus, the voltage-controlled oscillator very accurate tracks the reference signal, even if the frequency of reference signal varies. See Phase Locked Loops (Edited William Lindsey and Chak M. Chie, 1986); Floyd M. Gardner, Phaselock Techniques (2nd Ed., 1979); Roland E. Best, Phase-locked Loops (1984); D. Wolaver, Phaselocked Loop Circuit Design (1991); all of which are hereby incorporated by reference. Of course, for high frequency systems, as in some embodiments of the present invention, conversion is used before the phase detection operation. In addition, as detailed in the foregoing references, higher-order phase-locked-loops with multiple stages of feedback can be used, and nonlinear relations can be added if desired.

Some background on microwave phase-locked loops may be found in the article by Zvi Galani and Richard Campbell, at 39 IEEE Transactions on Microwave Theory and Techniques, 782 (May 1991), which is hereby incorporated by reference.

In modern telecommunications technology, analog phase-locked-loops have been very widely replaced by digital PLL's. In a digital phase-locked-loop, the error signal is a numerical value, and the voltage-controlled oscillator is instead a numerically-controlled oscillator. Discussion of such digital PLL circuits may be found, for example, a W. C. Lindsey and C. M. Chie, "A survey of digital phase-locked loops," 69 PROCEEDINGS OF THE IEEE 410ff (1981), and the comments on that article published at 70 PROC. IEEE 201ff (1982).

As will be recognized by those skilled in the art, the innovative concepts described in the present application can be modified and varied over a tremendous range of applications, and accordingly the scope of patented subject matter is not limited by any of the specific exemplary teachings given.

What is claimed is:

1. A method for controlling a process, comprising the steps of:

providing a voltage-controlled oscillator which is connected to be pulled by the varying susceptance seen at a load connection thereto, and which is connected to be tuned by a tuning voltage applied thereto;

connecting said load connection to an RF interface which is electrically loaded by proximity to material undergoing the process;

sweeping said tuning voltage across a predetermined range of voltages;

integrating the oscillation frequency of said oscillator, as a function of the tuning voltage, across said range of voltages, to provide a process index value;

comparing said process index value with a known range of values for comparable process conditions; and taking action conditionally, within said process, in dependence on the result of said comparing step.

2. The method of claim 1, wherein said oscillator is a voltage-controlled oscillator, and wherein said sweeping step sweeps said oscillator across a wide range of frequencies while monitoring the dependence of the oscillator frequency on the tuning voltage.

3. The method of claim 1, wherein said RF interface consists of a single-ended probe.

4. The method of claim 1, wherein said RF interface consists of a single-ended probe which is immersed in a fluid stream of said process.

5. A method for detecting the composition and microstructure of materials, comprising the steps of:

providing an oscillator which is connected to be pulled by the varying susceptance seen at a load connection thereto;

connecting said load connection to the material under test through a single-ended probe which includes an RF switch and first and second transmission line structures, said switch being connected and configured to connect said first transmission line structure to said external connection selectively under remote command;

positioning said probe so that at least one of said transmission line structures is electrically loaded by proximity to a portion of the material to be characterized; and observing changes in the frequency of said oscillator, while switching said RF switch to activate said first and second transmission lines alternately.

6. The method of claim 5, wherein said observing step monitors not only the frequency of said oscillator, but also insertion loss of said probe.

* * * * *